(12) United States Patent
Valenta et al.

(10) Patent No.: US 9,103,835 B2
(45) Date of Patent: Aug. 11, 2015

(54) HYPOALLERGENIC HYBRID POLYPEPTIDES FOR THE TREATMENT OF ALLERGY

(75) Inventors: Rudolf Valenta, Theresienfeld (AT); Birgit Linhart, Weissenkirchen (AT); Margarete Focke-Tejkl, Vienna (AT); Angela Neubauer, Maria Anzbach (AT); Peter Valent, Vienna (AT); Katharina Blatt, Gross-Enzersdorf (AT)

(73) Assignee: BIOMAY AG, Vienna (AT)

( * ) Notice: Subject to any disclaimer, the term of this patent is extended or adjusted under 35 U.S.C. 154(b) by 0 days.

(21) Appl. No.: 13/395,596

(22) PCT Filed: Sep. 9, 2010

(86) PCT No.: PCT/EP2010/063230
§ 371 (c)(1),
(2), (4) Date: May 8, 2012

(87) PCT Pub. No.: WO2011/029869
PCT Pub. Date: Mar. 17, 2011

(65) Prior Publication Data
US 2012/0207788 A1 Aug. 16, 2012

Related U.S. Application Data

(60) Provisional application No. 61/241,049, filed on Sep. 10, 2009.

(30) Foreign Application Priority Data

Sep. 10, 2009 (EP) ..................................... 09169958

(51) Int. Cl.
| | |
|---|---|
| A61K 39/00 | (2006.01) |
| A61K 39/35 | (2006.01) |
| A61K 39/36 | (2006.01) |
| A61K 38/00 | (2006.01) |
| C07K 1/00 | (2006.01) |
| C07K 14/00 | (2006.01) |
| C07K 17/00 | (2006.01) |
| G01N 33/68 | (2006.01) |
| C07K 14/415 | (2006.01) |
| C07K 16/16 | (2006.01) |
| G01N 33/50 | (2006.01) |

(52) U.S. Cl.
CPC ............ *G01N 33/6854* (2013.01); *A61K 39/35* (2013.01); *A61K 39/36* (2013.01); *C07K 14/415* (2013.01); *C07K 16/16* (2013.01); *G01N 33/505* (2013.01); *C07K 2319/00* (2013.01)

(58) Field of Classification Search
None
See application file for complete search history.

(56) References Cited

U.S. PATENT DOCUMENTS

| 7,491,396 B2 | 2/2009 | Mothes et al. |
|---|---|---|
| 2002/0173625 A1* | 11/2002 | Linhart et al. ................. 530/350 |
| 2008/0286311 A1 | 11/2008 | Westritschnig et al. |
| 2009/0098167 A1 | 4/2009 | Ball et al. |
| 2012/0009210 A1 | 1/2012 | Campana et al. |

FOREIGN PATENT DOCUMENTS

| EP | 1 219 301 A1 | 7/2002 |
|---|---|---|
| EP | 1 440 979 A1 | 7/2004 |
| EP | 2 475 386 | 7/2012 |
| WO | WO 2006/058359 | 6/2006 |
| WO | WO 2007/124526 | 11/2007 |

OTHER PUBLICATIONS

Blumenthal et al. Definition of an Allergen/Allergens and Allergen Immunotherapy. Ed. R Lockey, S. Bukantz and J. Bousquet. New York: Marcel Decker, 2004.37-50.*
Ball et al. "Reducing allergenicity by altering allergen fold: a mosaic protein of Phl p 1 for allergy vaccination." Allergy. 64: 569-580, 2009.*
Traidl-Hoffman et al. 'Determinants of allergenicity.' J. Allergy Clin Immunol. 123:558-566, 2009.*
Wallner et al. 'Allergy multivaccines created by DNA shuffling of tree pollen allergens.' J. Alergy. Clin Immunol. 120:374-380, 2007.*
Linhart, B. et al., *FASEB Journal*, vol. 16, No. 10, pp. 1301-1303 (Aug. 2002).
Linhart, B. et al., *Journal of Allergy and Clinical Immunology*, vol. 115, No. 5, pp. 1010-1016 (May 1, 2005).
Linhart, B. et al., *Biological Chemistry*, vol. 389, No. 7, pp. 925-933 (Jul. 1, 2008).
Mothes-Luksch, N. et al., *Journal of Immunology*, vol. 181, No. 7, pp. 4864-4873 (Oct. 1, 2008).
Schramm, G. et al., *Journal of Immunology*, vol. 162, No. 4, pp. 2406-2414 (Feb. 15, 1999).
Vrtala, S. et al., *Journal of Immunology*, vol. 179, No. 3, pp. 1730-1739 (Aug. 1, 2007).
Westritschnig, K. et al., *Journal of Immunology*, vol. 179, No. 11, pp. 7624-7634 (Dec. 1, 2007).
Schenk S et al., "T-cell epitopes of Phl p 1, major pollen allergen of timothy grass (Phleum pratense): evidence for crossreacting and non-crossreacting T-cell epitopes with grass group I allergens", J Allergy Clin Immunol, Dec. 1995, vol. 96(6 Pt 1), pp. 986-96. (abstract only).
Fischer et al., "Characterization of Phl p 4, a major timothy grass (Phleum pratense) pollen allergen", J Allergy Clin Immunol, Jul. 1996 vol. 98(1), pp. 189-98. (abstract only).
Müller WD et al., "Mapping of T-cell epitopes of Phl p 5: evidence for crossreacting and non-crossreacting T-cell epitopes within Phl p 5 isoallergens", L. Clin Exp Allergy, Dec. 1998, vol. (12), pp. 1538-1548. (abstract only).
Excerpts from the Immune Epitope Database and Analysis Resource, www.iedb.org, retrieved Sep. 10, 2014.

* cited by examiner

*Primary Examiner* — Nora Rooney
(74) *Attorney, Agent, or Firm* — Chalin A. Smith; Smith Patent

(57) ABSTRACT

The present invention relates to a method for identifying hypoallergenic polypeptides and to a corresponding screening method. The invention further relates to hypoallergenic polypeptides identified by the method of the invention and to the prophylactic and therapeutic use of these polypeptides.

2 Claims, 11 Drawing Sheets

Figure 4

Patient 9

Patient 10

HYPOALLERGENIC HYBRID POLYPEPTIDES FOR THE TREATMENT OF ALLERGY

This application corresponds to the national phase of International Application No. PCT/EP2010/063230 filed Sep. 9, 2010, which, in turn, claims priority to European Patent Application No. 09.169958.7 filed Sep. 10, 2009 and U.S. Provisional Patent Application No. 61/241,049 filed Sep. 10, 2009, all of which are incorporated by reference herein in their entirety.

BACKGROUND OF THE INVENTION

More than 10% of the world population suffer from allergy to grass pollen. Here we describe the development of a vaccine based on recombinant hypoallergenic hybrid molecules which were constructed out of elements derived from the four major timothy grass pollen allergens Phl p 1, Phl p 2, Phl p 5, and Phl p 6 for the treatment of grass pollen allergy. Codon-optimized synthetic genes encoding building blocks and combinations of the four allergens were designed according to epitope mapping studies and structural data and subsequently expressed in *Escherichia coli*. Seventeen recombinant hybrid molecules were purified by affinity chromatography and evaluated regarding expression, purity and fold, solubility, and reduced allergenic activity. Four hypoallergenic hybrid molecules consisting of reassembled elements of the four grass pollen allergens were identified which upon immunization in different animal models induced IgG antibodies blocking IgE recognition of the grass pollen allergens by allergic patients. These hypoallergenic hybrid molecules represent safe vaccines for immunotherapy of grass pollen allergy.

IgE-mediated allergies represent a worldwide health problem with increasing prevalence (1). The hallmark of allergic disease is the production of IgE antibodies specific for environmental allergens, mainly from pollen, mites, animal dander, and moulds (1). Allergic symptoms occur, when receptor-bound IgE on mast cells or basophils is cross-linked by multivalent allergen, leading to the release of inflammatory mediators (2). In addition, IgE-facilitated presentation via FcεRI and FcεRII on antigen presenting cells strongly enhances the activation of allergen-specific T cells contributing to T cell mediated allergic inflammation (3, 4). Allergen-specific immunotherapy currently represents the only causative treatment of allergies with a long-term effect, although its success is impaired by the use of crude allergen extracts (5, 6). These preparations contain allergenic and non-allergenic material in varying amounts, whereby the presence of biologically active compounds increases the risk of anaphylactic side effects. In addition, the lack or poor immunogenicity of clinically relevant allergens reduces the efficacy of extract-based vaccines (7). Substantial progress has been made in the field of allergen characterization during the last 20 years through the application of immunochemical and molecular biological techniques. Today, the most common and important allergens have been characterized regarding their structure and immunological properties. Recombinant allergens closely resembling the properties of the natural allergens have been produced and can now be used for the diagnosis and therapy of allergy (5). In addition it has been shown that allergen derivatives with beneficial immunological properties can be engineered (8). Modified variants of allergens with reduced allergenic activity have been generated, in order to avoid IgE-mediated side effects in the course of immunotherapy and recombinant Bet v 1-derived fragments with strongly reduced IgE-binding capacity have already been used in a clinical trial (9). Hybrid molecules consisting of combinations of different allergens have been shown to increase the immunogenicity of their single components (10-12).

Linhart et al. (Ref. 21) prepared a hypoallergenic hybrid molecule with increased immunogenicity by combining hypoallergenic derivatives of the two major grass pollen allergens Phl p 2 and Phl p 6, namely a Phl p 2 mosaic molecule and a deletion mutant of Phl p 6, which was not surprising in light of previous data (Ref. 15, 17).

The present inventors now have found that a combination of the hybrid technology and the mosaic technology does not in all cases lead to hypoallergenic molecules. Surprisingly, it has been observed that two fusion polypeptides which consisted of the same fragments but in a different order exhibited very different IgE reactivities. The present invention therefore provides a method for identifying polypeptides that have hypoallergenic properties and can serve as a potential vaccine.

SUMMARY OF THE INVENTION

The present invention relates to a method for identifying hypoallergenic polypeptides, comprising the following steps:
a) providing a group of polypeptides, each polypeptide comprising N fragments derived from at least two different allergens, wherein the combined amino acid sequence of any pair of two adjacent fragments within the polypeptide is not present as a consecutive amino acid sequence in any one of said allergens, wherein N is an integer greater than 3;
b) determining the IgE reactivity of the polypeptides;
c) determining the T cell reactivity of the polypeptides;
d) determining whether the polypeptides are capable of inducing an IgG response directed against said allergens;
e) determining whether the polypeptides are capable of inducing a protective IgG response blocking allergic patients' IgE binding to said allergens;
f) selecting those polypeptides which (i) have lower IgE reactivity than any one of said allergens, (ii) exhibit T cell reactivity, (iii) are capable of inducing an IgG response directed against one or more of said allergens, and (iv) are capable of inducing a protective IgG response blocking allergic patients' IgE binding to said allergens.

In one embodiment at least two polypeptides within said group of polypeptides comprise the same fragments assembled in a different order.

In another embodiment all fragments within said polypeptides have a length of from 20 to 100 amino acids.

In another embodiment said polypeptides consist of 4 to 12 fragments derived from two different allergens.

In another embodiment the method further comprises the step of evaluating the secondary structure of the polypeptides provided in step (a), and selecting the polypeptide(s) which exhibit(s) random coiled structure.

In another embodiment said allergens are selected from the group consisting of the grass pollen allergens Phl p 1, Phl p 2, Phl p 3, Phl p 4, Phl p 5, Phl p 6, Phl p 7, Phl p 11, Phl p 12 and Phl p 13.

In another embodiment each fragment consists of an amino acid sequence selected from the group consisting of SEQ ID NOs: 55 through 76.

In another embodiment at least one polypeptide in said group comprises an amino acid sequence selected from the group consisting of SEQ ID NOs: 21 through 37.

Another aspect of the present invention is a hypoallergenic polypeptide comprising at least four fragments derived from at least two different allergens, wherein the combined amino acid sequence of any pair of two adjacent fragments within the polypeptide is not present as a consecutive amino acid sequence in said allergens, characterized in that at least one fragment is derived from Phl p 1, Phl p 5, Phl p 2 or Phl p 6.

Yet another aspect of the present invention is a hypoallergenic polypeptide comprising at least four fragments derived from at least two different allergens, wherein the combined amino acid sequence of any pair of two adjacent fragments within the polypeptide is not present as a consecutive amino acid sequence in said allergens, characterized in that each of said fragments consists of an amino acid sequence selected from the group consisting of SEQ ID NOs: 55 through 76.

In one embodiment the hypoallergenic polypeptide comprises an amino acid sequence selected from the group consisting of SEQ ID NOs:22, 23, 24, 25, 36 and 37.

In another embodiment the hypoallergenic polypeptide consists of an amino acid sequence selected from the group consisting of SEQ ID NOs:39, 40, 41, 42, 53 and 54.

Another aspect of the invention is a pharmaceutical composition comprising the polypeptide of the invention and a pharmaceutically acceptable diluent or excipient.

Another aspect of the invention is the use of the polypeptide of the invention for the manufacture of a medicament for the prevention and/or treatment of allergy, preferably of grass pollen allergy.

Another aspect of the invention is a nucleic acid encoding the polypeptide of the present invention.

Yet another aspect of the invention is a method of treating and/or preventing an allergic disorder, comprising administering to an individual in need thereof a therapeutically effective amount of the polypeptide or polynucleotide of this invention.

BRIEF DESCRIPTION OF THE DRAWINGS

Figure 4:
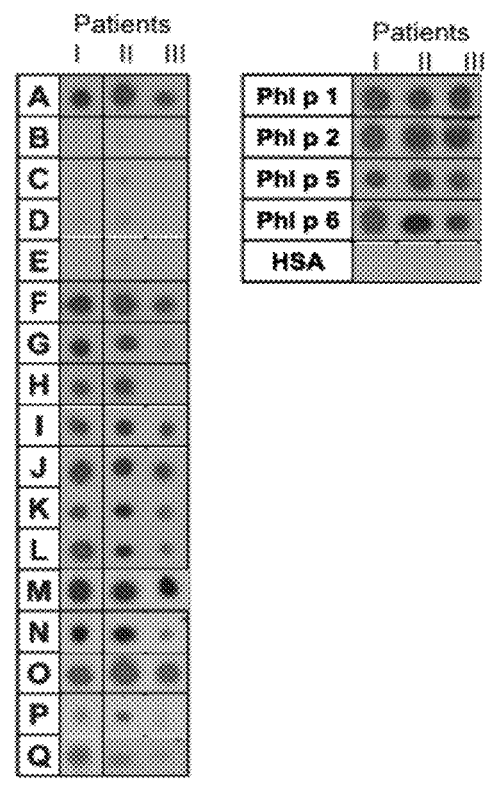

FIG. 4 depicts IgE-reactivity to nitrocellulose bound hybrids and control proteins for three representative grass pollen allergic patients (see Example 3).

DETAILED DESCRIPTION OF THE INVENTION

Figure 1:
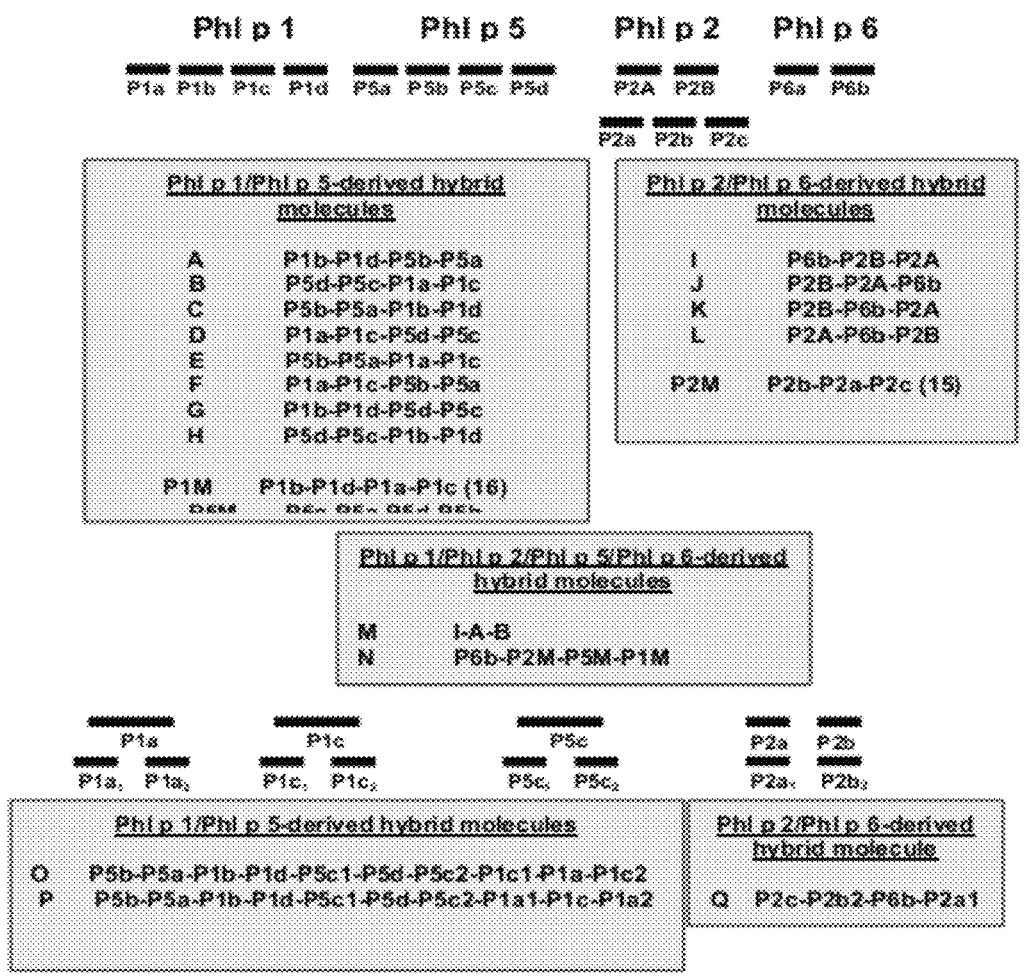
FIG. 1 depicts the design of hybrid molecules by the assembly of allergen fragments derived from the major timothy grass pollen allergens Phl p 1, Phl p 2, Phl p 5, and Phl p 6 (see Example 1).

The method of the invention is a method for identifying hypoallergenic polypeptides. Alternatively, the method of the invention is a screening method to identify hypoallergenic polypeptides. The term "hypoallergenic" as used herein, means the reduction of IgE reactivity and ability to induce IgE-mediated mast cell or basophil degranulation.

In its first step, the method of the invention comprises providing a group of polypeptides, wherein each polypeptide within said group independently comprises N fragments derived from at least two different allergens.

The Polypeptides

The group of polypeptides consists of at least two different polypeptides. Preferably, the group of polypeptides consists of 2 to 100, preferably of 3 to 75, more preferably of 4 to 50, most preferably of 5 to 30 different polypeptides.

Each polypeptide independently comprises or consists of N fragments derived from at least two different allergens. N is an integer greater than 3, preferably N is 4 to 25, more preferably 4 to 20, still more preferably 4 to 15, most preferably 4 to 10 (e.g. 4, 5, 6, 7, 8, 9 or 10). The polypeptides within the group may comprise or consist of the same or a different number of fragments. That is, N may be the same or different for the respective polypeptides within the group. Preferably, all fragments within a given polypeptide are different from each other.

Each fragment consists of at least 8, preferably of 8 to 100, more preferably of 10 to 90, still more preferably of 12 to 80, more preferably of 15 to 70, more preferably of 20 to 60 consecutive amino acids from an allergen amino acid sequence.

The polypeptide prepared in accordance with this invention does not necessarily consist only of amino acid sequences derived from the allergens. It is possible that non-native sequences (e.g. spacer sequences) are inserted between the fragments (which fragments are consecutive amino acid sequences from different allergens). It is also possible that the polypeptides comprise a tag sequence which facilitates the purification of the polypeptide upon expression in a host cell. An example of such a tag sequence is a hexahistidine tag which allows purification by $Ni^{2+}$ chelate chromatography. Other tags are known to those of skill in the art. Furthermore, the polypeptide may contain a foreign methionine residue at amino acid position 1 which results from expression in host cells. The methionine will often be present if the N-terminal portion of the polypeptide is an internal or C-terminal allergen fragment In one embodiment, the polypeptide may consist of any one of the following structures (I) to (VII):

(I) Met-F1-F2-. . . -FN-tag,
(II) Met-F1-F2-. . . -FN,
(III) F1-F2-. . . -FN-tag,
(IV) Met-tag-F1-F2-. . . -FN,
(V) tag-F1-F2-. . . -FN,
(VI) tag-F1-F2-. . . -FN-tag,
(VII) F1-F2-. . . -FN wherein Met is an N-terminal methionine residue, F1, F2 and FN are the first, second and Nth fragment, respectively, and tag is a tag sequence (e.g. a hexahistidine tag $(His)_6$). In the above embodiments (I) through (VII), there are no foreign amino acids between the fragments. That is, F1-F2-. . . -FN is a consecutive sequence of allergen fragments. In other embodiments, there may be one or more (e.g. 1, 2 or 3) foreign amino acids between the fragments. This, however, is not preferred.

The polypeptide in accordance with this invention may be prepared by various methods. In one embodiment the polypeptide is prepared by expressing a polynucleotide in a host cell. The host cell may be a prokaryotic or eukaryotic cell. If prokaryotic cells are used the host cell is preferably *E. coli*. Examples of eukaryotic cells include yeast, insect cells or cell lines such as CHO cells. After introducing a suitable polynucleotide encoding the polypeptide of the invention into a host cell the host cell is cultured under conditions such that the polypeptide is expressed in the cell. The polypeptide may be secreted by the cell or accumulate inside the cell. Known purification techniques can be used to recover the polypeptide from the cell or from the culture medium.

In another embodiment the polypeptide is prepared by chemical synthesis, e.g. by solid phase synthesis according to techniques that are known per se.

Allergens

The term "allergen" as used herein denotes a substance capable of eliciting a type I-hypersensitivity reaction in atopic individuals. Most humans mount significant Immunoglobulin E (IgE) responses only as a defense against parasitic infections. However, some individuals mount an IgE response against common environmental antigens. This hereditary predisposition is called atopy. In atopic individuals, non-parasitic antigens stimulate inappropriate IgE production, leading to type I hypersensitivity.

Allergens in the sense of the present invention include allergens from plants and animals (Allergome database: www.allergome.org). The allergens are usually wildtype allergens. The allergens may be allergens from one or more of the following species: *Acarus siro, Blomia tropicalis, Dermatophagoides farinae, Dermatophagoides microceras, Dermatophagoides pteronyssinus, Euroglyphus maynei, Glycyphagus domesticus, Lepidoglyphus destructor, Tyrophagus putrescentiae, Blattella germanica, Periplaneta americana, Harmonia axyridis, Archaeopotamobius sibiriensis, Artemia franciscana, Charybdis feriatus, Crangon crangon, Homarus americanus, Litopenaeus vannamei, Metapenaeus ensis, Panulirus stimpsoni, Penaeus aztecus, Penaeus indicus, Penaeus monodon, Pontastacus leptodactylus, Aedes aegypti, Chironomus kiiensis, Chironomus thummi thummi, Forcipomyia taiwana, Triatoma protracta, Apis cerana, Apis dorsata, Apis mellifera, Bombus pennsylvanicus, Bombus terrestris, Dolichovespula arenaria, Dolichovespula maculata, Myrmecia pilosula, Polistes annularis, Polistes dominulus, Polistes exclamans, Polistes fuscatus, Polistes gallicus, Polistes metricus, Polybia paulista, Polybia scutellaris, Solenopsis geminata, Solenopsis invicta, Solenopsis richteri, Solenopsis saevissima, Vespa crabro, Vespa mandarinia, Vespula flavopilosa, Vespula germanica, Vespula maculifrons, Vespula pensylvanica, Vespula squamosa, Vespula vidua, Vespula vulgaris, Argas reflexus, Thaumetopoea pityocampa, Ctenocephalides felis felis, Lepisma saccharina, Rana esculenta, Canis familiaris, Felis domesticus, Bos domesticus, Sardinops sagax, Gadus callarias, Gallus domesticus, Oryctolagus cuniculus, Xiphias gladius, Equus caballus, Lepidorhombus whiffiagonis, Cavia porcellus, Mus musculus, Rattus norvegius, Salmo salar, Dendronephthya nipponica, Todarodes pacificus, Helix aspersa, Haliotis midae, Anisakis simplex, Ascaris suum, Alternaria altemata, Cladosporium cladosporioides, Cladosporium herbarum, Curvularia lunata, Aspergillus flavus, Aspergillus fumigatus, Aspergillus niger, Aspergillus oryzae, Penicillium brevicompactum, Penicillium chrysogenum, Penicillium citrinum, Penicillium oxalicum, Fusarium culmorum, Trichophyton rubrum, Trichophyton tonsurans, Candida albicans, Candida boidinii, Epicoccum purpurascens, Coprinus comatus, Psilocybe cubensis, Rhodotorula mucilaginosa, Malassezia furfur, Malassezia sympodialis, Chamaecyparis obtusa, Cryptomeria japonica, Cupressus arizonica, Cupressus sempervirens, Juniperus ashei, Juniperus oxycedrus, Juniperus sabinoides, Juniperus virginiana, Phoenix dactylifera, Asparagus officinalis, Crocus sativus, Ananas comosus, Anthoxanthum odoratum, Cynodon dactylon, Dactylis glomerata, Festuca pratensis, Holcus lanatus, Hordeum vulgare, Lolium perenne, Oryza sativa, Paspalum notatum, Phalaris aquatica, Phleum pratense, Poa pratensis, Secale cereale, Sorghum halepense, Triticum aestivum, Zea mays, Musa acuminata, Apium graveolens, Daucus carota, Ambrosia artemisiifolia, Ambrosia psilostachya, Ambrosia trifida, Artemisia vulgaris, Helianthus annuus, Lactuca sativa, Brassica juncea, Brassica napus, Brassica oleracea, Brassica rapa, Sinapis alba, Beta vulgaris, Chenopodium album, Salsola kali, Cucumis melo, Actinidia chinensis, Actinidia deliciosa, Bertholletia excelsa, Arachis hypogaea, Glycine max, Lens culinaris, Lupinus angustifolius, Pisum sativum, Phaseolus vulgaris, Vigna radiata, Alnus glutinosa, Betula verrucosa, Carpinus betulus, Castanea sativa, Corylus avellana, Juglans nigra, Juglans regia, Quercus alba, Catharanthus roseus, Fraxinus excelsior, Ligustrum vulgare, Olea europea, Plantago lanceolata, Sesamum indicum, Syringa vulgaris, Persea americana, Hevea brasiliensis, Mercurialis annua, Ricinus communis, Platanus acerifolia, Platanus orientalis, Fragaria ananassa, Humulus japonicus, Malus domestica, Morus nigra, Parietaria judaica, Parietaria officinalis, Prunus armeniaca, Prunus avium, Prunus domestica, Prunus dulcis, Prunus persica, Pyrus communis, Rubus idaeus, Ziziphus mauritiana, Vitis vinifera, Anacardium occidentale, Citrus limon, Citrus reticulata, Citrus sinensis, Litchi chinensis, Pistacia vera, Capsicum annuum, Lycopersicon esculenturn, Solanum tuberosum.*

Preferably, one or more allergens are allergens from the species *Phleum pratense, Betula verrucosa, Dermatophagoides pteronyssinus*. Most preferably, one or more allergens are allergens from the species *Phleum pratense*.

In a preferred embodiment of the method of the invention, all allergens from which the fragments are derived are from a single species from the list recited above. That is, the different 'source allergens' are all derived from the same species.

A preferred group of allergens in accordance with this invention are grass pollen allergens, for example allergens from the species *Phleum pratensae*. Preferably, the allergens are selected from the group consisting of Phl p 1, Phl p 2, Phl p 3, Phl p 4, Phl p 5, Phl p 6, Phl p 7, Phl p 11, Phl p 12 and Phl p 13. Most preferably, the allergens are selected from the group consisting of Phl p 1, Phl p 2, Phl p 5 and Phl p 6. The amino acid sequences of selected grass pollen allergens are shown in SEQ ID NO:1 to 10, respectively.

Other specific allergens from which the fragments can be derived include those disclosed in EP 1 817 330 B1, which are incorporated herein in their entirety by reference.

The fragments are derived from at least two different allergens, preferably from 2 to 10 different allergens, more preferably from 2 to 5 different allergens, e.g. from 2, 3, 4 or 5 different allergens.

In a special embodiment the group of polypeptides comprises at least 2 polypeptides which consist of the same fragments but wherein the fragments are assembled in a different order.

Determination of IgE Reactivity

In a further step the method of the invention comprises determining the IgE reactivity of the polypeptides. In a broad sense, the phrase "IgE reactivity" denotes the capability of a substance to bind to IgE antibodies. More specifically, as used herein, the phrase "IgE reactivity" refers to the capability of the polypeptide to bind to IgE antibodies from individuals that are allergic against one or more of the allergens from which the fragments within the polypeptide are derived.

IgE reactivity may be measured by determining the degree of binding between (1) serum IgE from individuals that are allergic against one or more of the allergens from which the fragments are derived and (2) the polypeptide. This may be done by the method described in reference (18) or (19).

Alternatively, IgE reactivity and allergenic activity may be determined by analysing the expression of CD203c on human basophils that were isolated from individuals allergic to one or more of said allergens. See example 4 and reference (20).

Determination of T Cell Reactivity

In a further step the method of the invention comprises determining the T cell reactivity of the polypeptides. The phrase "T cell reactivity" as used herein refers to the capability of a substance to specifically bind to T cell receptors. More specifically, "T cell reactivity" means the capability of the polypeptide to induce proliferation of T cells.

The T cell reactivity of the polypeptides can be measured by (1) providing peripheral blood mononuclear cells (PBMCs) isolated from individuals allergic against one or more of the allergens from which the fragments are derived, and (2) determining the degree of proliferation of T cells contained in said PBMCs. See example 5 and reference (16).

Induction of a Protective IgG Response

In a further step the method of the invention comprises determining the capability of the polypeptides to induce an IgG response against one or more of the allergens from which the fragments are derived. This may be done by (1) immunizing a non-human mammal (e.g. a mouse, rat or rabbit) with the polypeptide, and (2) determining the amount of IgG antibodies raised in said non-human mammal, which are specific to said one or more allergen(s) from which the fragments are derived. The IgG antibodies measured are preferably IgG1 antibodies. Preferably, step (2) is performed using an ELISA assay. See example 6.

The method further comprises determining to which extent the polypeptides are capable of inducing a protective IgG response. This may be done by (1) providing a composition containing IgG antibodies by immunizing a non-human mammal (e.g. a mouse, rat or rabbit) with the polypeptide; (2) providing a composition containing IgE antibodies from individuals that are allergic against one or more of said allergens from which the fragments of the polypeptide are derived, and (3) measuring whether and/or to which extent said composition containing IgG antibodies can block the binding of said IgE antibodies to one or more of said allergens.

This test is preferably performed using an ELISA assay. For example, the wild type allergens from which the fragments are derived may be immobilized on an ELISA plate. The thus pre-treated ELISA plate may then be contacted with said composition containing the IgG antibodies to allow binding of IgG antibodies to said immobilized allergens. After washing the composition containing said IgE antibodies is contacted with the ELISA plate. After washing the amount of IgE antibodies are determined. See Example 7.

Selection of the Polypeptide

The method of the invention comprises the final step of selecting those polypeptides which exhibit favourable properties and are thus useful for the potential use as a vaccine. To be selected a polypeptide must have the following properties:
(i) lower IgE reactivity than one or more of the allergens from which the fragments of the polypeptide are derived;
(ii) T cell reactivity
(iii) capability to induce an IgG response directed against the allergens from which the fragments of the polypeptide are derived; and
(iv) capability to induce a protective IgG response blocking allergic patients' IgE binding to said allergens from which the fragments of the polypeptide are derived.

Regarding item (i) above, the polypeptide is selected if its IgE reactivity is less than that of at least one allergen from which it is derived. Preferably, the polypeptide is selected only if its IgE reactivity is less than that of each allergen from which it is derived. For example, if the polypeptide consists of fragments derived from Phl p 2 and Phl p 5, the polypeptide must have a lower IgE reactivity than Phl p 2, and it must have a lower IgE reactivity than Phl p 5 to be selected.

To be selected the IgE reactivity and allergenic activity are preferably reduced by at least 25%, more preferably by at least 50%, most preferably by at least 90%, determined by quantitative IgE measurements as described in Ref. 16, and as described in Example 4.

Regarding requirement (ii), the polypeptide is selected only if it can elicit allergen-specific T cell activation (Example 5).

Regarding condition (iii), the polypeptide is selected only if it can induce an allergen-specific IgG response upon immunization (see, e.g. Example 6).

Regarding condition (iv), the polypeptide is selected only if the IgG antibodies induced by immunization can inhibit allergic patients' IgE binding to the wildtype allergen (see, e.g., Example 7).

Hypoallergenic Polypeptides Identified by the Method of the Invention

In a further aspect the invention relates to a hypoallergenic polypeptide identified and produced in accordance with this invention.

The hypoallergenic polypeptide may comprise or consist of at least four fragments derived from at least two different allergens, wherein the amino acid sequence of any pair of two adjacent fragments within the polypeptide is not present as a consecutive amino acid sequence in said allergens, characterized in that at least one fragment is derived from Phl p 1 or Phl p 5. The number of fragments may be N, wherein N has the meaning as defined above.

In another embodiment, the hypoallergenic polypeptide of the invention may comprise or consist of at least four fragments derived from at least two different allergens, wherein the amino acid sequence of any pair of two adjacent fragments within the fusion polypeptide is not present as a consecutive amino acid sequence in said allergens, characterized in that each of said fragments consists of an amino acid sequence selected from the group consisting of SEQ ID NOs: 55 through 76. These amino acid sequences are comprised in the fragments used in the examples of the present application. The number of fragments may be N, wherein N has the meaning as defined above. Preferably, The hypoallergenic polypeptide may consist of any one of the following structures (VIII) to (XIV):

(VIII) Met-F1-F2-... -FN-tag,
(IX) Met-F1-F2-... -FN,
(X) F1-F2-... -FN-tag,
(XI) Met-tag-F1-F2-... -FN,
(XII) tag-F1-F2-... -FN, (XIII) tag-F1-F2-....-FN-tag,
(XIV) F1-F2-....-FN wherein Met is an N-terminal methionine residue, F1, F2 and FN are the first, second and Nth fragment, respectively, and tag is a tag sequence (e.g. $(His)_6$), each fragment consisting of an amino acid sequence selected from the group consisting of SEQ ID NOs: 55 through 76. The tag sequence usually is 5 to 10 amino acids in length.

More preferably, the hypoallergenic polypeptide comprises an amino acid sequence selected from the group consisting of SEQ ID NOs:22, 23, 24, 25, 36 and 37. These amino acid sequences are comprised in constructs B, C, D, E, P and Q, respectively (see Examples). The hypoallergenic polypeptide may consist of any one of the following structures (XV) to (XXI):

(XV) Met-SEQ-tag,
(XVI) Met-SEQ,
(XVII) SEQ-tag,
(XVIII) Met-tag-SEQ,
(XIX) tag-SEQ,
(XX) tag-SEQ-tag,
(XXI) SEQ wherein Met is an N-terminal methionine residue, SEQ is an amino acid sequence selected from the group consisting of SEQ ID NOs:22, 23, 24, 25, 36 and 37, and tag is a tag sequence (e.g. $(His)_6$). The tag sequence usually is 5 to 10 amino acids in length.

The polypeptide may consist of an amino acid sequence selected from the group consisting of SEQ ID NOs:39, 40, 41, 42, 53 and 54. The constructs B, C, D, E, P and Q consist of these amino acid sequences, respectively (see Examples). These embodiments correspond to structure (VIII) or (XV) above.

All embodiments described above in connection with the method of the invention are applicable to the hypoallergenic polypeptide of the invention and vice versa.

Further Aspects of the Invention

The invention further concerns a polynucleotide encoding the polypeptide of the present invention.

Due to the degeneracy of the genetic code many different polynucleotide molecules may encode a single polypeptide. The polynucleotide of the invention preferably is an expression construct for obtaining the polypeptide after expression in host cells. The expression construct may further comprise components which are generally known in the art such as promoter sequences, genes encoding resistance factors against antibiotics, a replication origin and the like.

The invention further concerns a cell transfected or transformed with a polynucleotide of the present invention. Suitable cells include eukaryotic cells and prokaryotic cells. Eukaryotic cells may be transfected by methods known in the art such as calcium phosphate mediated transfection, electroporation, lipofection etc.

The invention further relates to a pharmaceutical composition containing the polypeptide, polynucleotide or cell according to this invention. The pharmaceutical composition may further contain one or more pharmaceutically acceptable carrier(s) or diluents(s) such as a buffer or salt solution. Preferably the pharmaceutical composition of the invention is a vaccine composition. In a particular embodiment the pharmaceutical composition further contains an adjuvant such as aluminium hydroxide.

The invention also relates to a method for the preparation of the polypeptide of the invention. The method comprises providing a polynucleotide encoding the polypeptide, introducing said polynucleotide into a host cell, culturing the host cell thus obtained under conditions such that the hybrid polypeptide is expressed, in recovering the expression product from the cell. The polynucleotide may be prepared by methods known in the art. It may be preferred that PCR technology is used to prepare the polynucleotide encoding the polypeptide of the invention. The cDNA sequences of the grass pollen allergens Phl p 1, 2, 3, 4, 5, 6, 7, 11, 12, and 13 are shown in SEQ ID NO:11 to 20, respectively. Based on these sequences and on the disclosure in the present application, the skilled person can easily design suitable nucleic acids encoding polypeptides of the invention.

The invention further relates to the use of the polypeptide, a polynucleotide or a cell described herein for the preparation of a medicament for the treatment and/or prevention of an allergic disorder. Such a medicament may be composed of the polynucleotide encoding a vaccine which can be used directly for the DNA-based vaccination against Type 1 allergy. The recombinant or synthetic polypeptide may be used to prepare formulations for the oral, sublingual or parenteral treatment of Type 1 allergic disorders as they are now routinely used for immunotherapy. Examples of formulations for sublingual immunotherapy or adjuvant bound hybrid polypeptide for injection immunotherapy. Possible applications include also cell-based forms of immunotherapy which may be based on e.g. dendritic cells or other antigen presenting cells. Those cells are transformed and expressed to antigen in vivo. Preferably orthologous cells transformed with suitable vectors are used.

One mode of application may be the subcutaneous injection of adjuvant-bound polypeptide. Another possibility is oral or nasal administration of the polypeptide in order to induce immunological tolerance or anergy against the components of the polypeptide. All the possible formulations can be prepared according to measures which are known to those of skill in the art (dosage adjuvants scheme of administration).

The invention further relates to the use of the polypeptide described herein or of a polypeptide or a cell described herein for the preparation of a medicament for prophylactic vaccination or tolerance induction. Prophylactic administration of hybrid polypeptides means the administration of the polypeptide to individuals, preferably children who do not yet suffer from Type 1 allergy in order to induce a state of immunological tolerance, anergy or non-responsiveness, or a protective immunity against the components of the hybrid vaccine. This may be achieved by the various protocols outlined for treatment of an established allergic disorder. The prophylactic treatment may be performed with the polypeptides or polynucleotides described herein above.

In a further embodiment the invention relates to the use of a polypeptide described herein for the detection of antibodies against an allergenic protein in a sample. The antibody may be an IgM IgE, IgG or IgA antibody. The concentration of the antibody may be determined from a sample which has been obtained from a body fluid. The sample may be derived from animals or humans. Such tests may rely on a solid phase immobilized polypeptide or the polypeptide in the fluid phase. Examples for such tests include ELISA tests, Western blotting tests or any other tests where the polypeptide is immobilized to bind to specific antibodies out from the sample. Alternatively the polypeptide is added directly to the antibody containing fluid in order to adsorb specific antibodies as, e.g., in competitive immunological assays.

The polypeptide of the invention may also be used for cellular tests such as a T cell proliferation test, etc.

Summary of the amino acid and nucleotide sequences shown in the sequence listing:

| SEQ ID NO: | sequence/construct |
|---|---|
| 1 | Phl p 1 amino acid sequence |
| 2 | Phl p 2 amino acid sequence |
| 3 | Phl p 3 amino acid sequence |
| 4 | Phl p 4 amino acid sequence |
| 5 | Phl p 5 amino acid sequence |
| 6 | Phl p 6 amino acid sequence |
| 7 | Phl p 7 amino acid sequence |
| 8 | Phl p 11 amino acid sequence |
| 9 | Phl p 12 amino acid sequence |
| 10 | Phl p 13 amino acid sequence |
| 11 | Phl p 1 cDNA |
| 12 | Phl p 2 cDNA |
| 13 | Phl p 3 cDNA |
| 14 | Phl p 4 cDNA |
| 15 | Phl p 5 cDNA |
| 16 | Phl p 6 cDNA |
| 17 | Phl p 7 cDNA |
| 18 | Phl p 11 cDNA |
| 19 | Phl p 12 cDNA |
| 20 | Phl p 13 cDNA |
| 21 | construct A without N-terminal Met and C-terminal (His)$_6$ |
| 22 | construct B without N-terminal Met and C-terminal (His)$_6$ |
| 23 | construct C without N-terminal Met and C-terminal (His)$_6$ |
| 24 | construct D without N-terminal Met and C-terminal (His)$_6$ |
| 25 | construct E without N-terminal Met and C-terminal (His)$_6$ |
| 26 | construct F without N-terminal Met and C-terminal (His)$_6$ |
| 27 | construct G without N-terminal Met and C-terminal (His)$_6$ |
| 28 | construct H without N-terminal Met and C-terminal (His)$_6$ |
| 29 | construct I without N-terminal Met and C-terminal (His)$_6$ |
| 30 | construct J without N-terminal Met and C-terminal (His)$_6$ |
| 31 | construct K without N-terminal Met and C-terminal (His)$_6$ |
| 32 | construct L without N-terminal Met and C-terminal (His)$_6$ |
| 33 | construct M without N-terminal Met and C-terminal (His)$_6$ |
| 34 | construct N without N-terminal Met and C-terminal (His)$_6$ |
| 35 | construct O without N-terminal Met and C-terminal (His)$_6$ |
| 36 | construct P without N-terminal Met and C-terminal (His)$_6$ |
| 37 | construct Q without N-terminal Met and C-terminal (His)$_6$ |
| 38 | construct A with N-terminal Met and C-terminal (His)$_6$ |
| 39 | construct B with N-terminal Met and C-terminal (His)$_6$ |
| 40 | construct C with N-terminal Met and C-terminal (His)$_6$ |
| 41 | construct D with N-terminal Met and C-terminal (His)$_6$ |
| 42 | construct E with N-terminal Met and C-terminal (His)$_6$ |
| 43 | construct F with N-terminal Met and C-terminal (His)$_6$ |
| 44 | construct G with N-terminal Met and C-terminal (His)$_6$ |
| 45 | construct H with N-terminal Met and C-terminal (His)$_6$ |
| 46 | construct I with N-terminal Met and C-terminal (His)$_6$ |
| 47 | construct J with N-terminal Met and C-terminal (His)$_6$ |
| 48 | construct K with N-terminal Met and C-terminal (His)$_6$ |
| 49 | construct L with N-terminal Met and C-terminal (His)$_6$ |
| 50 | construct M with N-terminal Met and C-terminal (His)$_6$ |
| 51 | construct N with N-terminal Met and C-terminal (His)$_6$ |
| 52 | construct O with N-terminal Met and C-terminal (His)$_6$ |
| 53 | construct P with N-terminal Met and C-terminal (His)$_6$ |
| 54 | construct Q with N-terminal Met and C-terminal (His)$_6$ |
| 55 | P1a |
| 56 | P1b |
| 57 | P1c |
| 58 | P1d |
| 59 | P1a1 |
| 60 | P1a2 |
| 61 | P1c1 |
| 62 | P1c2 |
| 63 | P2A |
| 64 | P2B |
| 65 | P2a |
| 66 | P2b |
| 67 | P2c |
| 68 | P2a1 |
| 69 | P2b2 |
| 70 | P5a |
| 71 | P5b |
| 72 | P5c |
| 73 | P5d |
| 74 | P5c1 |
| 75 | P5c2 |
| 76 | P6b |

The amino acid sequences SEQ ID NO:1-10 show the mature peptides lacking the signal peptide, where applicable.

The following examples further illustrate the invention. The scope of the invention, however, is not limited to the examples.

EXAMPLES

In this study we demonstrate that these approaches can be combined and extended for a complex allergen source like grass pollen. We constructed a vaccine based on the four major allergens from timothy grass (Phl p 1, Phl p 2, Phl p 5, Phl p 6) for the treatment of grass pollen allergy (13, 14). Referring to structural data and epitope mapping studies the allergens were split into fragments with reduced allergenic activity. We describe the production of different combinations of these fragments as hybrid proteins, their biochemical and immunological properties and how four hybrid proteins were selected as candidate molecules for vaccination against grass pollen allergy.

Example 1

Design, Expression, and Purification of the Hybrid Molecules

Figure 2:
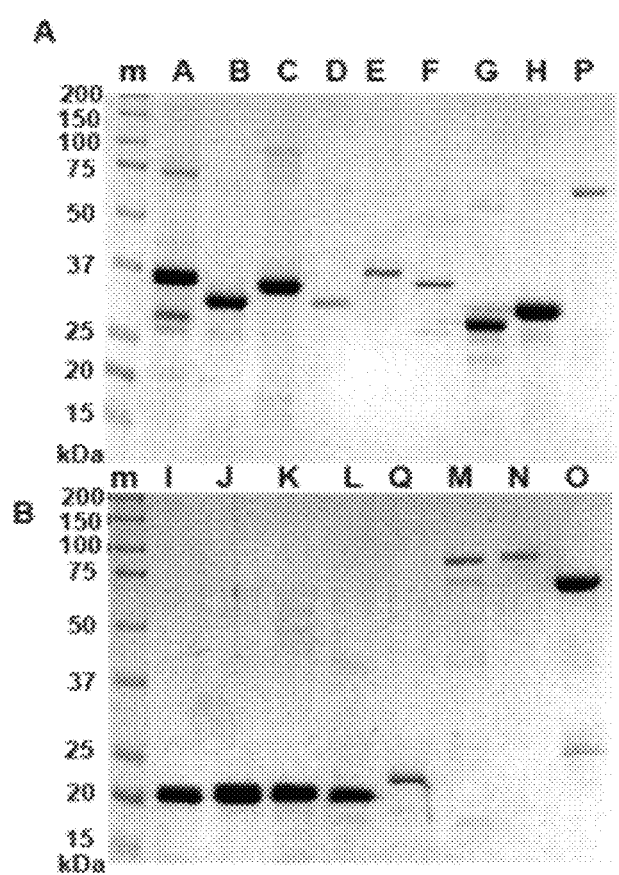
FIG. 2 shows a Coomassie-stained PAA-Gel containing the purified hybrid proteins A-Q (see Example 1). Molecular weights are indicated on the left margin (m, molecular weight marker).
Figure 3:
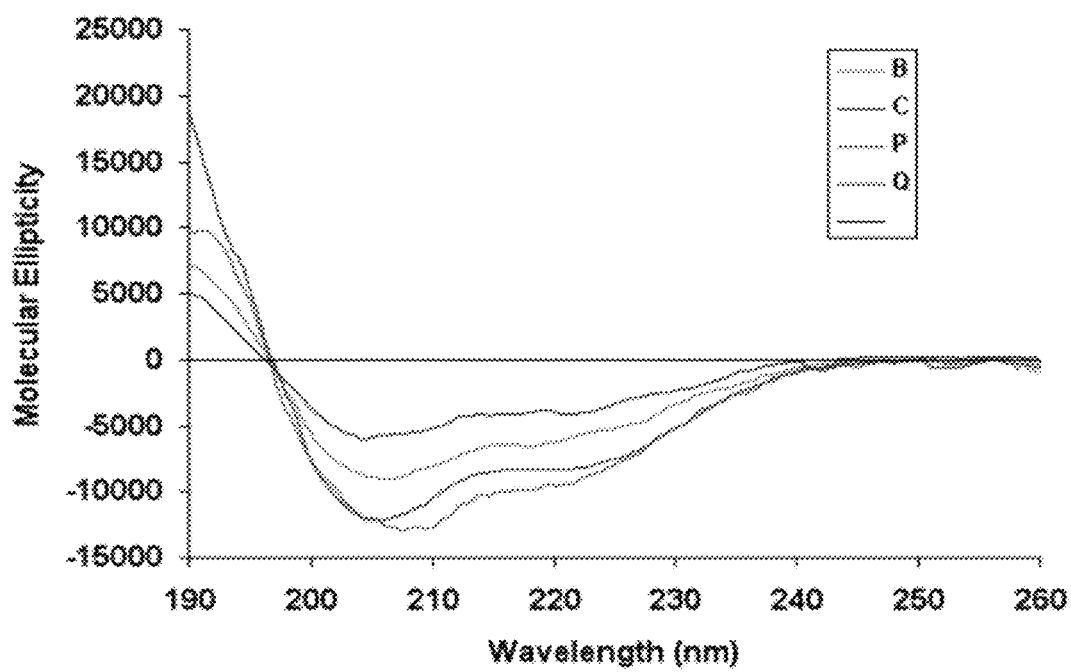
FIG. 3 shows far UV CD spectra of the proteins B, C, P, and Q dissolved in water were collected on a Jasco J-810 spectropolarimeter (Japan Spectroscopic Co., Tokyo, Japan), see Example 2.

For construction of hypoallergenic hybrid molecules seventeen different hybrid molecules were designed by the assembly of allergen fragments derived from the major timothy grass pollen allergens Phl p 1, Phl p 2, Phl p 5, and Phl p 6 as shown in FIG. 1. The amino acid sequences of the resulting proteins (designated A-Q) are listed in Table 1. P1M and P2M refer to previously designed allergen derivatives (References 15, 16). All sequences were codon-optimized for expression in *Escherichia coli*, a start-codon (ATG) was added at the 5' end and a 6×Histidine tag was added at the 3'end of each sequence, followed by a stop-codon. The resulting genes encoding the hybrid molecules A-Q were cloned into the expression vector pET17b (Novagen) and expressed in liquid culture in *Eschericha coli* BL21 (DE3) cells (Stratagene). All proteins were purified by affinity chromatography using a standard protocol (Qiagen). The purity of the expressed hybrid molecules was analyzed by SDS-PAGE. (FIG. 2)

TABLE I

Amino acid sequences of Phl p 1-, Phl p 2-, Phl p 5-, and Phl p 6-derived fragments.

Phl p 1-derived fragments

P1a  IPKVPPGPNITATYGDKWLDAKSTWYGKPTGAGPKDNGGACGYKDVDKPPFSGMTGCGNTPIFK
     (SEQ ID: 55)

TABLE I-continued

Amino acid sequences of Phl p 1-, Phl p 2-, Phl p 5-, and Phl p 6-derived fragments.

```
P1b   SGRGCGSCFFIKCTKPEACSGEPVVVHTTDDNEEPIAPYHFDLSGHAFGAMAKKGDEQKLR (SEQ ID: 56)

P1c   SAGELELQFRRVKCKYPEGTKVTFHVEKGSNPNYLALLVKYVNGDGDVVAVDIKEKGKDKWIELKESWGAIWRIDTPDKL
      (SEQ ID: 57)

P1d   TGPFTVRYTTEGGTKTEAEDVIPEGWKADTSYESK (SEQ ID: 58)

P1a1  IPKVPPGPNTTATYGDKWLDAKSTWYGKPTGA (SEQ ID: 59)

P1a2  GPKDNGGACGYKDVDKPPFSGMTGCGNTPIFK (SEQ ID: 60)

P1c1  SAGELELQFRRVKCKYPEGTKVTFHVEKGSNPNYLALLV (SEQ ID: 61)

P1c2  KYVNGDGDVVAVDIKEKGKDKWIELKESWGAIWRIDTPDKL (SEQ ID: 62)

Phl p 5-derived fragments

P5a   ADLGYGPATPAAPAAGYTPATPAAPAEAAPAGKATTEEQKLIEKINAGFKAALAAAAGVQPADKYRTFVATF
      (SEQ ID: 70)

P5b   GAASNKAFAEGLSGEPKGAAESSSKAALTSKLDAAYKLAYKTAEGATPEAKYDAYVATLSEALRIIAGTLEVHAVKPA
      (SEQ ID: 71)

P5c   AEEVKVIPAGELQVIEKVDAAFKVAATAANAAPANDKFTVFEAAFNDAIKASTGGAYESYKFTPALEA
      (SEQ ID: 72)

P5d   AVKQAYAATVATAPEVKYTVFETALKKAITAMSEAQKAAKPAAAATATATAAVGAATGAATAATGGYKV
      (SEQ ID: 73)

P5c1  AEEVKVIPAGELQVIEKVDAAFKVAATAANAAPA (SEQ ID: 74)

P5c2  NDKFTVFEAAFNDAIKASTGGAYESYKFIPALEA (SEQ ID: 75)

Phl p 2-derived fragments

P2A   VPKVTFTVEKGSNEKHLAVLVKYEGDTMAEVELREHGSDEWVAMTKGEG (SEQ ID: 63)

P2B   GVWTEDSEEPLQGPFNERFLTEKGMKNVFDDVVPEKYTIGATYAPEE (SEQ ID: 64)

P2a   VPKVTFTVEKGSNEKHLAVLVKYEGDTMAEVEL (SEQ ID: 65)

P2b   REHGSDEWVAMTKGEGGVWTFDSEEPLQGPFN (SEQ ID: 66)

P2c   FRFLTEKGMKNVFDDVVPEKYTIGATYAPEE (SEQ ID: 67)

P2a1  VPKVTFTVEKGSNEKHLAVLVKYEGDTMAEVELREHGS (SEQ ID: 68)

P2b2  DEWVAMTKGEGGVWTFDSEEPLQGPFN (SEQ ID: 69)

Phl p 6-derived fragment

P6b   ADKYKTFEAAFTVSSKRNLADAVSKAPQLVPKLDEVYNAAYNAADHAAPEDKYEAFVLHFSEALRIIAGTPEVHAVKPGA
      (SEQ ID: 75)
```

Example 2

Secondary Structure Estimation of the Hybrid Molecules

To evaluate the secondary structure of hybrid molecules far UV CD spectra of the proteins B, C, P, and Q dissolved in water were collected on a Jasco J-810 spectropolarimeter (Japan Spectroscopic Co., Tokyo, Japan) as described (16). All hybrid proteins, which were analyzed regarding their secondary structure, exhibited a random coiled structure, which has been observed previously for several other allergen derivatives (18, 19).

Example 3

IgE-Reactivity of the Hybrid Molecules

To analyze the IgE reactivity of hybrid molecules the direct binding of serum IgE from grass pollen allergic patients to the Phl p 1, Phl p 2, Phl p 5-, and Phl p 6-derived hybrid molecules A-Q, or rPhl p 1, rPhl p 2, rPhl p 5, and rPhl p 6, or HSA as negative control, was investigated by non-denaturing dot blot experiments as described (18, 19). Patients' IgE antibodies bound to the recombinant 'wildtype' allergens Phl p 1, Phl p 2, Phl p 5, and Phl p 6, but not to the control protein HSA. Unexpectedly, we observed different IgE-reactivities of allergic patients' IgE to the hybrid molecules A-Q, which could not be explained by the primary structure (e.g. hybrids A and C, and hybrids E and F contain exactly the same allergen-derived fragments).

Example 4

Reduced Allergenic Activity of the Hybrid Molecules B, C, P, and Q

Figure 5:
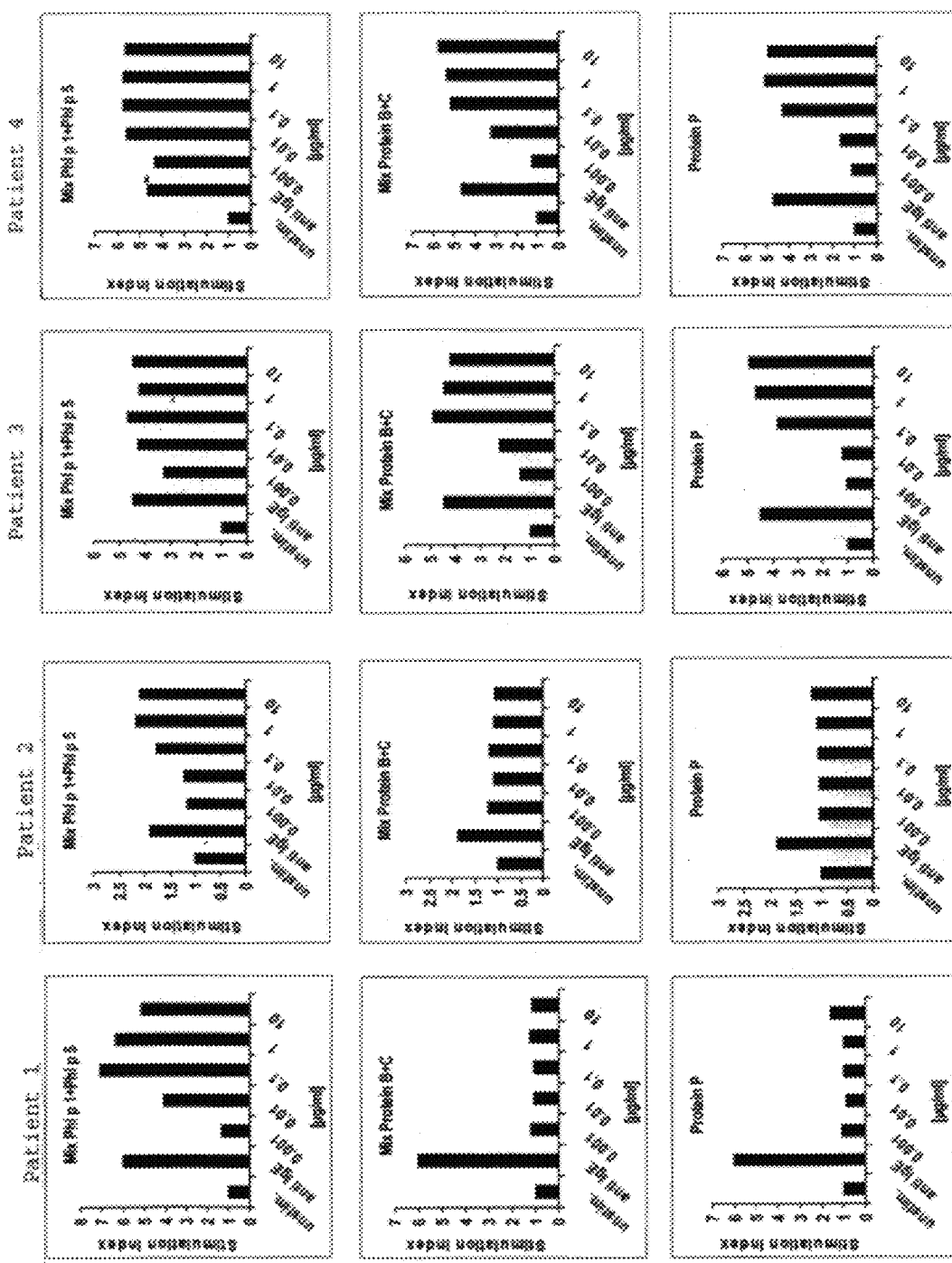
FIG. 5 depicts reduced allergenic reactivity of hybrids in comparison to the wild-type allergens as detected by CD203c expression (see Example 4).
Figure 5:
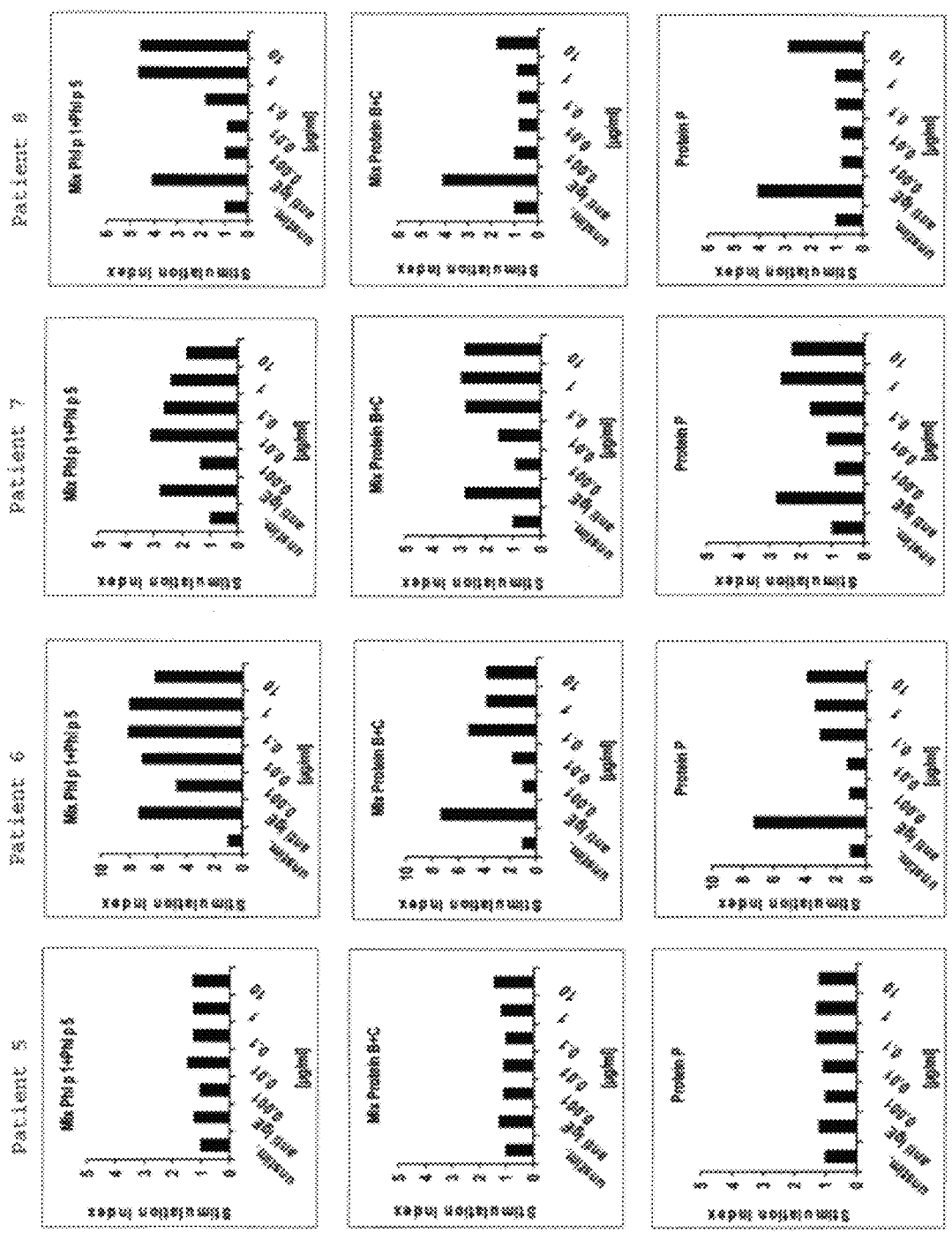
Figure 5:
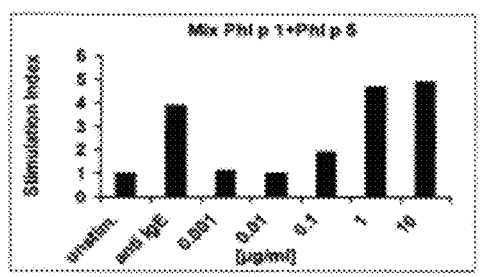
Figure 5:
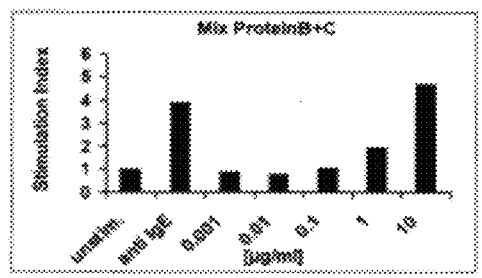
Figure 5:
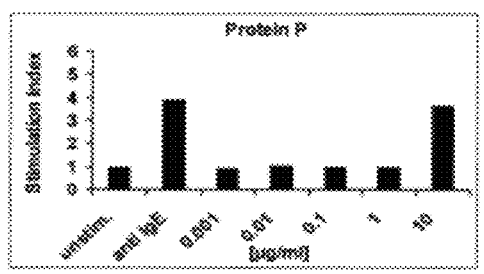
Figure 5:
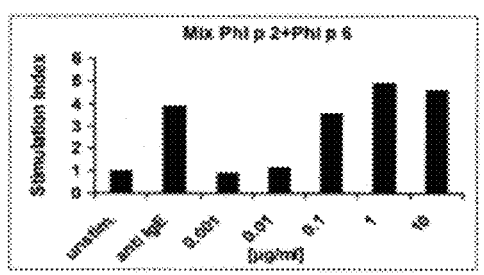
Figure 5:
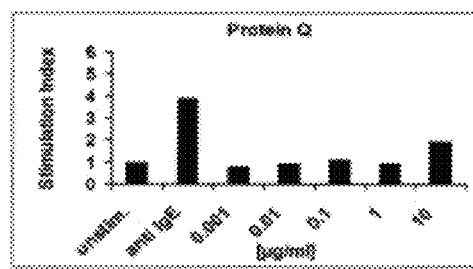
Figure 5:
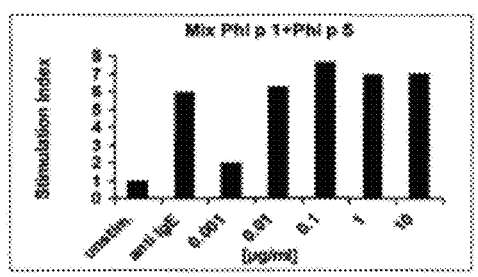
Figure 5:
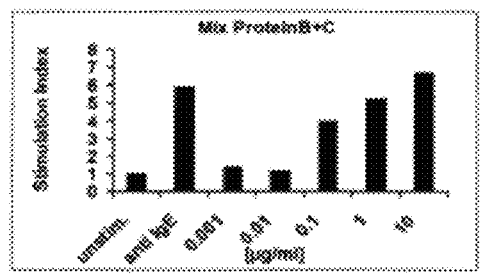
Figure 5:
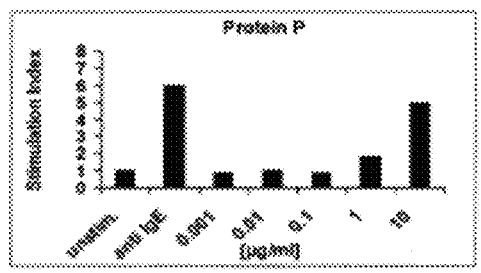
Figure 5:
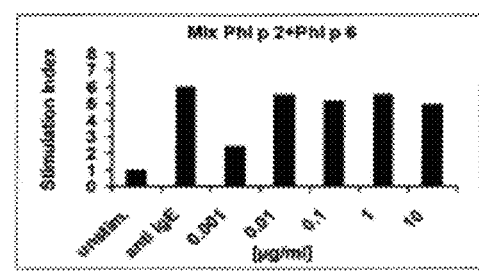
Figure 5:
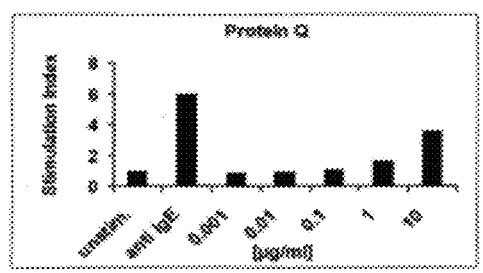
Figure 5:
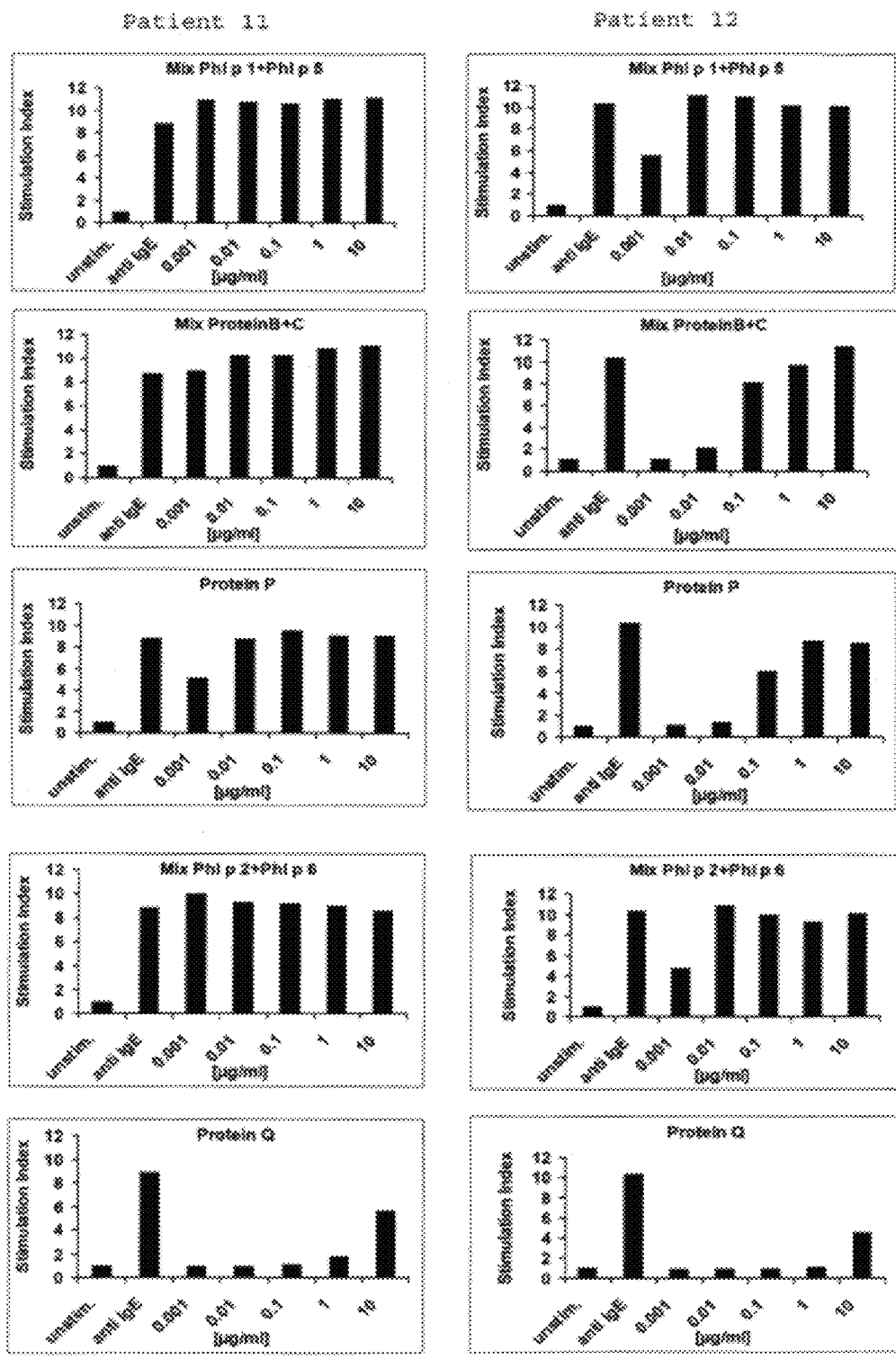

Four hybrid molecules, B, C, P, and Q were selected for further analysis. To determine the IgE-reactivity of the hybrids B, C, P, and Q on IgE-dependent effector cell activation CD203c expression on human basophils isolated from grass pollen allergic patients was analyzed. CD203c has previously been described as an activation marker on human basophils, which is upregulated upon allergen-induced cross-linking of receptor-bound IgE (20). As shown in FIG. 5, the cells tolerated an at least 10 fold higher concentration of the hybrid molecules compared to the equimolar amount of the wildtype allergens (Patients 1-12). These data suggest a strongly reduced allergenic activity of the four hybrid molecules B, C, P, and Q.

Example 5

T Cell Proliferations

To evaluate the T cell reactivity of hybrid molecules in vitro proliferation experiments with PBMC isolated from four grass pollen allergic patients were performed as described (16). Although the allergenic activity of the hybrid molecules was reduced, most of the T cell epitopes of the wildtype Phl p 1, Phl p 2, Phl p 5, and Phl p 6 allergens were preserved. (Table II).

TABLE II

PBMC from grass pollen allergic patients respond to the hybrid molecules

|  | 20 µg/ml | 10 µg/ml | 5 µg/ml | 2.5 µg/ml | 1.25 µg/ml |
|---|---|---|---|---|---|
| rPhl p 1 + | 2.5 | 2.6 | 2.0 | 1.3 | 1.6 |
| rPhl p 5 | (±1.5) | (±1.8) | (±1.1) | (±0.1) | (±0.7) |
| B + C | 1.7 | 2.1 | 2.2 | 2.0 | 1.4 |
|  | (±1.1) | (±1.5) | (±1.4) | (±0.9) | (±0.5) |
| P | 2.0 | 2.2 | 2.0 | 2.7 | 2.5 |
|  | (±1.5) | (±1.4) | (±0.6) | (±1.2) | (±1.2) |
| rPhl p 2 + | 1.6 | 1.3 | 1.5 | 1.3 | 1.5 |
| rPhl p 6 | (±0.9) | (±0.69) | (±0.6) | (±0.7) | (±0.4) |
| Q | 1.4 | 1.6 | 2.0 | 2.9 | 2.8 |
|  | (±1.0) | (±0.8) | (±0.5) | (±1.0) | (±0.7) |

Example 6

Figure 6:
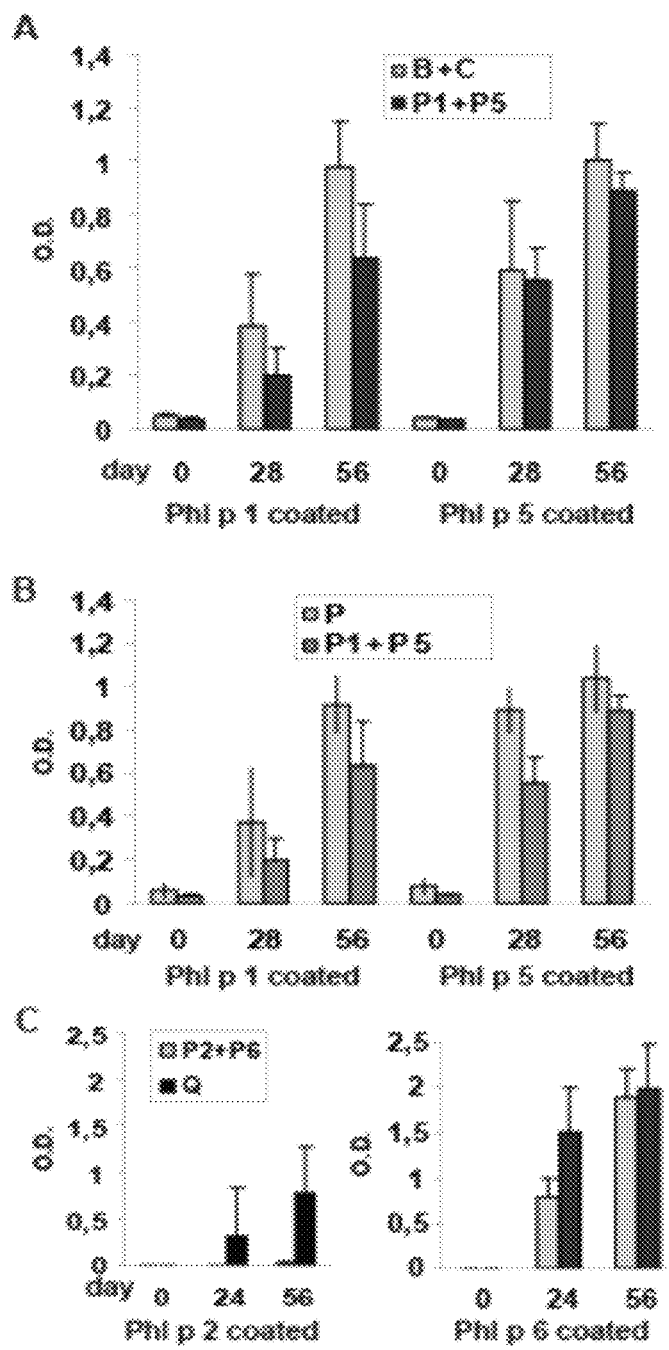
FIG. 6 depicts IgG reactivity after immunization of mice with a mixture of Phl p1 and Phl p 5, or a mixture of Phl p 2 and Phl p 6, or a mixture of B and C, or P, or Q. The development of Phl p1-, Phl p 2-, Phl p 5-, and Phl p 6-specific $IgG_1$ antibody levels was compared by ELISA measurements (see Example 6).

Immunization with the Hybrid Molecules B, C, P, and Q Induced an IgG Response Directed Against the Wildtype Allergens To investigate whether IgG antibodies induced by immunization with B, C, P, or Q were able to recognize the rPhl p 1, rPhl p 2, rPhl p 5, and rPhl p 6 wildtype allergens two different animal models (BALB/c mice, rabbits) were used. We immunized BALB/c mice with a mixture of Phl p1 and Phl p 5, or a mixture of Phl p 2 and Phl p 6, or a mixture of B and C, or P, or Q, and compared the development of Phl p1-, Phl p 2-, Phl p 5-, and Phl p 6-specific IgG$_1$ antibody levels by ELISA measurements (FIG. 6). The hybrids B+C, as well as P and Q were able to induce a Phl p 1, Phl p 2, Phl p 5, and Phl p 6-specific IgG$_1$ antibody response, which were higher than the antibody response induced by the wildtype allergens themselves.

Figure 7:
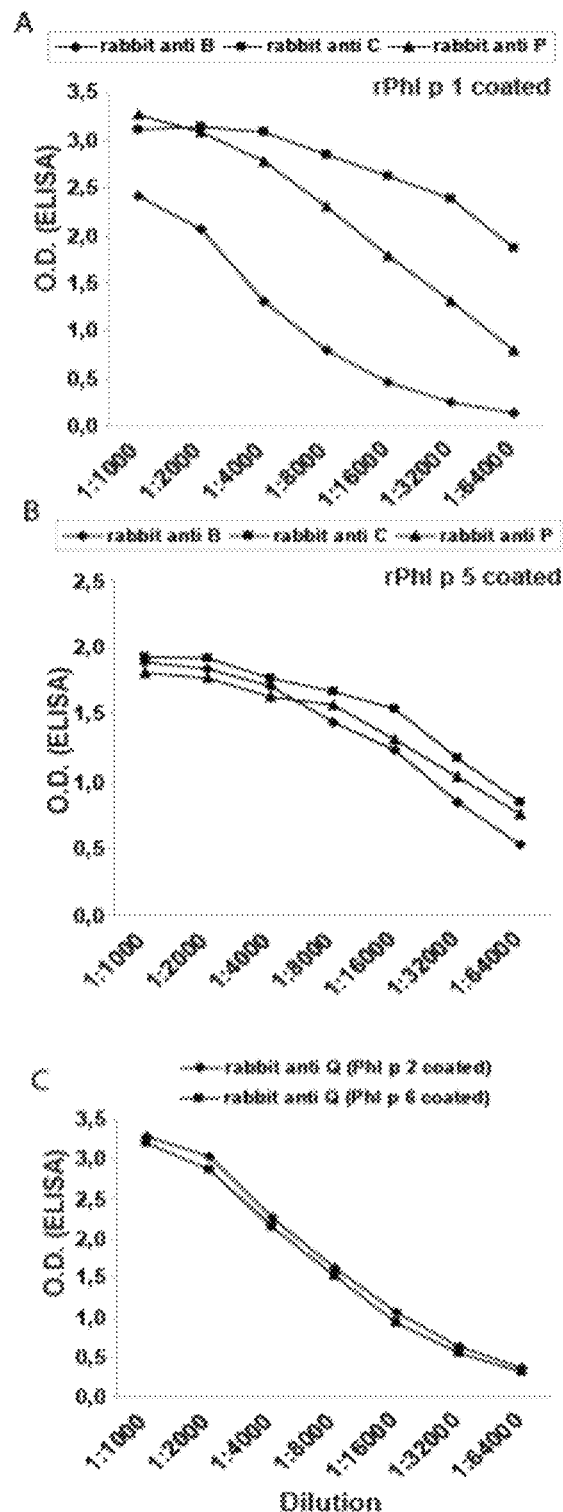
FIG. 7 shows results from Example 7. The figure depicts IgG reactivity after immunization of rabbits with B, C, P, or Q, namely IgG antibody responses to the wild-type allergens Phl p 1 (FIG. 7A), Phl p 5 (FIG. 7B), Phl p 2, and Phl p 6 (FIG. 7C).

The development of allergen-specific IgG antibody responses was also investigated by immunization of rabbits with B, C, P, or Q. Serial dilutions of rabbit antisera were tested for Phl p 1-Phl p 2- Phl p 5- and Phl p 6-specific IgG antibodies by ELISA. The constructs B, C, P, and Q were able to induce an IgG antibody response to the wildtype allergens Phl p 1 (FIG. 7A), Phl p 5 (FIG. 7B), Phl p 2, and Phl p 6 (FIG. 7C).

Example 7

Immunization with the Hybrid Allergens B, C, P, and Q Induced a Protective IgG Response Blocking Allergic Patients' IgE Binding to the Wild-Type Allergens and Grass Pollen Extract To examine the ability of IgG antibodies induced with the hybrid molecules B, C, P, and Q to inhibit grass pollen allergic patients' IgE binding to rPhl p 1, Phl p 2, Phl p 5, and rPhl p 6, or to a natural grass pollen extract. In ELISA inhibition experiments we therefore preincubated an ELISA plate-bound natural grass pollen extract with a mixture of rabbit anti-P and Q antiserum, or a mixture of anti-B, C, and Q antiserum, or a rabbit antiserum obtained by immunization with a previously described grass pollen hybrid (GPH) (11) consisting of Phl p 1, Phl p 2, Phl p 5, and Phl p 6 or the corresponding preimmunesera. These rabbit IgG antibodies could inhibit IgE binding of 14 grass pollen allergic patients to the grass pollen extract as follows: P+Q: 73%; B+C+Q: 78%; GPH: 75% (Table III). Similar experiments were performed with ELISA plate-bound rPhl p 1, rPhl p 2, rPhl p 5, and Phl p 6, leading to an average inhibition of 81-94% for Phl p 1 (Table IV), 86-90% for Phl p 5 (Table V), 45% for Phl p 2 (Table VI), and 34% for Phl p 6 (Table VII).

TABLE III

% Inhibition of patients' IgE binding to GPE after preincubation with rabbit antisera

| patient | P + Q | B + C + Q | GPH |
|---|---|---|---|
| 1 | 90 | 93 | 92 |
| 2 | 28 | 23 | 14 |
| 3 | 84 | 89 | 87 |
| 4 | 75 | 81 | 78 |
| 5 | 61 | 71 | 70 |
| 6 | 78 | 84 | 86 |
| 7 | 81 | 86 | 86 |
| 8 | 80 | 80 | 80 |
| 9 | 76 | 83 | 73 |
| 10 | 66 | 71 | 75 |
| 11 | 76 | 87 | 86 |
| 12 | 70 | 80 | 72 |
| 13 | 72 | 81 | 75 |
| 14 | 84 | 89 | 82 |
| mean | 73 | 78 | 75 |
| SD | 15.0 | 17.1 | 18.9 |

TABLE IV

% inhibition of patients' IgE binding to rPhl p 1 after preincubation with rabbit antisera

| patient | B + C | B | C | P | GPH |
|---|---|---|---|---|---|
| 1 | 84 | 86 | 91 | 90 | 66 |
| 2 | 97 | 82 | 97 | 94 | 46 |
| 3 | 92 | 77 | 93 | 90 | 44 |
| 4 | 73 | 69 | 79 | 76 | 47 |
| 5 | 90 | 86 | 91 | 89 | 57 |

TABLE IV-continued

% inhibition of patients' IgE binding to rPhl p 1
after preincubation with rabbit antisera

| patient | B + C | B | C | P | GPH |
|---|---|---|---|---|---|
| 6 | 94 | 80 | 96 | 92 | 43 |
| 7 | 93 | 81 | 98 | 96 | 44 |
| 8 | 98 | 93 | 100 | 99 | 67 |
| 9 | 96 | 82 | 98 | 92 | 44 |
| 10 | 98 | 78 | 99 | 94 | 44 |
| mean | 92 | 81 | 94 | 91 | 50 |
| SD | 7.8 | 6.4 | 6.2 | 6.1 | 9.5 |

TABLE V

% Inhibition of patients' IgE binding to rPhl p 5
after preincubation with rabbit antisera

| patient | B + C | B | C | P | GPH |
|---|---|---|---|---|---|
| 1 | 92 | 93 | 94 | 94 | 94 |
| 2 | 93 | 91 | 90 | 95 | 97 |
| 3 | 92 | 86 | 90 | 92 | 93 |
| 4 | 86 | 82 | 86 | 89 | 89 |
| 5 | 87 | 83 | 90 | 91 | 92 |
| 6 | 93 | 88 | 91 | 94 | 96 |
| 7 | 95 | 91 | 95 | 96 | 98 |
| 8 | 95 | 92 | 94 | 97 | 98 |
| 9 | 68 | 63 | 66 | 52 | 52 |
| 10 | 95 | 90 | 92 | 97 | 99 |
| mean | 90 | 86 | 89 | 90 | 91 |
| SD | 8.2 | 8.9 | 8.4 | 13.5 | 14.0 |

TABLE VI

% Inhibition of patients' IgE binding to
rPhl p 2 after preincubation with rabbit antisera

| patient | Q | GPH |
|---|---|---|
| 1 | 52 | 86 |
| 2 | 50 | 87 |
| 3 | 41 | 71 |
| 4 | 60 | 76 |
| 5 | 46 | 83 |
| 6 | 43 | 74 |
| 7 | 47 | 60 |
| 8 | 31 | 45 |
| 9 | 36 | 54 |
| mean | 45 | 71 |
| SD | 8.7 | 14.8 |

TABLE VII

% Inhibition of patients' IgE binding to
rPhl p 6 after preincubation with rabbit antisera

| patient | Q | GPH |
|---|---|---|
| 1 | 38 | 55 |
| 2 | 38 | 53 |
| 3 | 36 | 52 |
| 4 | 29 | 47 |
| 5 | 32 | 46 |
| 6 | 40 | 51 |
| 7 | 32 | 38 |
| 8 | 41 | 59 |
| 9 | 23 | 32 |
| mean | 34 | 48 |
| SD | 5.9 | 8.5 |

Example 8

Immunization with the Hybrid Molecules B, C, and P Induced an IgG Response Directed Against the Wildtype Allergen Phl p 1

Figure 8:
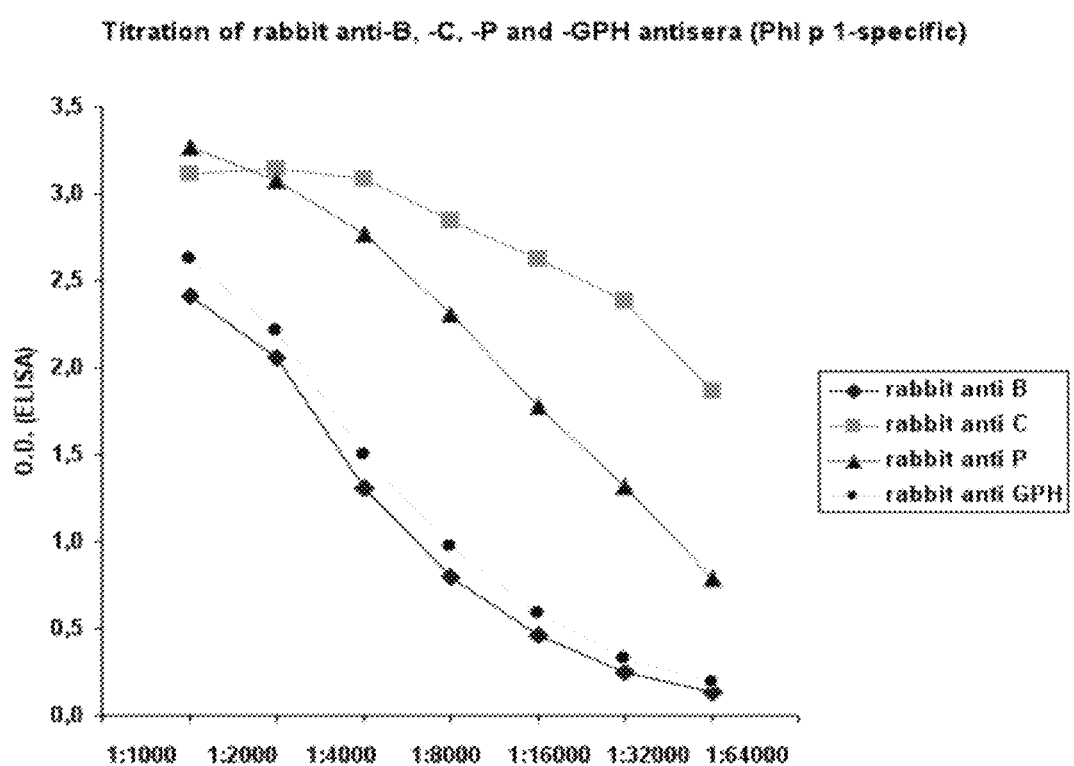
FIG. 8 depicts IgG reactivity after immunization of rabbits with B, C, P, or GPH (a grass pollen allergen-derived hybrid described in Ref. 11) namely IgG antibody responses to the wildtype allergen Phl p 1 (see Example 8).

Serial dilutions of rabbit antisera were tested for Phl p 1-specific IgG antibodies by ELISA. The constructs B, C, and P, were able to induce an IgG antibody response to the wildtype allergen Phl p 1. The IgG response was compared to IgG antibody levels induced by immunization with a hybrid molecule consisting of the wildtype allergens Phl p 1, Phl p 2, Phl p 5, and Phl p 6 (grass pollen hybrid, GPH), which has previously been described as a highly immunogenic molecule (11). Unexpectedly, C and P induced even higher levels of Phl p 1-specific IgG antibodies in rabbits. The results are shown in FIG. 8.

REFERENCES

1. Kay A B., Kaplan A P, Bousquet J, Holt P J. Allergy and Allergic Diseases. Blackwell Scientific Publ./Oxford, United Kingdom; 2008.
2. Bischoff S C. *Role of mast cells in allergic and non-allergic immune responses: comparison of human and murine data*. Nat Rev Immunol. 2007.7:93-104.
3. van Nerveen, R. J., Knol, E. F., Ejrnaes, A., Wurtzen, P. A. IgE-mediated allergen presentation and blocking antibodies: regulation of T-cell activation in allergy. Int. Arch. Allergy Immunol. 2006. 141: 119.
4. Bieber T. *Fc epsilon RI on human epidermal Langerhans cells: an old receptor with new structure and functions*. Int Arch Allergy Immunol. 1997.113:30-4.
5. Valenta, R. and Niederberger, V. (2007). Recombinant allergens for immunotherapy. J. Allergy Clin. Immunol. 119, 826-830.
6. Focke M, Marth K, Flicker S, Valenta R. Heterogeneity of commercial timothy grass pollen extracts. Clin Exp Allergy. 2008, 38:1400-8.
7. Mothes, N., Heinzkill, M., Drachenberg, K. J., Sperr, W. R., Krauth, M. T., Majlesi, Y., Semper, H., Valent, P., Niederberger, V., Kraft, D., and Valenta, R. (2003). Allergen-specific immunotherapy with a monophosphoryl lipid A-adjuvanted vaccine: reduced seasonally boosted immunoglobulin E production and inhibition of basophil histamine release by therapy-induced blocking antibodies. Clin. Exp. Allergy 33, 1198-1208.
8. Linhart B., and Valenta, R. (2005). Molecular design of allergy vaccines. Curr. Opin. Immunol. 17, 646-655.
9. Niederberger, V., Horak, F., Vrtala, S., Spitzauer, S., Krauth, M. T., Valent, P., Reisinger, J., Pelzmann, M., Hayek, B., Kronqvist, M., Gafvelin, G., Gronlund, H., Purohit, A., Suck, R., Fiebig, H., Cromwell, O., Pauli, G., van Hage-Hamsten, M., and Valenta, R. (2004). Vaccination with genetically engineered allergens prevents progression of allergic disease. Proc. Natl. Acad. Sci. 101, 14677-14682.
10. Linhart, B., Jahn-Schmid, B., Verdino, P., Keller, W., Ebner, C., Kraft, D., and Valenta, R. (2002). Combination vaccines for the treatment of grass pollen allergy consisting of genetically engineered hybrid molecules with increased immunogenicity. FASEB J. 16, 1301-1303.
11. Linhart, B., Hartl, A., Jahn-Schmid, B., Verdino, P., Keller, W., Krauth, M. T., Valent, P., Horak, F., Wiedermann, U., Thalhammer, J., Ebner, C., Kraft, D., and Valenta, R. (2005). A hybrid molecule resembling the epitope spectrum of grass pollen for allergy vaccination. J. Allergy Clin. Immunol. 115, 1010-1016.
12. Linhart, B. and Valenta, R. (2004). Vaccine engineering improved by hybrid technology. Int. Arch. Allergy Immunol. 134, 324-331.
13. Vrtala S., Susani M., Sperr W. R., Valent P., Laffer S., Dolecek C., Kraft D., and Valenta R. (1996) Immunologic characterization of purified recombinant timothy grass pollen (*Phleum pratense*) allergens (Phl p 1, Phl p 2, Phl p 5). *J Allergy Clin. Immunol* 97, 781-787.
14. Vrtala S., Fischer S., Grote M., Vangelista L., Pastore A., Sperr W. R., Valent P., Reichelt R., Kraft D., and Valenta R. (1999) Molecular, immunological, and structural characterization of Phl p 6, a major allergen and P-particle-associated protein from timothy grass (*Phleum pratense*) pollen. *J. Immunol.* 163, 5489-5496
15. Mothes-Luksch, N., S. Stumvoll, B. Linhart, M. Focke, M. T. Krauth, A. Hauswirth, P. Valent, P. Verdino, T. Pavkov, W. Keller, M. Grote, R. Valenta. 2008. Disruption of allergenic activity of the major grass pollen allergen Phl p 2 by reassembly as a mosaic protein. *J. Immunol.* 181: 4864-73.
16. Ball, T., B. Linhart, K. Sonneck. Blatt, H. Hermann, P. Valent, A. Stoecklinger, C. Lupinek, J. Thalhamer, A. A. Fedorov, S. C. Almo, R. Valenta. 2009. Reducing allergenicity by altering allergen fold: A mosaic protein of Phl p 1 for allergy vaccination. *Allergy* 64:569-80.
17. Vrtala S., Focke M, Kopec J, Verdino P, Hartl A, Sperr W R, Fedorov A A, Ball T, Almo S, Valent P, Thalhamer J, Keller W, Valenta R. Genetic engineering of the major timothy grass pollen allergen, Phl p 6, to reduce allergenic activity and preserve immunogenicity. J. Immunol. 2007. 179: 1730-9
18. Vrtala, S., K. Hirtenlehner, L. Vangelista, A. Pastore, H.-G. Eichler, W. R. Sperr, P. Valent, C. Ebner, D. Kraft, R. Valenta. 1997. Conversion of the major birch pollen allergen, Bet v 1, into two nonanaphylactic T cell epitope-containing fragments. Candidates for a novel form of specific immunotherapy. *J. Clin. Invest.* 99: 1673-1681.
19. Swoboda I, Bugajska-Schretter A, Linhart B, Verdino P, Keller W, Schulmeister U, Sperr W R, Valent P, Peltre G, Quirce S, Douladiris N, Papadopoulos N G, Valenta R, Spitzauer S. A recombinant hypoallergenic parvalbumin mutant for immunotherapy of IgE-mediated fish allergy. J Immunol. 2007.178:6290-6.
20. Hauswirth A W, Natter S, Ghannadan M, Majlesi Y, Schernthaner G H, Sperr W R, Bühring H J, Valenta R, Valent P. J. Recombinant allergens promote expression of CD203c on basophils in sensitized individuals. Allergy Clin Immunol. 2002. 110:102-9.
21. Linhart, B., Mothes-Luksch, N., Vrtala, S., Kneidinger, M., Valent, P., and Valenta, R. 2008. A hypoallergenic hybrid molecule with increased immunogenicity consisting of derivatives of the major grass pollen allergens, Phl p 2 and Phl p 6. *Biol. Chem.* 389:925-33.

The invention claimed is:

1. A hypoallergenic polypeptide comprising an amino acid sequence selected from the group consisting of SEQ ID NOs: 22, 23, 24, 25, 36 and 37.

2. The hypoallergenic polypeptide according to claim 1, wherein said polypeptide consists of an amino acid sequence selected from the group consisting of SEQ ID NOs: 39, 40, 41, 42, 53 and 54.

* * * * *

SEQUENCE LISTING

```
<160> NUMBER OF SEQ ID NOS: 76

<210> SEQ ID NO 1
<211> LENGTH: 240
<212> TYPE: PRT
<213> ORGANISM: Phleum pratense

<400> SEQUENCE: 1

Ile Pro Lys Val Pro Pro Gly Pro Asn Ile Thr Ala Thr Tyr Gly Asp
1               5                   10                  15

Lys Trp Leu Asp Ala Lys Ser Thr Trp Tyr Gly Lys Pro Thr Gly Ala
            20                  25                  30

Gly Pro Lys Asp Asn Gly Gly Ala Cys Gly Tyr Lys Asp Val Asp Lys
        35                  40                  45

Pro Pro Phe Ser Gly Met Thr Gly Cys Gly Asn Thr Pro Ile Phe Lys
    50                  55                  60

Ser Gly Arg Gly Cys Gly Ser Cys Phe Glu Ile Lys Cys Thr Lys Pro
65                  70                  75                  80

Glu Ala Cys Ser Gly Glu Pro Val Val Val His Ile Thr Asp Asp Asn
                85                  90                  95

Glu Glu Pro Ile Ala Pro Tyr His Phe Asp Leu Ser Gly His Ala Phe
            100                 105                 110

Gly Ala Met Ala Lys Lys Gly Asp Glu Gln Lys Leu Arg Ser Ala Gly
        115                 120                 125

Glu Leu Glu Leu Gln Phe Arg Arg Val Lys Cys Lys Tyr Pro Glu Gly
    130                 135                 140

Thr Lys Val Thr Phe His Val Glu Lys Gly Ser Asn Pro Asn Tyr Leu
145                 150                 155                 160

Ala Leu Leu Val Lys Tyr Val Asn Gly Asp Gly Asp Val Val Ala Val
                165                 170                 175
```

```
Asp Ile Lys Glu Lys Gly Lys Asp Lys Trp Ile Glu Leu Lys Glu Ser
            180                 185                 190

Trp Gly Ala Ile Trp Arg Ile Asp Thr Pro Asp Lys Leu Thr Gly Pro
        195                 200                 205

Phe Thr Val Arg Tyr Thr Thr Glu Gly Gly Lys Thr Glu Ala Glu
    210                 215                 220

Asp Val Ile Pro Glu Gly Trp Lys Ala Asp Thr Ser Tyr Glu Ser Lys
225                 230                 235                 240

<210> SEQ ID NO 2
<211> LENGTH: 96
<212> TYPE: PRT
<213> ORGANISM: Phleum pratense

<400> SEQUENCE: 2

Val Pro Lys Val Thr Phe Thr Val Glu Lys Gly Ser Asn Glu Lys His
1               5                   10                  15

Leu Ala Val Leu Val Lys Tyr Glu Gly Asp Thr Met Ala Glu Val Glu
            20                  25                  30

Leu Arg Glu His Gly Ser Asp Glu Trp Val Ala Met Thr Lys Gly Glu
        35                  40                  45

Gly Gly Val Trp Thr Phe Asp Ser Glu Glu Pro Leu Gln Gly Pro Phe
    50                  55                  60

Asn Phe Arg Phe Leu Thr Glu Lys Gly Met Lys Asn Val Phe Asp Asp
65                  70                  75                  80

Val Val Pro Glu Lys Tyr Thr Ile Gly Ala Thr Tyr Ala Pro Glu Glu
                85                  90                  95

<210> SEQ ID NO 3
<211> LENGTH: 97
<212> TYPE: PRT
<213> ORGANISM: Phleum pratense

<400> SEQUENCE: 3

Ala Val Gln Val Thr Phe Thr Val Gln Lys Gly Ser Asp Pro Lys Lys
1               5                   10                  15

Leu Val Leu Asp Ile Lys Tyr Thr Arg Pro Gly Asp Ser Leu Ala Glu
            20                  25                  30

Val Glu Leu Arg Gln His Gly Ser Glu Glu Trp Glu Pro Leu Thr Lys
        35                  40                  45

Lys Gly Asn Val Trp Glu Val Lys Ser Ser Lys Pro Leu Val Gly Pro
    50                  55                  60

Phe Asn Phe Arg Phe Met Ser Lys Gly Gly Met Arg Asn Val Phe Asp
65                  70                  75                  80

Glu Val Ile Pro Thr Ala Phe Ser Ile Gly Lys Thr Tyr Lys Pro Glu
                85                  90                  95

Glu

<210> SEQ ID NO 4
<211> LENGTH: 508
<212> TYPE: PRT
<213> ORGANISM: Phleum pratense

<400> SEQUENCE: 4

Ser Ser Cys Glu Val Ala Leu Ser Tyr Tyr Pro Thr Pro Leu Ala Lys
1               5                   10                  15

Glu Asp Phe Leu Arg Cys Leu Val Lys Glu Ile Pro Pro Arg Leu Leu
            20                  25                  30
```

-continued

```
Tyr Ala Lys Ser Ser Pro Ala Tyr Pro Ser Val Leu Gly Gln Thr Ile
        35                  40                  45

Arg Asn Ser Arg Trp Ser Ser Pro Asp Asn Val Lys Pro Ile Tyr Ile
    50                  55                  60

Val Thr Pro Thr Asn Ala Ser His Ile Gln Ser Ala Val Val Cys Gly
65                  70                  75                  80

Arg Arg His Gly Val Arg Ile Arg Val Arg Ser Gly Gly His Asp Tyr
                85                  90                  95

Glu Gly Leu Ser Tyr Arg Ser Leu Gln Pro Glu Glu Phe Ala Val Val
            100                 105                 110

Asp Leu Ser Lys Met Arg Ala Val Trp Val Asp Gly Lys Ala Arg Thr
        115                 120                 125

Ala Trp Val Asp Ser Gly Ala Gln Leu Gly Glu Leu Tyr Tyr Ala Ile
    130                 135                 140

His Lys Ala Ser Pro Val Leu Ala Phe Pro Ala Gly Val Cys Pro Thr
145                 150                 155                 160

Ile Gly Val Gly Gly Asn Phe Ala Gly Gly Phe Gly Met Leu Leu
                165                 170                 175

Arg Lys Tyr Gly Ile Ala Ala Glu Asn Val Ile Asp Val Lys Leu Val
            180                 185                 190

Asp Ala Asn Gly Thr Leu His Asp Lys Lys Ser Met Gly Asp Asp His
        195                 200                 205

Phe Trp Ala Val Arg Gly Gly Gly Glu Ser Phe Gly Ile Val Val
    210                 215                 220

Ala Trp Lys Val Arg Leu Leu Pro Val Pro Thr Val Thr Val Phe
225                 230                 235                 240

Lys Ile Pro Lys Lys Ala Ser Glu Gly Ala Val Asp Ile Ile Asn Arg
                245                 250                 255

Trp Gln Val Val Ala Pro Gln Leu Pro Asp Asp Leu Met Ile Arg Val
            260                 265                 270

Ile Ala Gln Gly Pro Thr Ala Thr Phe Glu Ala Met Tyr Leu Gly Thr
        275                 280                 285

Cys Gln Thr Leu Thr Pro Met Met Ser Ser Lys Phe Pro Glu Leu Gly
        290                 295                 300

Met Asn Ala Ser His Cys Asn Glu Met Ser Trp Ile Gln Ser Ile Pro
305                 310                 315                 320

Phe Val His Leu Gly His Arg Asp Asn Ile Glu Asp Leu Leu Asn
                325                 330                 335

Arg Asn Asn Thr Phe Lys Pro Phe Ala Glu Tyr Lys Ser Asp Tyr Val
            340                 345                 350

Tyr Glu Pro Phe Pro Lys Glu Val Trp Glu Gln Ile Phe Ser Thr Trp
        355                 360                 365

Leu Leu Lys Pro Gly Ala Gly Ile Met Ile Phe Asp Pro Tyr Gly Ala
    370                 375                 380

Thr Ile Ser Ala Thr Pro Glu Trp Ala Thr Pro Phe Pro His Arg Lys
385                 390                 395                 400

Gly Val Leu Phe Asn Ile Gln Tyr Val Asn Tyr Trp Phe Ala Pro Gly
                405                 410                 415

Ala Gly Ala Ala Pro Leu Ser Trp Ser Lys Glu Ile Tyr Asn Tyr Met
            420                 425                 430

Glu Pro Tyr Val Ser Lys Asn Pro Arg Gln Ala Tyr Ala Asn Tyr Arg
        435                 440                 445
```

```
Asp Ile Asp Leu Gly Arg Asn Glu Val Val Asn Asp Val Ser Thr Phe
    450                 455                 460
Ser Ser Gly Leu Val Trp Gly Gln Lys Tyr Phe Lys Gly Asn Phe Gln
465                 470                 475                 480
Arg Leu Ala Ile Thr Lys Gly Lys Val Asp Pro Thr Asp Tyr Phe Arg
                485                 490                 495
Asn Glu Gln Ser Ile Pro Pro Leu Ile Gln Lys Tyr
                500                 505
```

<210> SEQ ID NO 5
<211> LENGTH: 287
<212> TYPE: PRT
<213> ORGANISM: Phleum pratense

<400> SEQUENCE: 5

```
Ala Asp Leu Gly Tyr Gly Pro Ala Thr Pro Ala Ala Pro Ala Ala Gly
1               5                   10                  15
Tyr Thr Pro Ala Thr Pro Ala Ala Pro Ala Glu Ala Ala Pro Ala Gly
                20                  25                  30
Lys Ala Thr Thr Glu Glu Gln Lys Leu Ile Glu Lys Ile Asn Ala Gly
                35                  40                  45
Phe Lys Ala Ala Leu Ala Ala Ala Gly Val Gln Pro Ala Asp Lys
50                  55                  60
Tyr Arg Thr Phe Val Ala Thr Phe Gly Ala Ala Ser Asn Lys Ala Phe
65                  70                  75                  80
Ala Glu Gly Leu Ser Gly Glu Pro Lys Gly Ala Ala Glu Ser Ser Ser
                85                  90                  95
Lys Ala Ala Leu Thr Ser Lys Leu Asp Ala Ala Tyr Lys Leu Ala Tyr
                100                 105                 110
Lys Thr Ala Glu Gly Ala Thr Pro Glu Ala Lys Tyr Asp Ala Tyr Val
                115                 120                 125
Ala Thr Leu Ser Glu Ala Leu Arg Ile Ile Ala Gly Thr Leu Glu Val
                130                 135                 140
His Ala Val Lys Pro Ala Ala Glu Gly Val Lys Val Ile Pro Ala Gly
145                 150                 155                 160
Glu Leu Gln Val Ile Glu Lys Val Asp Ala Ala Phe Lys Val Ala Ala
                165                 170                 175
Thr Ala Ala Asn Ala Ala Pro Ala Asn Asp Lys Phe Thr Val Phe Glu
                180                 185                 190
Ala Ala Phe Asn Asp Ala Ile Lys Ala Ser Thr Gly Gly Ala Tyr Glu
                195                 200                 205
Ser Tyr Lys Phe Ile Pro Ala Leu Glu Ala Ala Val Lys Gln Ala Tyr
                210                 215                 220
Ala Ala Thr Val Ala Thr Ala Pro Glu Val Lys Tyr Thr Val Phe Glu
225                 230                 235                 240
Thr Ala Leu Lys Lys Ala Ile Thr Ala Met Ser Glu Ala Gln Lys Ala
                245                 250                 255
Ala Lys Pro Ala Ala Ala Ala Thr Ala Thr Ala Thr Ala Ala Val Gly
                260                 265                 270
Ala Ala Thr Gly Ala Ala Thr Ala Ala Thr Gly Gly Tyr Lys Val
                275                 280                 285
```

<210> SEQ ID NO 6
<211> LENGTH: 110
<212> TYPE: PRT
<213> ORGANISM: Phleum pratense

```
<400> SEQUENCE: 6

Gly Lys Ala Thr Thr Glu Glu Gln Lys Leu Ile Glu Asp Val Asn Ala
1               5                   10                  15

Ser Phe Arg Ala Ala Met Ala Thr Thr Ala Asn Val Pro Pro Ala Asp
            20                  25                  30

Lys Tyr Lys Thr Phe Glu Ala Ala Phe Thr Val Ser Ser Lys Arg Asn
        35                  40                  45

Leu Ala Asp Ala Val Ser Lys Ala Pro Gln Leu Val Pro Lys Leu Asp
    50                  55                  60

Glu Val Tyr Asn Ala Ala Tyr Asn Ala Ala Asp His Ala Ala Pro Glu
65                  70                  75                  80

Asp Lys Tyr Glu Ala Phe Val Leu His Phe Ser Glu Ala Leu Arg Ile
                85                  90                  95

Ile Ala Gly Thr Pro Glu Val His Ala Val Lys Pro Gly Ala
            100                 105                 110

<210> SEQ ID NO 7
<211> LENGTH: 78
<212> TYPE: PRT
<213> ORGANISM: Phleum pratense

<400> SEQUENCE: 7

Met Ala Asp Asp Met Glu Arg Ile Phe Lys Arg Phe Asp Thr Asn Gly
1               5                   10                  15

Asp Gly Lys Ile Ser Leu Ser Glu Leu Thr Asp Ala Leu Arg Thr Leu
            20                  25                  30

Gly Ser Thr Ser Ala Asp Glu Val Gln Arg Met Met Ala Glu Ile Asp
        35                  40                  45

Thr Asp Gly Asp Gly Phe Ile Asp Phe Asn Glu Phe Ile Ser Phe Cys
    50                  55                  60

Asn Ala Asn Pro Gly Leu Met Lys Asp Val Ala Lys Val Phe
65                  70                  75

<210> SEQ ID NO 8
<211> LENGTH: 143
<212> TYPE: PRT
<213> ORGANISM: Phleum pratense

<400> SEQUENCE: 8

Asp Lys Gly Pro Gly Phe Val Val Thr Gly Arg Val Tyr Cys Asp Pro
1               5                   10                  15

Cys Arg Ala Gly Phe Glu Thr Asn Val Ser His Asn Val Gln Gly Ala
            20                  25                  30

Thr Val Ala Val Asp Cys Arg Pro Phe Asn Gly Gly Glu Ser Lys Leu
        35                  40                  45

Lys Ala Glu Ala Thr Thr Asp Gly Leu Gly Trp Tyr Lys Ile Glu Ile
    50                  55                  60

Asp Gln Asp His Gln Glu Ile Cys Glu Val Val Leu Ala Lys Ser
65                  70                  75                  80

Pro Asp Thr Thr Cys Ser Glu Ile Glu Glu Phe Arg Asp Arg Ala Arg
                85                  90                  95

Val Pro Leu Thr Ser Asn Asn Gly Ile Lys Gln Gln Gly Ile Arg Tyr
            100                 105                 110

Ala Asn Pro Ile Ala Phe Phe Arg Lys Glu Pro Leu Lys Glu Cys Gly
        115                 120                 125
```

```
Gly Ile Leu Gln Ala Tyr Asp Leu Arg Asp Ala Pro Glu Thr Pro
        130                 135                 140

<210> SEQ ID NO 9
<211> LENGTH: 131
<212> TYPE: PRT
<213> ORGANISM: Phleum pratense

<400> SEQUENCE: 9

Met Ser Trp Gln Thr Tyr Val Asp Glu His Leu Met Cys Glu Ile Glu
1               5                   10                  15

Gly His His Leu Ala Ser Ala Ala Ile Leu Gly His Asp Gly Thr Val
            20                  25                  30

Trp Ala Gln Ser Ala Asp Phe Pro Gln Phe Lys Pro Glu Glu Ile Thr
        35                  40                  45

Gly Ile Met Lys Asp Phe Asp Glu Pro Gly His Leu Ala Pro Thr Gly
    50                  55                  60

Met Phe Val Ala Gly Ala Lys Tyr Met Val Ile Gln Gly Glu Pro Gly
65                  70                  75                  80

Arg Val Ile Arg Gly Lys Lys Gly Ala Gly Ile Thr Ile Lys Lys
                85                  90                  95

Thr Gly Gln Ala Leu Val Val Gly Ile Tyr Asp Glu Pro Met Thr Pro
            100                 105                 110

Gly Gln Cys Asn Met Val Val Glu Arg Leu Gly Asp Tyr Leu Val Glu
        115                 120                 125

Gln Gly Met
    130

<210> SEQ ID NO 10
<211> LENGTH: 360
<212> TYPE: PRT
<213> ORGANISM: Phleum pratense

<400> SEQUENCE: 10

Gly Lys Lys Glu Glu Lys Lys Glu Glu Lys Glu Ser Gly Asp Ala
1               5                   10                  15

Ala Ser Gly Ala Asp Gly Thr Tyr Asp Ile Thr Lys Leu Gly Ala Lys
            20                  25                  30

Pro Asp Gly Lys Thr Asp Cys Thr Lys Glu Val Glu Glu Ala Trp Ala
        35                  40                  45

Ser Ala Cys Gly Gly Thr Gly Lys Asn Thr Ile Val Ile Pro Lys Gly
    50                  55                  60

Asp Phe Leu Thr Gly Pro Leu Asn Phe Thr Gly Pro Cys Lys Gly Asp
65                  70                  75                  80

Ser Val Thr Ile Lys Leu Asp Gly Asn Leu Leu Ser Ser Asn Asp Leu
                85                  90                  95

Ala Lys Tyr Lys Ala Asn Trp Ile Glu Ile Met Arg Ile Lys Lys Leu
            100                 105                 110

Thr Ile Thr Gly Lys Gly Thr Leu Asp Gly Gln Gly Lys Ala Val Trp
        115                 120                 125

Gly Lys Asn Ser Cys Ala Lys Asn Tyr Asn Cys Lys Ile Leu Pro Asn
    130                 135                 140

Thr Leu Val Leu Asp Phe Cys Asp Asp Ala Leu Ile Glu Gly Ile Thr
145                 150                 155                 160

Leu Leu Asn Ala Lys Phe Phe His Met Asn Ile Tyr Glu Cys Lys Gly
                165                 170                 175
```

Val Thr Val Lys Asp Val Thr Ile Thr Ala Pro Gly Asp Ser Pro Asn
            180                 185                 190

Thr Asp Gly Ile His Ile Gly Asp Ser Ser Lys Val Thr Ile Thr Asp
        195                 200                 205

Thr Thr Ile Gly Thr Gly Asp Asp Cys Ile Ser Ile Gly Pro Gly Ser
    210                 215                 220

Thr Gly Leu Asn Ile Thr Gly Val Thr Cys Gly Pro Gly His Gly Ile
225                 230                 235                 240

Ser Val Gly Ser Leu Gly Arg Tyr Lys Asp Glu Lys Asp Val Thr Asp
                245                 250                 255

Ile Thr Val Lys Asn Cys Val Leu Lys Lys Ser Thr Asn Gly Leu Arg
            260                 265                 270

Ile Lys Ser Tyr Glu Asp Ala Lys Ser Pro Leu Thr Ala Ser Lys Leu
        275                 280                 285

Thr Tyr Glu Asn Val Lys Met Glu Asp Val Gly Tyr Pro Ile Ile Ile
    290                 295                 300

Asp Gln Lys Tyr Cys Pro Asn Lys Ile Cys Thr Ser Lys Gly Asp Ser
305                 310                 315                 320

Ala Arg Val Thr Val Lys Asp Val Thr Phe Arg Asn Ile Thr Gly Thr
                325                 330                 335

Ser Ser Thr Pro Glu Ala Val Ser Leu Leu Cys Ser Asp Lys Gln Pro
            340                 345                 350

Cys Asn Gly Val Thr Met Asn Asp
        355                 360

<210> SEQ ID NO 11
<211> LENGTH: 1066
<212> TYPE: DNA
<213> ORGANISM: Phleum pratense

<400> SEQUENCE: 11
atggcttctt cctcgtcggt tctgctggtc gtggtgcttt tcgccgtctt cctgggctct      60
gcgtatggca tccccaaggt tcccccgggt ccgaacatca cggcgaccta cggcgacaag     120
tggctcgacg cgaagagcac atggtacggc aagccgaccg cgccggtcc caaggacaac     180 ggcggcgctt gcgggtacaa ggatgtggac aagcccccgt tcagcggcat gaccggctgc     240
ggcaacaccc ccatcttcaa gtccggacgc ggctgcggct cctgctttga gatcaagtgc     300
accaagcccg aggcctgctc tggcgagccc gtggtagtcc acatcaccga cgacaacgag     360
gagcccatcg cccctacca cttcgacctc tccggcacg cgttcgggc gatggccaag     420 aagggcgatg agcagaagct cgcagcgcc ggcgagctgg agctccagtt ccggcgcgtc     480
aagtgcaagt acccggaggg caccaaggtg accttccacg tggagaaggg gtccaacccc     540
aactacctgg cgctgcttgt gaagtacgtt aacggcgacg gagacgtggt ggcggtggac     600
atcaaggaga agggcaagga caagtggatc gagctcaagg agtcgtgggg agccatctgg     660
aggatcgaca ctcccgacaa gctcacgggc ccttcaccg tccgctacac caccgagggc     720
ggcaccaaga ccgaagccga ggacgtcatc cctgagggct ggaaggccga caccagctac     780
gagtccaagt gaacaaggag aagtgatcct ctgccttcct cttccggccc ctgcttaatt     840
aattttgcct caaggttacc aataaaccgg ccacagcgag aagacaacca caagcttccg     900
gatgcatgag catattcatg ctgatacgag aataatagtt tgaggtcgag atcttgtgag     960
gtgaaattat gtaggagaca accaatgaag aattggctgc cctcccgccc actcccgacc    1020
gccttgttca tgtatctaaa acagttcatg attatgaaga tatatt                  1066

<210> SEQ ID NO 12
<211> LENGTH: 525
<212> TYPE: DNA
<213> ORGANISM: Phleum pratense

<400> SEQUENCE: 12

```
ttggatatca acccgtatcg atccatgtcc atggcgtcct cctcaagcag cagcttgctg      60
gccatggcgg tgctggcggc gctgtttgcc ggcgcgtggt gcgtcccgaa ggtgacgttc     120
acggtggaga agggtccaa cgagaagcac ctggcggtgc tggtgaagta cgaggggac      180
accatggcgg aggtggagct ccgggagcac ggctccgacg agtgggtcgc catgaccaag     240
ggggagggcg gcgtgtggac gttcgacagc gaggagccgc tccaggggcc cttcaacttc     300
cggttcctca ccgagaaggg catgaagaac gtcttcgacg acgtcgtccc agagaagtac     360
accattgggg ccacctacgc gccagaagag tagccatcgg tccatccaca tgcatgatga     420
tccttccatc catctgattt agttcgattt tccttgtgtt ttggaacgaa ttgttgcaaa     480
ttacatgttc aaagacatat gttgcacgaa attttttact aaaaa                    525
```

<210> SEQ ID NO 13
<211> LENGTH: 294
<212> TYPE: DNA
<213> ORGANISM: Phleum pratense

<400> SEQUENCE: 13

```
gccgtgcagg tgacctttac tgtgcagaag ggttccgacc ccaagaagct ggtgctggac      60
atcaagtaca cgaggccagg ggacagcctc gcggaggtgg agctccggca gcacggctcc     120
gaggagtggg agcccctgac gaagaagggc aacgtgtggg aggtgaagag ctccaagccg     180
ctcgttggcc ccttcaactt ccgcttcatg tccaagggtg gcatgaggaa cgtcttcgac     240
gaggtcatcc ccaccgcctt ctcgatcggc aaaacctaca accggaaga gtga           294
```

<210> SEQ ID NO 14
<211> LENGTH: 1567
<212> TYPE: DNA
<213> ORGANISM: Phleum pratense

<400> SEQUENCE: 14

```
tcctcctgcg aggtcgccct ctcctactat ccgacgccgt tagcgaagga ggacttcctc      60
cgatgcctcg tgaaggagat cccgccgcgc ctcctctacg ccaagagctc gcccgcctac     120
ccctcagtcc tggggcagac catccggaac tcgcggtggt cgtcgccgga caacgtgaag     180
ccgatctaca tcgtcaccc caccaacgcc tcccacatcc agtccgccgt ggtgtgcggc     240
cgccggcacg gtgtccgcat ccgcgtgcgc agcggcgggc acgactacga gggcctctcg     300
taccggtccc tgcagcccga ggagttcgcc gtcgtcgacc ttagcaagat gcgggccgtg     360
tgggtggacg gaaggcccg cacggcgtgg gtcgactccg gcgcgcagct cggcgagctc     420
tactacgcca tccacaaggc gagtccagtg ctggcgttcc cggccggcgt gtgcccgacc     480
atcggcgtgg gcggcaactt cgcgggcggc ggcttcggca tgctgctgcg caagtacggc     540
atcgcggccc agaacgtcat cgacgtgaag ctcgtcgacg ccaacggcac gctgcacgac     600
aagaagtcca tgggcgacga ccatttctgg gccgtcaggg gcggcgggggg cgagagcttc     660
ggcatcgtgg tcgcgtggaa ggtgaggctc ctgccggtgc cgcccacggt gaccgtgttc     720
aagatccca agaaggcgag cgagggcgcc gtggacatca tcaacaggtg gcaggtggtc     780
```

| | |
|---|---|
| gcgccgcagc tcccccgacga cctcatgatc cgcgtcatcg cgcagggccc cacggccacg | 840 |
| ttcgaggcca tgtacctggg cacctgccaa accctgacgc cgatgatgag cagcaagttc | 900 |
| cccgagctcg gcatgaacgc ctcgcactgc aacgagatgt cgtggatcca gtccatcccc | 960 |
| ttcgtccacc tcggccacag ggacaacatc gaggacgacc tcctcaaccg gaacaacacc | 1020 |
| ttcaagccct cgccgaata caagtcggac tacgtctacg agccgttccc caaggaagtg | 1080 |
| tgggagcaga tcttcagcac ctggctcctg aagcccggcg cggggatcat gatcttcgac | 1140 |
| ccctacggcg ccaccatcag cgccaccccg gagtgggcga cgccgttccc tcaccgcaag | 1200 |
| ggcgtcctct tcaacatcca gtacgtcaac tactggttcg ccccgggagc cggcgcggcg | 1260 |
| ccattgtcgt ggagcaagga gatctacaac tacatggagc catacgtgag caagaacccc | 1320 |
| aggcaggcct acgccaacta cagggacatc gacctcggga ggaacgaggt ggtgaacgac | 1380 |
| gtctccacct tcagcagcgg tttggtgtgg ggccagaaat acttcaaggg caatttccag | 1440 |
| aggctcgcca tcaccaaggg caaggtggat cccaccgact acttcaggaa cgagcagagc | 1500 |
| atcccgccgc tcatccagaa gtactagcta gggagatcga tcatgcattt gctggggcgt | 1560 |
| tcgtgga | 1567 |

<210> SEQ ID NO 15
<211> LENGTH: 1192
<212> TYPE: DNA
<213> ORGANISM: Phleum pratense

<400> SEQUENCE: 15

| | |
|---|---|
| ccccatatct tcccacctac ggtacaaaca acagcaagca gcaatggcgg tgcaccagta | 60 |
| cactgtggcg ctgttcctcg ccgtggccct cgtggcgggc ccggccgcct cctacgcggc | 120 |
| cgatctcggt tacggccccg ccaccccagc tgccccggcc gccggctaca ccccccgccac | 180 |
| ccccgccgcc ccggccgaag cggcgccagc aggtaaggcg acgaccgagg agcagaagct | 240 |
| gatcgagaag atcaacgccg gcttcaaggc ggccctggcc gccgccgccg cgtccagcc | 300 |
| agcggacaag tacaggacgt cgtcgcaaac cttcggcgcg gcctccaaca aggccttcgc | 360 |
| ggagggcctc tcgggcgagc ccaagggcgc cgccgaatcc agctccaagg ccgcgctcac | 420 |
| ctccaagctc gacgccgcct acaagctcgc ctacaagaca gccgagggcg cgacgcctga | 480 |
| ggccaagtac gacgcctacg tcgccaccct aagcgaggcg ctccgcatca tcgccggcac | 540 |
| cctcgaggtc cacgccgtca gcccgcggc cgaggaggtc aaggtcatcc ccgccggcga | 600 |
| gctgcaggtc atcgagaagg tcgacgccgc cttcaaggtc gctgccaccg ccgccaacgc | 660 |
| cgccccccgcc aacgacaagt tcaccgtctt cgaggccgcc ttcaacgacg ccatcaaggc | 720 |
| gagcacgggc ggcgcctacg agagctacaa gttcatcccc gccctggagg ccgccgtcaa | 780 |
| gcaggcctac gccgccaccg tcgccaccgc gccggaggtc aagtacactg tctttgagac | 840 |
| cgcactgaaa aaggccatca ccgccatgtc cgaggcacag aaggctgcca agcccgccgc | 900 |
| cgctgccacc gccaccgcaa ccgccgccgt ggcgcggcc accggcgccg ccaccgccgc | 960 |
| tactggtggc tacaaagtct gatcaactcg cgaatagtat acatcaatca cgcacatata | 1020 |
| cgaccgtacg tatgtgtgca tgcattgccg tcgcgtcgag caattttgct gataattaat | 1080 |
| tcttgagttt ttcgttgcat gcatccgcgc gttatagagc gcatgcacgc attgccattt | 1140 |
| gtgtataata atcaaatatc tgcaattcat ttatgaaaaa aaaaaaaaaa aa | 1192 |

<210> SEQ ID NO 16
<211> LENGTH: 571

<212> TYPE: DNA
<213> ORGANISM: Phleum pratense

<400> SEQUENCE: 16

```
ccaacgcacg agtagcaatg gcagcgcaca agttcatggt ggcgatgttc ctcgctgttg      60
ccgttgtgtt gggcttggcc acatccccaa ctgcagaggg agggaaggcc acgaccgagg     120
agcaaaaatt gattgaggac gtcaatgcca gctttagggc ggccatggcc accactgcta     180
acgtccctcc agcagacaag tataagacat cgaagccgc cttcacggtg tcctcaaaga     240
gaaacctcgc tgacgccgtt tcaaaggcgc cccagctggt ccccaagctc gatgaagtct     300
acaacgccgc ctacaatgct gccgatcatg ccgccccaga agacaagtat gaagccttcg     360
tccttcactt ttccgaggct ctccgtatca tcgccggtac ccccgaggtt cacgctgtca     420
agcccggcgc gtagttgttc agcacggtca agatccttga cagcgtcgct gccaccggcg     480
ctgcagccaa cactgccagt ggctaaaaaa ttcgactagc tccttcatac aatgaataca     540
catgtatcat tcaaaaaaaa aaaaaaaaaa a                                    571
```

<210> SEQ ID NO 17
<211> LENGTH: 575
<212> TYPE: DNA
<213> ORGANISM: Phleum pratense

<400> SEQUENCE: 17

```
ccgattcgaa gagtgattcg agctagaagg aggagggatc gatcgataat ggcggacgac      60
atggagagga tcttcaagag gttcgacacg aacggtgacg ggaagatctc tctgtcggag     120
ctgacggacg cactgcggac gctgggctcg acgtcggcgg acgaggtgca gcgcatgatg     180
gcggagatcg acaccgacgg cgacggcttc atcgacttca cgagttcat ctccttctgc     240
aacgccaacc ctggactcat gaaggacgtc gccaaggtct tctgaaaccg tttcatttca     300
cctcagccgt cccatcctgc atcagcatcg atttatcgta cggccggctt tgatttcttt     360
gatctattct ccggtactga gcctcctctt cagttgaggc cggccctaaa ttttgatcat     420
ttatttgctt ctagtaactg ttggtgacca ctgtactatc attttttccc tattaatttt     480
cctgtatttc tctttctttt tataccactc attttgtatc tctggcttca gctcgaaccg     540
tacgttacgt gcttccaatt gtctgtgtgc ggact                                575
```

<210> SEQ ID NO 18
<211> LENGTH: 786
<212> TYPE: DNA
<213> ORGANISM: Phleum pratense

<400> SEQUENCE: 18

```
gacaagggcc cgggcttcgt ggtgacggga cgcgtctact gcgacccctg ccgcgccggc      60
ttcgagacca acgtctccca caacgtccaa ggggcgaccg tggcggtgga ctgccggccg     120
ttcaacggcg gcgagagcaa gctcaaggcg gaggcgacga cggacggtct gggctggtac     180
aagatcgaga tcgaccagga ccaccaggag gagatctgcg aggtggtgct ggccaagagc     240
cccgacacga cgtgctccga gatcgaggag ttccgcgacc gcgcccgcgt cccgctcacc     300
agcaacaacg gcatcaagca gcagggcatc cgctacgcca accccatcgc attcttccgc     360
aaggagccgc tcaaggagtg cggcgggatc ctccaggcct acgacctcag ggacgccccc     420
gagacgccat gaagccccac accagcacga cgtaccacct atagttactt gccgccggcc     480
gagacgatgt tacctctgcg agccgctgcc ggagaggara tgacaacctt ttaatgggcc     540
```

| | |
|---|---:|
| tcacgtgcgc cttaatattc rcgtcctgct ttctctttta ttcatgttat tgtcttcctg | 600 |
| tyctctaatt atttacgtgt tgacctatat gtgagctagt tccaaggatc tgttctatgt | 660 |
| gtaataagag aacacaaata tttsgtacgt gcatatccga tgtatatcct cttttcgggg | 720 |
| aaaaaaaawa ytctgatgta tatcctctgg acacaaatta artggccagc taatgaatts | 780 |
| agtact | 786 |

<210> SEQ ID NO 19
<211> LENGTH: 396
<212> TYPE: DNA
<213> ORGANISM: Phleum pratense

<400> SEQUENCE: 19

| | |
|---|---:|
| atgtcgtggc agacgtacgt ggacgagcac ctgatgtgcg agatcgaggg ccaccacctc | 60 |
| gcctcggcgg ccatcctcgg ccacgacggc accgtctggg cccagagcgc cgacttcccc | 120 |
| cagttcaagc ctgaggagat caccggcatc atgaaggatt tcgacgagcc ggggcacctc | 180 |
| gcccccaccg gcatgttcgt cgcaggtgcc aagtacatgg tcatccaggg tgaacccggt | 240 |
| cgcgtcatcc gtggcaagaa gggagcagga ggcatcacca taaagaagac cgggcaggcg | 300 |
| ctggtcgtcg gcatctatga cgagcccatg acccctgggc agtgcaacat ggtggtggag | 360 |
| aggcttggcg actacctcgt tgaacaaggc atgtag | 396 |

<210> SEQ ID NO 20
<211> LENGTH: 1492
<212> TYPE: DNA
<213> ORGANISM: Phleum pratense

<400> SEQUENCE: 20

| | |
|---|---:|
| gggaagaagg aggagaagaa ggaggagaag aaggagagtg agatgctgc gtccggggcc | 60 |
| gacggaacct acgacatcac caagctcggc gccaaacccg acggcaagac ggactgcacc | 120 |
| aaggaggtgg aggaggcatg ggcttcggct tgcgtggta ccgggaagaa tacgatcgtc | 180 |
| atccccaagg gtgatttcct gaccgggcct ctgaatttca ccgggccatg caagggcgac | 240 |
| agcgtcacca tcaagctgga cggcaacctg ctgagctcca cgacctggc caagtacaag | 300 |
| gctaactgga tcgagatcat gcggatcaag aaactcacta tcaccggcaa aggcacgctc | 360 |
| gacggccaag gcaaggccgt gtggggcaag aacagctgcg ccaagaacta caactgcaag | 420 |
| atcttgccaa acacattggt gctggacttc tgtgacgacg ctctcatcga aggcatcacc | 480 |
| ctcctaaacg ccaagttctt ccatatgaac atctacgagt gcaagggcgt gaccgtcaag | 540 |
| gacgtgacca tcaccgcgcc cggggacagc cccaacaccg acggcatcca catcggcgac | 600 |
| tcgtccaagg tcaccatcac cgacaccacc atcggcaccg cgacgactg catctccatc | 660 |
| ggccccggaa gcaccggcct caacatcacc ggcgtgacct gcggtccagg ccacggcatc | 720 |
| agcgttggca gcctgggacg gtacaaggac gagaaggacg tgaccgacat caccgtaaag | 780 |
| aactgcgtgc tcaagaagtc caccaacggc ctccggatca agtcgtacga ggacgccaag | 840 |
| tcgccgctga cggcgtcgaa gctgacctac gagaacgtga agatggagga cgtgggctac | 900 |
| cccatcatca tcgaccagaa gtactgcccc aacaagatct gcacctccaa gggagactcc | 960 |
| gccagggtca ccgtcaagga cgtcaccttc cgcaacatca ccggcacctc ctccacccc | 1020 |
| gaggccgtca gcctgctctg ctccgacaag cagccctgca atggtgtcac catgaacgac | 1080 |
| gtcaagatcg agtacagcgg caccaacaac aagaccatgc tgtctgcac caacgccaag | 1140 |
| gtcaccgcca agggtgtcag cgaggctaac acctgcgccg cctgatgagc gactcttctc | 1200 |

```
cacctgcttc acgttccat caattcgtcc tacctcccac acatgtcctt ttttctgaag    1260
agataattaa caagaccgcg cgtgcatatc ctggcgatca tttctgcta actctggaga    1320 tgtaccctag acataaatac tgtgcgatat tatggtaaat gcgaatcctt taatctacct    1380
gtgctcaagt tgtgccgggt ttttgtatga taaacagatt atgtaacttt tttctgtaat    1440 cttttattg catccgaatt tctggaattt tagtcaaaaa aaaaaaaaaa aa              1492
```

<210> SEQ ID NO 21
<211> LENGTH: 246
<212> TYPE: PRT
<213> ORGANISM: Artificial Sequence
<220> FEATURE:
<223> OTHER INFORMATION: construct A without N-terminal Met and
      C-terminal hexahistidine

<400> SEQUENCE: 21

```
Ser Gly Arg Gly Cys Gly Ser Cys Phe Glu Ile Lys Cys Thr Lys Pro
1               5                   10                  15

Glu Ala Cys Ser Gly Glu Pro Val Val Val His Ile Thr Asp Asp Asn
                20                  25                  30

Glu Glu Pro Ile Ala Pro Tyr His Phe Asp Leu Ser Gly His Ala Phe
            35                  40                  45

Gly Ala Met Ala Lys Lys Gly Asp Glu Gln Lys Leu Arg Thr Gly Pro
        50                  55                  60

Phe Thr Val Arg Tyr Thr Thr Glu Gly Gly Thr Lys Thr Glu Ala Glu
65                  70                  75                  80

Asp Val Ile Pro Glu Gly Trp Lys Ala Asp Thr Ser Tyr Glu Ser Lys
                85                  90                  95

Gly Ala Ala Ser Asn Lys Ala Phe Ala Glu Gly Leu Ser Gly Glu Pro
            100                 105                 110

Lys Gly Ala Ala Glu Ser Ser Ser Lys Ala Ala Leu Thr Ser Lys Leu
        115                 120                 125

Asp Ala Ala Tyr Lys Leu Ala Tyr Lys Thr Ala Glu Gly Ala Thr Pro
130                 135                 140

Glu Ala Lys Tyr Asp Ala Tyr Val Ala Thr Leu Ser Glu Ala Leu Arg
145                 150                 155                 160

Ile Ile Ala Gly Thr Leu Glu Val His Ala Val Lys Pro Ala Ala Asp
                165                 170                 175

Leu Gly Tyr Gly Pro Ala Thr Pro Ala Ala Pro Ala Ala Gly Tyr Thr
            180                 185                 190

Pro Ala Thr Pro Ala Ala Pro Ala Glu Ala Ala Pro Ala Gly Lys Ala
        195                 200                 205

Thr Thr Glu Glu Gln Lys Leu Ile Glu Lys Ile Asn Ala Gly Phe Lys
    210                 215                 220

Ala Ala Leu Ala Ala Ala Gly Val Gln Pro Ala Asp Lys Tyr Arg
225                 230                 235                 240

Thr Phe Val Ala Thr Phe
                245
```

<210> SEQ ID NO 22
<211> LENGTH: 281
<212> TYPE: PRT
<213> ORGANISM: Artificial Sequence
<220> FEATURE:
<223> OTHER INFORMATION: construct B without N-terminal Met and
      C-terminal hexahistidine

<400> SEQUENCE: 22

```
Ala Val Lys Gln Ala Tyr Ala Ala Thr Val Thr Ala Pro Glu Val
1               5                   10                  15

Lys Tyr Thr Val Phe Glu Thr Ala Leu Lys Lys Ala Ile Thr Ala Met
            20                  25                  30

Ser Glu Ala Gln Lys Ala Ala Lys Pro Ala Ala Ala Thr Ala Thr
            35                  40                  45

Ala Thr Ala Ala Val Gly Ala Ala Thr Gly Ala Ala Thr Ala Ala Thr
        50                  55                  60

Gly Gly Tyr Lys Val Ala Glu Val Lys Val Ile Pro Ala Gly Glu
65                  70                  75                  80

Leu Gln Val Ile Glu Lys Val Asp Ala Ala Phe Lys Val Ala Ala Thr
                85                  90                  95

Ala Ala Asn Ala Ala Pro Ala Asn Asp Lys Phe Thr Val Phe Glu Ala
            100                 105                 110

Ala Phe Asn Asp Ala Ile Lys Ala Ser Thr Gly Gly Ala Tyr Glu Ser
            115                 120                 125

Tyr Lys Phe Ile Pro Ala Leu Glu Ala Ile Pro Lys Val Pro Pro Gly
    130                 135                 140

Pro Asn Ile Thr Ala Thr Tyr Gly Asp Lys Trp Leu Asp Ala Lys Ser
145                 150                 155                 160

Thr Trp Tyr Gly Lys Pro Thr Gly Ala Gly Pro Lys Asp Asn Gly Gly
                165                 170                 175

Ala Cys Gly Tyr Lys Asp Val Asp Lys Pro Pro Phe Ser Gly Met Thr
            180                 185                 190

Gly Cys Gly Asn Thr Pro Ile Phe Lys Ser Ala Gly Glu Leu Glu Leu
        195                 200                 205

Gln Phe Arg Arg Val Lys Cys Lys Tyr Pro Glu Gly Thr Lys Val Thr
    210                 215                 220

Phe His Val Glu Lys Gly Ser Asn Pro Asn Tyr Leu Ala Leu Leu Val
225                 230                 235                 240

Lys Tyr Val Asn Gly Asp Gly Asp Val Val Ala Val Asp Ile Lys Glu
            245                 250                 255

Lys Gly Lys Asp Lys Trp Ile Glu Leu Lys Glu Ser Trp Gly Ala Ile
            260                 265                 270

Trp Arg Ile Asp Thr Pro Asp Lys Leu
        275                 280
```

<210> SEQ ID NO 23
<211> LENGTH: 246
<212> TYPE: PRT
<213> ORGANISM: Artificial Sequence
<220> FEATURE:
<223> OTHER INFORMATION: construct C without N-terminal Met and C-terminal hexahistidine

<400> SEQUENCE: 23

```
Gly Ala Ala Ser Asn Lys Ala Phe Ala Glu Gly Leu Ser Gly Glu Pro
1               5                   10                  15

Lys Gly Ala Ala Glu Ser Ser Ser Lys Ala Ala Leu Thr Ser Lys Leu
            20                  25                  30

Asp Ala Ala Tyr Lys Leu Ala Tyr Lys Thr Ala Glu Gly Ala Thr Pro
        35                  40                  45

Glu Ala Lys Tyr Asp Ala Tyr Val Ala Thr Leu Ser Glu Ala Leu Arg
50                  55                  60
```

```
Ile Ile Ala Gly Thr Leu Glu Val His Ala Val Lys Pro Ala Ala Asp
 65                  70                  75                  80

Leu Gly Tyr Gly Pro Ala Thr Pro Ala Ala Pro Ala Ala Gly Tyr Thr
                 85                  90                  95

Pro Ala Thr Pro Ala Ala Pro Ala Glu Ala Ala Pro Ala Gly Lys Ala
            100                 105                 110

Thr Thr Glu Glu Gln Lys Leu Ile Glu Lys Ile Asn Ala Gly Phe Lys
        115                 120                 125

Ala Ala Leu Ala Ala Ala Gly Val Gln Pro Ala Asp Lys Tyr Arg
130                 135                 140

Thr Phe Val Ala Thr Phe Ser Gly Arg Gly Cys Gly Ser Cys Phe Glu
145                 150                 155                 160

Ile Lys Cys Thr Lys Pro Glu Ala Cys Ser Gly Glu Pro Val Val Val
                165                 170                 175

His Ile Thr Asp Asp Asn Glu Glu Pro Ile Ala Pro Tyr His Phe Asp
                180                 185                 190

Leu Ser Gly His Ala Phe Gly Ala Met Ala Lys Lys Gly Asp Glu Gln
            195                 200                 205

Lys Leu Arg Thr Gly Pro Phe Thr Val Arg Tyr Thr Thr Glu Gly Gly
        210                 215                 220

Thr Lys Thr Glu Ala Glu Asp Val Ile Pro Glu Gly Trp Lys Ala Asp
225                 230                 235                 240

Thr Ser Tyr Glu Ser Lys
                245

<210> SEQ ID NO 24
<211> LENGTH: 281
<212> TYPE: PRT
<213> ORGANISM: Artificial Sequence
<220> FEATURE:
<223> OTHER INFORMATION: construct D without N-terminal Met and
      C-terminal hexahistidine

<400> SEQUENCE: 24

Ile Pro Lys Val Pro Gly Pro Asn Ile Thr Ala Thr Tyr Gly Asp
 1               5                  10                  15

Lys Trp Leu Asp Ala Lys Ser Thr Trp Tyr Gly Lys Pro Thr Gly Ala
                20                  25                  30

Gly Pro Lys Asp Asn Gly Gly Ala Cys Gly Tyr Lys Asp Val Asp Lys
            35                  40                  45

Pro Pro Phe Ser Gly Met Thr Gly Cys Gly Asn Thr Pro Ile Phe Lys
        50                  55                  60

Ser Ala Gly Glu Leu Glu Leu Gln Phe Arg Arg Val Lys Cys Lys Tyr
 65                  70                  75                  80

Pro Glu Gly Thr Lys Val Thr Phe His Val Lys Gly Ser Asn Pro
                85                  90                  95

Asn Tyr Leu Ala Leu Leu Val Lys Tyr Val Asn Gly Asp Gly Asp Val
            100                 105                 110

Val Ala Val Asp Ile Lys Glu Lys Gly Lys Asp Lys Trp Ile Glu Leu
        115                 120                 125

Lys Glu Ser Trp Gly Ala Ile Trp Arg Ile Asp Thr Pro Asp Lys Leu
130                 135                 140

Ala Val Lys Gln Ala Tyr Ala Ala Thr Val Thr Ala Pro Glu Val
145                 150                 155                 160

Lys Tyr Thr Val Phe Glu Thr Ala Leu Lys Lys Ala Ile Thr Ala Met
                165                 170                 175
```

```
Ser Glu Ala Gln Lys Ala Ala Lys Pro Ala Ala Ala Thr Ala Thr
            180                 185                 190

Ala Thr Ala Ala Val Gly Ala Ala Thr Gly Ala Ala Thr Ala Ala Thr
    195                 200                 205

Gly Gly Tyr Lys Val Ala Glu Glu Val Lys Val Ile Pro Ala Gly Glu
    210                 215                 220

Leu Gln Val Ile Glu Lys Val Asp Ala Ala Phe Lys Val Ala Ala Thr
225                 230                 235                 240

Ala Ala Asn Ala Ala Pro Ala Asn Asp Lys Phe Thr Val Phe Glu Ala
                245                 250                 255

Ala Phe Asn Asp Ala Ile Lys Ala Ser Thr Gly Gly Ala Tyr Glu Ser
            260                 265                 270

Tyr Lys Phe Ile Pro Ala Leu Glu Ala
        275                 280
```

<210> SEQ ID NO 25
<211> LENGTH: 294
<212> TYPE: PRT
<213> ORGANISM: Artificial Sequence
<220> FEATURE:
<223> OTHER INFORMATION: construct E without N-terminal Met and
      C-terminal hexahistidine

<400> SEQUENCE: 25

```
Gly Ala Ala Ser Asn Lys Ala Phe Ala Glu Gly Leu Ser Gly Glu Pro
1               5                   10                  15

Lys Gly Ala Ala Glu Ser Ser Ser Lys Ala Ala Leu Thr Ser Lys Leu
            20                  25                  30

Asp Ala Ala Tyr Lys Leu Ala Tyr Lys Thr Ala Glu Gly Ala Thr Pro
        35                  40                  45

Glu Ala Lys Tyr Asp Ala Tyr Val Ala Thr Leu Ser Glu Ala Leu Arg
    50                  55                  60

Ile Ile Ala Gly Thr Leu Glu Val His Ala Val Lys Pro Ala Ala Asp
65                  70                  75                  80

Leu Gly Tyr Gly Pro Ala Thr Pro Ala Ala Pro Ala Ala Gly Tyr Thr
                85                  90                  95

Pro Ala Thr Pro Ala Ala Pro Ala Glu Ala Pro Ala Gly Lys Ala
            100                 105                 110

Thr Thr Glu Glu Gln Lys Leu Ile Glu Lys Ile Asn Ala Gly Phe Lys
            115                 120                 125

Ala Ala Leu Ala Ala Ala Gly Val Gln Pro Ala Asp Lys Tyr Arg
        130                 135                 140

Thr Phe Val Ala Thr Phe Ile Pro Lys Val Pro Pro Gly Pro Asn Ile
145                 150                 155                 160

Thr Ala Thr Tyr Gly Asp Lys Trp Leu Asp Ala Lys Ser Thr Trp Tyr
                165                 170                 175

Gly Lys Pro Thr Gly Ala Gly Pro Lys Asp Asn Gly Gly Ala Cys Gly
            180                 185                 190

Tyr Lys Asp Val Asp Lys Pro Pro Phe Ser Gly Met Thr Gly Cys Gly
        195                 200                 205

Asn Thr Pro Ile Phe Lys Ser Ala Gly Glu Leu Glu Leu Gln Phe Arg
    210                 215                 220

Arg Val Lys Cys Lys Tyr Pro Glu Gly Thr Lys Val Thr Phe His Val
225                 230                 235                 240

Glu Lys Gly Ser Asn Pro Asn Tyr Leu Ala Leu Leu Val Lys Tyr Val
```

```
                245                 250                 255
Asn Gly Asp Gly Asp Val Val Ala Val Asp Ile Lys Glu Lys Gly Lys
            260                 265                 270

Asp Lys Trp Ile Glu Leu Lys Glu Ser Trp Gly Ala Ile Trp Arg Ile
            275                 280                 285

Asp Thr Pro Asp Lys Leu
            290

<210> SEQ ID NO 26
<211> LENGTH: 294
<212> TYPE: PRT
<213> ORGANISM: Artificial Sequence
<220> FEATURE:
<223> OTHER INFORMATION: construct F without N-terminal Met and
      C-terminal hexahistidine

<400> SEQUENCE: 26

Ile Pro Lys Val Pro Pro Gly Pro Asn Ile Thr Ala Thr Tyr Gly Asp
1               5                   10                  15

Lys Trp Leu Asp Ala Lys Ser Thr Trp Tyr Gly Lys Pro Thr Gly Ala
            20                  25                  30

Gly Pro Lys Asp Asn Gly Gly Ala Cys Gly Tyr Lys Asp Val Asp Lys
        35                  40                  45

Pro Pro Phe Ser Gly Met Thr Gly Cys Gly Asn Thr Pro Ile Phe Lys
    50                  55                  60

Ser Ala Gly Glu Leu Glu Leu Gln Phe Arg Arg Val Lys Cys Lys Tyr
65                  70                  75                  80

Pro Glu Gly Thr Lys Val Thr Phe His Val Lys Gly Ser Asn Pro
                85                  90                  95

Asn Tyr Leu Ala Leu Leu Val Lys Tyr Val Asn Gly Asp Gly Asp Val
            100                 105                 110

Val Ala Val Asp Ile Lys Glu Lys Gly Lys Asp Lys Trp Ile Glu Leu
        115                 120                 125

Lys Glu Ser Trp Gly Ala Ile Trp Arg Ile Asp Thr Pro Asp Lys Leu
    130                 135                 140

Gly Ala Ala Ser Asn Lys Ala Phe Ala Glu Gly Leu Ser Gly Glu Pro
145                 150                 155                 160

Lys Gly Ala Ala Glu Ser Ser Ser Lys Ala Ala Leu Thr Ser Lys Leu
                165                 170                 175

Asp Ala Ala Tyr Lys Leu Ala Tyr Lys Thr Ala Glu Gly Ala Thr Pro
            180                 185                 190

Glu Ala Lys Tyr Asp Ala Tyr Val Ala Thr Leu Ser Glu Ala Leu Arg
        195                 200                 205

Ile Ile Ala Gly Thr Leu Glu Val His Ala Val Lys Pro Ala Ala Asp
    210                 215                 220

Leu Gly Tyr Gly Pro Ala Thr Pro Ala Ala Pro Ala Ala Gly Tyr Thr
225                 230                 235                 240

Pro Ala Thr Pro Ala Ala Pro Ala Glu Ala Ala Pro Ala Gly Lys Ala
                245                 250                 255

Thr Thr Glu Glu Gln Lys Leu Ile Glu Lys Ile Asn Ala Gly Phe Lys
            260                 265                 270

Ala Ala Leu Ala Ala Ala Ala Gly Val Gln Pro Ala Asp Lys Tyr Arg
        275                 280                 285

Thr Phe Val Ala Thr Phe
    290
```

<210> SEQ ID NO 27
<211> LENGTH: 233
<212> TYPE: PRT
<213> ORGANISM: Artificial Sequence
<220> FEATURE:
<223> OTHER INFORMATION: construct G without N-terminal Met and
      C-terminal hexahistidine

<400> SEQUENCE: 27

Ser Gly Arg Gly Cys Gly Ser Cys Phe Glu Ile Lys Cys Thr Lys Pro
1               5                   10                  15

Glu Ala Cys Ser Gly Glu Pro Val Val Val His Ile Thr Asp Asp Asn
            20                  25                  30

Glu Glu Pro Ile Ala Pro Tyr His Phe Asp Leu Ser Gly His Ala Phe
        35                  40                  45

Gly Ala Met Ala Lys Lys Gly Asp Glu Gln Lys Leu Arg Thr Gly Pro
    50                  55                  60

Phe Thr Val Arg Tyr Thr Thr Glu Gly Gly Thr Lys Thr Glu Ala Glu
65                  70                  75                  80

Asp Val Ile Pro Glu Gly Trp Lys Ala Asp Thr Ser Tyr Glu Ser Lys
                85                  90                  95

Ala Val Lys Gln Ala Tyr Ala Ala Thr Val Ala Thr Ala Pro Glu Val
            100                 105                 110

Lys Tyr Thr Val Phe Glu Thr Ala Leu Lys Lys Ala Ile Thr Ala Met
        115                 120                 125

Ser Glu Ala Gln Lys Ala Ala Lys Pro Ala Ala Ala Thr Ala Thr
    130                 135                 140

Ala Thr Ala Ala Val Gly Ala Ala Thr Gly Ala Ala Thr Ala Ala Thr
145                 150                 155                 160

Gly Gly Tyr Lys Val Ala Glu Glu Val Lys Val Ile Pro Ala Gly Glu
                165                 170                 175

Leu Gln Val Ile Glu Lys Val Asp Ala Ala Phe Lys Val Ala Ala Thr
            180                 185                 190

Ala Ala Asn Ala Ala Pro Ala Asn Asp Lys Phe Thr Val Phe Glu Ala
        195                 200                 205

Ala Phe Asn Asp Ala Ile Lys Ala Ser Thr Gly Gly Ala Tyr Glu Ser
    210                 215                 220

Tyr Lys Phe Ile Pro Ala Leu Glu Ala
225                 230

<210> SEQ ID NO 28
<211> LENGTH: 233
<212> TYPE: PRT
<213> ORGANISM: Artificial Sequence
<220> FEATURE:
<223> OTHER INFORMATION: construct H without N-terminal Met and
      C-terminal hexahistidine

<400> SEQUENCE: 28

Ala Val Lys Gln Ala Tyr Ala Ala Thr Val Ala Thr Ala Pro Glu Val
1               5                   10                  15

Lys Tyr Thr Val Phe Glu Thr Ala Leu Lys Lys Ala Ile Thr Ala Met
            20                  25                  30

Ser Glu Ala Gln Lys Ala Ala Lys Pro Ala Ala Ala Thr Ala Thr
        35                  40                  45

Ala Thr Ala Ala Val Gly Ala Ala Thr Gly Ala Ala Thr Ala Ala Thr
    50                  55                  60

Gly Gly Tyr Lys Val Ala Glu Glu Val Lys Val Ile Pro Ala Gly Glu
65                  70                  75                  80

Leu Gln Val Ile Glu Lys Val Asp Ala Ala Phe Lys Val Ala Ala Thr
            85                  90                  95

Ala Ala Asn Ala Ala Pro Ala Asn Asp Lys Phe Thr Val Phe Glu Ala
        100                 105                 110

Ala Phe Asn Asp Ala Ile Lys Ala Ser Thr Gly Gly Ala Tyr Glu Ser
        115                 120                 125

Tyr Lys Phe Ile Pro Ala Leu Glu Ala Ser Gly Arg Gly Cys Gly Ser
        130                 135                 140

Cys Phe Glu Ile Lys Cys Thr Lys Pro Glu Ala Cys Ser Gly Glu Pro
145                 150                 155                 160

Val Val Val His Ile Thr Asp Asp Asn Glu Glu Pro Ile Ala Pro Tyr
                165                 170                 175

His Phe Asp Leu Ser Gly His Ala Phe Gly Ala Met Ala Lys Lys Gly
            180                 185                 190

Asp Glu Gln Lys Leu Arg Thr Gly Pro Phe Thr Val Arg Tyr Thr Thr
        195                 200                 205

Glu Gly Gly Thr Lys Thr Glu Ala Glu Asp Val Ile Pro Glu Gly Trp
210                 215                 220

Lys Ala Asp Thr Ser Tyr Glu Ser Lys
225                 230

<210> SEQ ID NO 29
<211> LENGTH: 176
<212> TYPE: PRT
<213> ORGANISM: Artificial Sequence
<220> FEATURE:
<223> OTHER INFORMATION: construct I without N-terminal Met and
      C-terminal hexahistidine

<400> SEQUENCE: 29

Ala Asp Lys Tyr Lys Thr Phe Glu Ala Ala Phe Thr Val Ser Ser Lys
1               5                   10                  15

Arg Asn Leu Ala Asp Ala Val Ser Lys Ala Pro Gln Leu Val Pro Lys
            20                  25                  30

Leu Asp Glu Val Tyr Asn Ala Ala Tyr Asn Ala Ala Asp His Ala Ala
        35                  40                  45

Pro Glu Asp Lys Tyr Glu Ala Phe Val Leu His Phe Ser Glu Ala Leu
    50                  55                  60

Arg Ile Ile Ala Gly Thr Pro Glu Val His Ala Val Lys Pro Gly Ala
65                  70                  75                  80

Gly Val Trp Thr Phe Asp Ser Glu Glu Pro Leu Gln Gly Pro Phe Asn
                85                  90                  95

Phe Arg Phe Leu Thr Glu Lys Gly Met Lys Asn Val Phe Asp Asp Val
            100                 105                 110

Val Pro Glu Lys Tyr Thr Ile Gly Ala Thr Tyr Ala Pro Glu Glu Val
        115                 120                 125

Pro Lys Val Thr Phe Thr Val Glu Lys Gly Ser Asn Glu Lys His Leu
    130                 135                 140

Ala Val Leu Val Lys Tyr Glu Gly Asp Thr Met Ala Glu Val Glu Leu
145                 150                 155                 160

Arg Glu His Gly Ser Asp Glu Trp Val Ala Met Thr Lys Gly Glu Gly
                165                 170                 175

<210> SEQ ID NO 30

<211> LENGTH: 176
<212> TYPE: PRT
<213> ORGANISM: Artificial Sequence
<220> FEATURE:
<223> OTHER INFORMATION: construct J without N-terminal Met and
      C-terminal hexahistidine

<400> SEQUENCE: 30

Gly Val Trp Thr Phe Asp Ser Glu Glu Pro Leu Gln Gly Pro Phe Asn
1               5                   10                  15

Phe Arg Phe Leu Thr Glu Lys Gly Met Lys Asn Val Phe Asp Asp Val
                20                  25                  30

Val Pro Glu Lys Tyr Thr Ile Gly Ala Thr Tyr Ala Pro Glu Glu Val
            35                  40                  45

Pro Lys Val Thr Phe Thr Val Glu Lys Gly Ser Asn Glu Lys His Leu
    50                  55                  60

Ala Val Leu Val Lys Tyr Glu Gly Asp Thr Met Ala Glu Val Glu Leu
65                  70                  75                  80

Arg Glu His Gly Ser Asp Glu Trp Val Ala Met Thr Lys Gly Glu Gly
                85                  90                  95

Ala Asp Lys Tyr Lys Thr Phe Glu Ala Ala Phe Thr Val Ser Ser Lys
            100                 105                 110

Arg Asn Leu Ala Asp Ala Val Ser Lys Ala Pro Gln Leu Val Pro Lys
        115                 120                 125

Leu Asp Glu Val Tyr Asn Ala Ala Tyr Asn Ala Ala Asp His Ala Ala
    130                 135                 140

Pro Glu Asp Lys Tyr Glu Ala Phe Val Leu His Phe Ser Glu Ala Leu
145                 150                 155                 160

Arg Ile Ile Ala Gly Thr Pro Glu Val His Ala Val Lys Pro Gly Ala
                165                 170                 175

<210> SEQ ID NO 31
<211> LENGTH: 176
<212> TYPE: PRT
<213> ORGANISM: Artificial Sequence
<220> FEATURE:
<223> OTHER INFORMATION: construct K without N-terminal Met and
      C-terminal hexahistidine

<400> SEQUENCE: 31

Gly Val Trp Thr Phe Asp Ser Glu Glu Pro Leu Gln Gly Pro Phe Asn
1               5                   10                  15

Phe Arg Phe Leu Thr Glu Lys Gly Met Lys Asn Val Phe Asp Asp Val
                20                  25                  30

Val Pro Glu Lys Tyr Thr Ile Gly Ala Thr Tyr Ala Pro Glu Glu Ala
            35                  40                  45

Asp Lys Tyr Lys Thr Phe Glu Ala Ala Phe Thr Val Ser Ser Lys Arg
    50                  55                  60

Asn Leu Ala Asp Ala Val Ser Lys Ala Pro Gln Leu Val Pro Lys Leu
65                  70                  75                  80

Asp Glu Val Tyr Asn Ala Ala Tyr Asn Ala Ala Asp His Ala Ala Pro
                85                  90                  95

Glu Asp Lys Tyr Glu Ala Phe Val Leu His Phe Ser Glu Ala Leu Arg
            100                 105                 110

Ile Ile Ala Gly Thr Pro Glu Val His Ala Val Lys Pro Gly Ala Val
        115                 120                 125

Pro Lys Val Thr Phe Thr Val Glu Lys Gly Ser Asn Glu Lys His Leu
    130                 135                 140

```
Ala Val Leu Val Lys Tyr Glu Gly Asp Thr Met Ala Glu Val Glu Leu
145                 150                 155                 160

Arg Glu His Gly Ser Asp Glu Trp Val Ala Met Thr Lys Gly Glu Gly
                165                 170                 175
```

<210> SEQ ID NO 32
<211> LENGTH: 176
<212> TYPE: PRT
<213> ORGANISM: Artificial Sequence
<220> FEATURE:
<223> OTHER INFORMATION: construct L without N-terminal Met and
      C-terminal hexahistidine

<400> SEQUENCE: 32

```
Val Pro Lys Val Thr Phe Thr Val Glu Lys Gly Ser Asn Glu Lys His
1               5                   10                  15

Leu Ala Val Leu Val Lys Tyr Glu Gly Asp Thr Met Ala Glu Val Glu
                20                  25                  30

Leu Arg Glu His Gly Ser Asp Glu Trp Val Ala Met Thr Lys Gly Glu
            35                  40                  45

Gly Ala Asp Lys Tyr Lys Thr Phe Glu Ala Ala Phe Thr Val Ser Ser
50                  55                  60

Lys Arg Asn Leu Ala Asp Ala Val Ser Lys Ala Pro Gln Leu Val Pro
65                  70                  75                  80

Lys Leu Asp Glu Val Tyr Asn Ala Ala Tyr Asn Ala Ala Asp His Ala
                85                  90                  95

Ala Pro Glu Asp Lys Tyr Glu Ala Phe Val Leu His Phe Ser Glu Ala
            100                 105                 110

Leu Arg Ile Ile Ala Gly Thr Pro Glu Val His Ala Val Lys Pro Gly
        115                 120                 125

Ala Gly Val Trp Thr Phe Asp Ser Glu Glu Pro Leu Gln Gly Pro Phe
130                 135                 140

Asn Phe Arg Phe Leu Thr Glu Lys Gly Met Lys Asn Val Phe Asp Asp
145                 150                 155                 160

Val Val Pro Glu Lys Tyr Thr Ile Gly Ala Thr Tyr Ala Pro Glu Glu
                165                 170                 175
```

<210> SEQ ID NO 33
<211> LENGTH: 703
<212> TYPE: PRT
<213> ORGANISM: Artificial Sequence
<220> FEATURE:
<223> OTHER INFORMATION: construct M without N-terminal Met and
      C-terminal hexahistidine

<400> SEQUENCE: 33

```
Ala Asp Lys Tyr Lys Thr Phe Glu Ala Ala Phe Thr Val Ser Ser Lys
1               5                   10                  15

Arg Asn Leu Ala Asp Ala Val Ser Lys Ala Pro Gln Leu Val Pro Lys
                20                  25                  30

Leu Asp Glu Val Tyr Asn Ala Ala Tyr Asn Ala Ala Asp His Ala Ala
            35                  40                  45

Pro Glu Asp Lys Tyr Glu Ala Phe Val Leu His Phe Ser Glu Ala Leu
50                  55                  60

Arg Ile Ile Ala Gly Thr Pro Glu Val His Ala Val Lys Pro Gly Ala
65                  70                  75                  80

Gly Val Trp Thr Phe Asp Ser Glu Glu Pro Leu Gln Gly Pro Phe Asn
                85                  90                  95
```

```
Phe Arg Phe Leu Thr Glu Lys Gly Met Lys Asn Val Phe Asp Val
                100                 105                 110

Val Pro Glu Lys Tyr Thr Ile Gly Ala Thr Tyr Ala Pro Glu Val
            115                 120                 125

Pro Lys Val Thr Phe Thr Val Glu Lys Gly Ser Asn Glu Lys His Leu
130                 135                 140

Ala Val Leu Val Lys Tyr Glu Gly Asp Thr Met Ala Glu Val Glu Leu
145                 150                 155                 160

Arg Glu His Gly Ser Asp Glu Trp Val Ala Met Thr Lys Gly Glu Gly
                165                 170                 175

Ser Gly Arg Gly Cys Gly Ser Cys Phe Glu Ile Lys Cys Thr Lys Pro
            180                 185                 190

Glu Ala Cys Ser Gly Glu Pro Val Val His Ile Thr Asp Asp Asn
                195                 200                 205

Glu Glu Pro Ile Ala Pro Tyr His Phe Asp Leu Ser Gly His Ala Phe
210                 215                 220

Gly Ala Met Ala Lys Lys Gly Asp Glu Gln Lys Leu Arg Thr Gly Pro
225                 230                 235                 240

Phe Thr Val Arg Tyr Thr Thr Glu Gly Gly Thr Lys Thr Glu Ala Glu
                245                 250                 255

Asp Val Ile Pro Glu Gly Trp Lys Ala Asp Thr Ser Tyr Glu Ser Lys
                260                 265                 270

Gly Ala Ala Ser Asn Lys Ala Phe Ala Glu Gly Leu Ser Gly Glu Pro
            275                 280                 285

Lys Gly Ala Ala Glu Ser Ser Lys Ala Ala Leu Thr Ser Lys Leu
290                 295                 300

Asp Ala Ala Tyr Lys Leu Ala Tyr Lys Thr Ala Glu Gly Ala Thr Pro
305                 310                 315                 320

Glu Ala Lys Tyr Asp Ala Tyr Val Ala Thr Leu Ser Glu Ala Leu Arg
                325                 330                 335

Ile Ile Ala Gly Thr Leu Glu Val His Ala Val Lys Pro Ala Ala Asp
                340                 345                 350

Leu Gly Tyr Gly Pro Ala Thr Pro Ala Ala Pro Ala Ala Gly Tyr Thr
                355                 360                 365

Pro Ala Thr Pro Ala Ala Pro Ala Glu Ala Ala Pro Ala Gly Lys Ala
370                 375                 380

Thr Thr Glu Glu Gln Lys Leu Ile Glu Lys Ile Asn Ala Gly Phe Lys
385                 390                 395                 400

Ala Ala Leu Ala Ala Ala Gly Val Gln Pro Ala Asp Lys Tyr Arg
                405                 410                 415

Thr Phe Val Ala Thr Phe Ala Val Lys Gln Ala Tyr Ala Thr Val
                420                 425                 430

Ala Thr Ala Pro Glu Val Lys Tyr Thr Val Phe Glu Thr Ala Leu Lys
                435                 440                 445

Lys Ala Ile Thr Ala Met Ser Glu Ala Gln Lys Ala Lys Pro Ala
            450                 455                 460

Ala Ala Ala Thr Ala Thr Ala Thr Ala Ala Val Gly Ala Ala Thr Gly
465                 470                 475                 480

Ala Ala Thr Ala Ala Thr Gly Gly Tyr Lys Val Ala Glu Glu Val Lys
                485                 490                 495

Val Ile Pro Ala Gly Glu Leu Gln Val Ile Glu Lys Val Asp Ala Ala
                500                 505                 510
```

```
Phe Lys Val Ala Ala Thr Ala Ala Asn Ala Ala Pro Ala Asn Asp Lys
            515                 520                 525

Phe Thr Val Phe Glu Ala Ala Phe Asn Asp Ala Ile Lys Ala Ser Thr
        530                 535                 540

Gly Gly Ala Tyr Glu Ser Tyr Lys Phe Ile Pro Ala Leu Glu Ala Ile
545                 550                 555                 560

Pro Lys Val Pro Pro Gly Pro Asn Ile Thr Ala Thr Tyr Gly Asp Lys
                565                 570                 575

Trp Leu Asp Ala Lys Ser Thr Trp Tyr Gly Lys Pro Thr Gly Ala Gly
            580                 585                 590

Pro Lys Asp Asn Gly Gly Ala Cys Gly Tyr Lys Asp Val Asp Lys Pro
        595                 600                 605

Pro Phe Ser Gly Met Thr Gly Cys Gly Asn Thr Pro Ile Phe Lys Ser
        610                 615                 620

Ala Gly Glu Leu Glu Leu Gln Phe Arg Arg Val Lys Cys Lys Tyr Pro
625                 630                 635                 640

Glu Gly Thr Lys Val Thr Phe His Val Glu Lys Gly Ser Asn Pro Asn
                645                 650                 655

Tyr Leu Ala Leu Leu Val Lys Tyr Val Asn Gly Asp Gly Asp Val Val
            660                 665                 670

Ala Val Asp Ile Lys Glu Lys Gly Lys Asp Lys Trp Ile Glu Leu Lys
        675                 680                 685

Glu Ser Trp Gly Ala Ile Trp Arg Ile Asp Thr Pro Asp Lys Leu
        690                 695                 700

<210> SEQ ID NO 34
<211> LENGTH: 703
<212> TYPE: PRT
<213> ORGANISM: Artificial Sequence
<220> FEATURE:
<223> OTHER INFORMATION: construct N without N-terminal Met and
      C-terminal hexahistidine

<400> SEQUENCE: 34

Ala Asp Lys Tyr Lys Thr Phe Glu Ala Ala Phe Thr Val Ser Ser Lys
1               5                   10                  15

Arg Asn Leu Ala Asp Ala Val Ser Lys Ala Pro Gln Leu Val Pro Lys
            20                  25                  30

Leu Asp Glu Val Tyr Asn Ala Ala Tyr Asn Ala Ala Asp His Ala Ala
        35                  40                  45

Pro Glu Asp Lys Tyr Glu Ala Phe Val Leu His Phe Ser Glu Ala Leu
    50                  55                  60

Arg Ile Ile Ala Gly Thr Pro Glu Val His Ala Val Lys Pro Gly Ala
65                  70                  75                  80

Val Pro Lys Val Thr Phe Thr Val Glu Lys Gly Ser Asn Glu Lys His
            85                  90                  95

Leu Ala Val Leu Val Lys Tyr Glu Gly Asp Thr Met Ala Glu Val Glu
        100                 105                 110

Leu Phe Arg Phe Leu Thr Glu Lys Gly Met Lys Asn Val Phe Asp Asp
    115                 120                 125

Val Val Pro Glu Lys Tyr Thr Ile Gly Ala Thr Tyr Ala Pro Glu Glu
    130                 135                 140

Arg Glu His Gly Ser Asp Glu Trp Val Ala Met Thr Lys Gly Glu Gly
145                 150                 155                 160

Gly Val Trp Thr Phe Asp Ser Glu Glu Pro Leu Gln Gly Pro Phe Asn
                165                 170                 175
```

```
Gly Ala Ala Ser Asn Lys Ala Phe Ala Glu Gly Leu Ser Gly Glu Pro
            180                 185                 190
Lys Gly Ala Ala Glu Ser Ser Lys Ala Ala Leu Thr Ser Lys Leu
            195                 200                 205
Asp Ala Ala Tyr Lys Leu Ala Tyr Lys Thr Ala Glu Gly Ala Thr Pro
210                 215                 220
Glu Ala Lys Tyr Asp Ala Tyr Val Ala Thr Leu Ser Glu Ala Leu Arg
225                 230                 235                 240
Ile Ile Ala Gly Thr Leu Glu Val His Ala Val Lys Pro Ala Ala Asp
                245                 250                 255
Leu Gly Tyr Gly Pro Ala Thr Pro Ala Ala Pro Ala Ala Gly Tyr Thr
            260                 265                 270
Pro Ala Thr Pro Ala Ala Pro Ala Glu Ala Ala Pro Ala Gly Lys Ala
            275                 280                 285
Thr Thr Glu Glu Gln Lys Leu Ile Glu Lys Ile Asn Ala Gly Phe Lys
290                 295                 300
Ala Ala Leu Ala Ala Ala Gly Val Gln Pro Ala Asp Lys Tyr Arg
305                 310                 315                 320
Thr Phe Val Ala Thr Phe Ala Val Lys Gln Ala Tyr Ala Thr Val
                325                 330                 335
Ala Thr Ala Pro Glu Val Lys Tyr Thr Val Phe Glu Thr Ala Leu Lys
            340                 345                 350
Lys Ala Ile Thr Ala Met Ser Glu Ala Gln Lys Ala Ala Lys Pro Ala
            355                 360                 365
Ala Ala Ala Thr Ala Thr Ala Thr Ala Ala Val Gly Ala Ala Thr Gly
            370                 375                 380
Ala Ala Thr Ala Ala Thr Gly Gly Tyr Lys Val Ala Glu Glu Val Lys
385                 390                 395                 400
Val Ile Pro Ala Gly Glu Leu Gln Val Ile Glu Lys Val Asp Ala Ala
                405                 410                 415
Phe Lys Val Ala Ala Thr Ala Ala Asn Ala Ala Pro Ala Asn Asp Lys
            420                 425                 430
Phe Thr Val Phe Glu Ala Ala Phe Asn Asp Ala Ile Lys Ala Ser Thr
            435                 440                 445
Gly Gly Ala Tyr Glu Ser Tyr Lys Phe Ile Pro Ala Leu Glu Ala Ser
            450                 455                 460
Gly Arg Gly Cys Gly Ser Cys Phe Glu Ile Lys Cys Thr Lys Pro Glu
465                 470                 475                 480
Ala Cys Ser Gly Glu Pro Val Val His Ile Thr Asp Asp Asn Glu
                485                 490                 495
Glu Pro Ile Ala Pro Tyr His Phe Asp Leu Ser Gly His Ala Phe Gly
            500                 505                 510
Ala Met Ala Lys Lys Gly Asp Glu Gln Lys Leu Arg Thr Gly Pro Phe
            515                 520                 525
Thr Val Arg Tyr Thr Thr Glu Gly Gly Thr Lys Thr Glu Ala Glu Asp
            530                 535                 540
Val Ile Pro Glu Gly Trp Lys Ala Asp Thr Ser Tyr Glu Ser Lys Ile
545                 550                 555                 560
Pro Lys Val Pro Pro Gly Pro Asn Ile Thr Ala Thr Tyr Gly Asp Lys
                565                 570                 575
Trp Leu Asp Ala Lys Ser Thr Trp Tyr Gly Lys Pro Thr Gly Ala Gly
            580                 585                 590
```

```
Pro Lys Asp Asn Gly Gly Ala Cys Gly Tyr Lys Asp Val Asp Lys Pro
            595                 600                 605

Pro Phe Ser Gly Met Thr Gly Cys Gly Asn Thr Pro Ile Phe Lys Ser
    610                 615                 620

Ala Gly Glu Leu Glu Leu Gln Phe Arg Arg Val Lys Cys Lys Tyr Pro
625                 630                 635                 640

Glu Gly Thr Lys Val Thr Phe His Val Glu Lys Gly Ser Asn Pro Asn
                645                 650                 655

Tyr Leu Ala Leu Leu Val Lys Tyr Val Asn Gly Asp Gly Asp Val Val
            660                 665                 670

Ala Val Asp Ile Lys Glu Lys Gly Lys Asp Lys Trp Ile Glu Leu Lys
    675                 680                 685

Glu Ser Trp Gly Ala Ile Trp Arg Ile Asp Thr Pro Asp Lys Leu
    690                 695                 700

<210> SEQ ID NO 35
<211> LENGTH: 527
<212> TYPE: PRT
<213> ORGANISM: Artificial Sequence
<220> FEATURE:
<223> OTHER INFORMATION: construct O without N-terminal Met and
      C-terminal hexahistidine

<400> SEQUENCE: 35

Gly Ala Ala Ser Asn Lys Ala Phe Ala Glu Gly Leu Ser Gly Glu Pro
1               5                   10                  15

Lys Gly Ala Ala Glu Ser Ser Lys Ala Ala Leu Thr Ser Lys Leu
            20                  25                  30

Asp Ala Ala Tyr Lys Leu Ala Tyr Lys Thr Ala Glu Gly Ala Thr Pro
            35                  40                  45

Glu Ala Lys Tyr Asp Ala Tyr Val Ala Thr Leu Ser Glu Ala Leu Arg
50                  55                  60

Ile Ile Ala Gly Thr Leu Glu Val His Ala Val Lys Pro Ala Ala Asp
65                  70                  75                  80

Leu Gly Tyr Gly Pro Ala Thr Pro Ala Ala Pro Ala Ala Gly Tyr Thr
            85                  90                  95

Pro Ala Thr Pro Ala Ala Pro Ala Glu Ala Ala Pro Ala Gly Lys Ala
            100                 105                 110

Thr Thr Glu Glu Gln Lys Leu Ile Glu Lys Ile Asn Ala Gly Phe Lys
            115                 120                 125

Ala Ala Leu Ala Ala Ala Gly Val Gln Pro Ala Asp Lys Tyr Arg
            130                 135                 140

Thr Phe Val Ala Thr Phe Ser Gly Arg Gly Cys Gly Ser Cys Phe Glu
145                 150                 155                 160

Ile Lys Cys Thr Lys Pro Glu Ala Cys Ser Gly Glu Pro Val Val Val
                165                 170                 175

His Ile Thr Asp Asp Asn Glu Glu Pro Ile Ala Pro Tyr His Phe Asp
            180                 185                 190

Leu Ser Gly His Ala Phe Gly Ala Met Ala Lys Lys Gly Asp Glu Gln
            195                 200                 205

Lys Leu Arg Thr Gly Pro Phe Thr Val Arg Tyr Thr Thr Glu Gly Gly
    210                 215                 220

Thr Lys Thr Glu Ala Glu Asp Val Ile Pro Glu Gly Trp Lys Ala Asp
225                 230                 235                 240

Thr Ser Tyr Glu Ser Lys Ala Glu Glu Val Lys Val Ile Pro Ala Gly
            245                 250                 255
```

```
Glu Leu Gln Val Ile Glu Lys Val Asp Ala Ala Phe Lys Val Ala Ala
            260                 265                 270

Thr Ala Ala Asn Ala Ala Pro Ala Val Lys Gln Ala Tyr Ala Ala
        275                 280                 285

Thr Val Ala Thr Ala Pro Glu Val Lys Tyr Thr Val Phe Glu Thr Ala
    290                 295                 300

Leu Lys Lys Ala Ile Thr Ala Met Ser Glu Ala Gln Lys Ala Ala Lys
305                 310                 315                 320

Pro Ala Ala Ala Ala Thr Ala Thr Ala Thr Ala Ala Val Gly Ala Ala
                325                 330                 335

Thr Gly Ala Ala Thr Ala Ala Thr Gly Gly Tyr Lys Val Asn Asp Lys
            340                 345                 350

Phe Thr Val Phe Glu Ala Ala Phe Asn Asp Ala Ile Lys Ala Ser Thr
        355                 360                 365

Gly Gly Ala Tyr Glu Ser Tyr Lys Phe Ile Pro Ala Leu Glu Ala Ser
    370                 375                 380

Ala Gly Glu Leu Glu Leu Gln Phe Arg Arg Val Lys Cys Lys Tyr Pro
385                 390                 395                 400

Glu Gly Thr Lys Val Thr Phe His Val Glu Lys Gly Ser Asn Pro Asn
                405                 410                 415

Tyr Leu Ala Leu Leu Val Ile Pro Lys Val Pro Pro Gly Pro Asn Ile
            420                 425                 430

Thr Ala Thr Tyr Gly Asp Lys Trp Leu Asp Ala Lys Ser Thr Trp Tyr
        435                 440                 445

Gly Lys Pro Thr Gly Ala Gly Pro Lys Asp Asn Gly Gly Ala Cys Gly
    450                 455                 460

Tyr Lys Asp Val Asp Lys Pro Pro Phe Ser Gly Met Thr Gly Cys Gly
465                 470                 475                 480

Asn Thr Pro Ile Phe Lys Lys Tyr Val Asn Gly Asp Gly Asp Val Val
                485                 490                 495

Ala Val Asp Ile Lys Glu Lys Gly Lys Asp Lys Trp Ile Glu Leu Lys
            500                 505                 510

Glu Ser Trp Gly Ala Ile Trp Arg Ile Asp Thr Pro Asp Lys Leu
        515                 520                 525

<210> SEQ ID NO 36
<211> LENGTH: 527
<212> TYPE: PRT
<213> ORGANISM: Artificial Sequence
<220> FEATURE:
<223> OTHER INFORMATION: construct P without N-terminal Met and
      C-terminal hexahistidine

<400> SEQUENCE: 36

Gly Ala Ala Ser Asn Lys Ala Phe Ala Glu Gly Leu Ser Gly Glu Pro
1               5                   10                  15

Lys Gly Ala Ala Glu Ser Ser Ser Lys Ala Ala Leu Thr Ser Lys Leu
            20                  25                  30

Asp Ala Ala Tyr Lys Leu Ala Tyr Lys Thr Ala Glu Gly Ala Thr Pro
        35                  40                  45

Glu Ala Lys Tyr Asp Ala Tyr Val Ala Thr Leu Ser Glu Ala Leu Arg
    50                  55                  60

Ile Ile Ala Gly Thr Leu Glu Val His Ala Val Lys Pro Ala Ala Asp
65                  70                  75                  80

Leu Gly Tyr Gly Pro Ala Thr Pro Ala Ala Pro Ala Ala Gly Tyr Thr
```

```
                         85                  90                  95
Pro Ala Thr Pro Ala Ala Pro Ala Glu Ala Pro Ala Gly Lys Ala
                100                 105                 110

Thr Thr Glu Glu Gln Lys Leu Ile Glu Lys Ile Asn Ala Gly Phe Lys
            115                 120                 125

Ala Ala Leu Ala Ala Ala Gly Val Gln Pro Ala Asp Lys Tyr Arg
        130                 135                 140

Thr Phe Val Ala Thr Phe Ser Gly Arg Gly Cys Gly Ser Cys Phe Glu
145                 150                 155                 160

Ile Lys Cys Thr Lys Pro Glu Ala Cys Ser Gly Glu Pro Val Val Val
                165                 170                 175

His Ile Thr Asp Asp Asn Glu Glu Pro Ile Ala Pro Tyr His Phe Asp
            180                 185                 190

Leu Ser Gly His Ala Phe Gly Ala Met Ala Lys Gly Asp Glu Gln
        195                 200                 205

Lys Leu Arg Thr Gly Pro Phe Thr Val Arg Tyr Thr Thr Glu Gly Gly
    210                 215                 220

Thr Lys Thr Glu Ala Glu Asp Val Ile Pro Glu Gly Trp Lys Ala Asp
225                 230                 235                 240

Thr Ser Tyr Glu Ser Lys Ala Glu Glu Val Lys Val Ile Pro Ala Gly
                245                 250                 255

Glu Leu Gln Val Ile Glu Lys Val Asp Ala Ala Phe Lys Val Ala Ala
            260                 265                 270

Thr Ala Ala Asn Ala Ala Pro Ala Ala Val Lys Gln Ala Tyr Ala Ala
        275                 280                 285

Thr Val Ala Thr Ala Pro Glu Val Lys Tyr Thr Val Phe Glu Thr Ala
        290                 295                 300

Leu Lys Lys Ala Ile Thr Ala Met Ser Glu Ala Gln Lys Ala Ala Lys
305                 310                 315                 320

Pro Ala Ala Ala Ala Thr Ala Thr Ala Thr Ala Val Gly Ala Ala
                325                 330                 335

Thr Gly Ala Ala Thr Ala Ala Thr Gly Gly Tyr Lys Val Asn Asp Lys
        340                 345                 350

Phe Thr Val Phe Glu Ala Ala Phe Asn Asp Ala Ile Lys Ala Ser Thr
    355                 360                 365

Gly Gly Ala Tyr Glu Ser Tyr Lys Phe Ile Pro Ala Leu Glu Ala Ile
    370                 375                 380

Pro Lys Val Pro Pro Gly Pro Asn Ile Thr Ala Thr Tyr Gly Asp Lys
385                 390                 395                 400

Trp Leu Asp Ala Lys Ser Thr Trp Tyr Gly Lys Pro Thr Gly Ala Ser
                405                 410                 415

Ala Gly Glu Leu Glu Leu Gln Phe Arg Arg Val Lys Cys Lys Tyr Pro
            420                 425                 430

Glu Gly Thr Lys Val Thr Phe His Val Glu Lys Gly Ser Asn Pro Asn
        435                 440                 445

Tyr Leu Ala Leu Leu Val Lys Tyr Val Asn Gly Asp Gly Val Val
        450                 455                 460

Ala Val Asp Ile Lys Glu Lys Gly Lys Asp Lys Trp Ile Glu Leu Lys
465                 470                 475                 480

Glu Ser Trp Gly Ala Ile Trp Arg Ile Asp Thr Pro Asp Lys Leu Gly
                485                 490                 495

Pro Lys Asp Asn Gly Gly Ala Cys Gly Tyr Lys Asp Val Asp Lys Pro
            500                 505                 510
```

```
Pro Phe Ser Gly Met Thr Gly Cys Gly Asn Thr Pro Ile Phe Lys
        515                 520                 525
```

<210> SEQ ID NO 37
<211> LENGTH: 176
<212> TYPE: PRT
<213> ORGANISM: Artificial Sequence
<220> FEATURE:
<223> OTHER INFORMATION: construct Q without N-terminal Met and
      C-terminal hexahistidine

<400> SEQUENCE: 37

```
Phe Arg Phe Leu Thr Glu Lys Gly Met Lys Asn Val Phe Asp Asp Val
1               5                   10                  15

Val Pro Glu Lys Tyr Thr Ile Gly Ala Thr Tyr Ala Pro Glu Glu Asp
            20                  25                  30

Glu Trp Val Ala Met Thr Lys Gly Glu Gly Gly Val Trp Thr Phe Asp
        35                  40                  45

Ser Glu Glu Pro Leu Gln Gly Pro Phe Asn Ala Asp Lys Tyr Lys Thr
    50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95

Ala Ala Tyr Asn Ala Ala Asp His Ala Pro Glu Asp Lys Tyr Glu
            100                 105                 110

Ala Phe Val Leu His Phe Ser Glu Ala Leu Arg Ile Ile Ala Gly Thr
        115                 120                 125

Pro Glu Val His Ala Val Lys Pro Gly Ala Val Pro Lys Val Thr Phe
    130                 135                 140

Thr Val Glu Lys Gly Ser Asn Glu Lys His Leu Ala Val Leu Val Lys
145                 150                 155                 160

Tyr Glu Gly Asp Thr Met Ala Glu Val Glu Leu Arg Glu His Gly Ser
                165                 170                 175
```

<210> SEQ ID NO 38
<211> LENGTH: 253
<212> TYPE: PRT
<213> ORGANISM: Artificial Sequence
<220> FEATURE:
<223> OTHER INFORMATION: construct A with N-terminal Met and C-terminal
      hexahistidine

<400> SEQUENCE: 38

```
Met Ser Gly Arg Gly Cys Gly Ser Cys Phe Glu Ile Lys Cys Thr Lys
1               5                   10                  15

Pro Glu Ala Cys Ser Gly Glu Pro Val Val His Ile Thr Asp Asp
            20                  25                  30

Asn Glu Glu Pro Ile Ala Pro Tyr His Phe Asp Leu Ser Gly His Ala
        35                  40                  45

Phe Gly Ala Met Ala Lys Lys Gly Asp Glu Gln Lys Leu Arg Thr Gly
    50                  55                  60

Pro Phe Thr Val Arg Tyr Thr Thr Glu Gly Gly Thr Lys Thr Glu Ala
65                  70                  75                  80

Glu Asp Val Ile Pro Glu Gly Trp Lys Ala Asp Thr Ser Tyr Glu Ser
                85                  90                  95

Lys Gly Ala Ala Ser Asn Lys Ala Phe Ala Glu Gly Leu Ser Gly Glu
            100                 105                 110
```

```
Pro Lys Gly Ala Ala Glu Ser Ser Lys Ala Ala Leu Thr Ser Lys
        115                 120                 125

Leu Asp Ala Ala Tyr Lys Leu Ala Tyr Lys Thr Ala Glu Gly Ala Thr
    130                 135                 140

Pro Glu Ala Lys Tyr Asp Ala Tyr Val Ala Thr Leu Ser Glu Ala Leu
145                 150                 155                 160

Arg Ile Ile Ala Gly Thr Leu Glu Val His Ala Val Lys Pro Ala Ala
                165                 170                 175

Asp Leu Gly Tyr Gly Pro Ala Thr Pro Ala Ala Pro Ala Ala Gly Tyr
            180                 185                 190

Thr Pro Ala Thr Pro Ala Ala Pro Ala Glu Ala Ala Pro Ala Gly Lys
        195                 200                 205

Ala Thr Thr Glu Glu Gln Lys Leu Ile Glu Lys Ile Asn Ala Gly Phe
    210                 215                 220

Lys Ala Ala Leu Ala Ala Ala Gly Val Gln Pro Ala Asp Lys Tyr
225                 230                 235                 240

Arg Thr Phe Val Ala Thr Phe His His His His His His
                245                 250

<210> SEQ ID NO 39
<211> LENGTH: 288
<212> TYPE: PRT
<213> ORGANISM: Artificial Sequence
<220> FEATURE:
<223> OTHER INFORMATION: construct B with N-terminal Met and C-terminal
      hexahistidine

<400> SEQUENCE: 39

Met Ala Val Lys Gln Ala Tyr Ala Ala Thr Val Ala Thr Ala Pro Glu
1               5                   10                  15

Val Lys Tyr Thr Val Phe Glu Thr Ala Leu Lys Lys Ala Ile Thr Ala
            20                  25                  30

Met Ser Glu Ala Gln Lys Ala Ala Lys Pro Ala Ala Ala Ala Thr Ala
        35                  40                  45

Thr Ala Thr Ala Ala Val Gly Ala Ala Thr Gly Ala Ala Thr Ala Ala
    50                  55                  60

Thr Gly Gly Tyr Lys Val Ala Glu Glu Val Lys Val Ile Pro Ala Gly
65                  70                  75                  80

Glu Leu Gln Val Ile Glu Lys Val Asp Ala Ala Phe Lys Val Ala Ala
                85                  90                  95

Thr Ala Ala Asn Ala Ala Pro Ala Asn Asp Lys Phe Thr Val Phe Glu
            100                 105                 110

Ala Ala Phe Asn Asp Ala Ile Lys Ala Ser Thr Gly Gly Ala Tyr Glu
        115                 120                 125

Ser Tyr Lys Phe Ile Pro Ala Leu Glu Ala Ile Pro Lys Val Pro Pro
    130                 135                 140

Gly Pro Asn Ile Thr Ala Thr Tyr Gly Asp Lys Trp Leu Asp Ala Lys
145                 150                 155                 160

Ser Thr Trp Tyr Gly Lys Pro Thr Gly Ala Gly Pro Lys Asp Asn Gly
                165                 170                 175

Gly Ala Cys Gly Tyr Lys Asp Val Asp Lys Pro Pro Phe Ser Gly Met
            180                 185                 190

Thr Gly Cys Gly Asn Thr Pro Ile Phe Lys Ser Ala Gly Glu Leu Glu
        195                 200                 205

Leu Gln Phe Arg Arg Val Lys Cys Lys Tyr Pro Glu Gly Thr Lys Val
```

```
            210                 215                 220
Thr Phe His Val Glu Lys Gly Ser Asn Pro Asn Tyr Leu Ala Leu Leu
225                 230                 235                 240

Val Lys Tyr Val Asn Gly Asp Gly Asp Val Ala Val Asp Ile Lys
                245                 250                 255

Glu Lys Gly Lys Asp Lys Trp Ile Glu Leu Lys Glu Ser Trp Gly Ala
                260                 265                 270

Ile Trp Arg Ile Asp Thr Pro Asp Lys Leu His His His His His His
            275                 280                 285

<210> SEQ ID NO 40
<211> LENGTH: 253
<212> TYPE: PRT
<213> ORGANISM: Artificial Sequence
<220> FEATURE:
<223> OTHER INFORMATION: construct C with N-terminal Met and C-terminal
      hexahistidine

<400> SEQUENCE: 40

Met Gly Ala Ala Ser Asn Lys Ala Phe Ala Glu Gly Leu Ser Gly Glu
1               5                   10                  15

Pro Lys Gly Ala Ala Glu Ser Ser Lys Ala Ala Leu Thr Ser Lys
            20                  25                  30

Leu Asp Ala Ala Tyr Lys Leu Ala Tyr Lys Thr Ala Glu Gly Ala Thr
            35                  40                  45

Pro Glu Ala Lys Tyr Asp Ala Tyr Val Ala Thr Leu Ser Glu Ala Leu
50                  55                  60

Arg Ile Ile Ala Gly Thr Leu Glu Val His Ala Val Lys Pro Ala Ala
65                  70                  75                  80

Asp Leu Gly Tyr Gly Pro Ala Thr Pro Ala Ala Pro Ala Ala Gly Tyr
                85                  90                  95

Thr Pro Ala Thr Pro Ala Ala Pro Ala Glu Ala Ala Pro Ala Gly Lys
            100                 105                 110

Ala Thr Thr Glu Glu Gln Lys Leu Ile Glu Lys Ile Asn Ala Gly Phe
            115                 120                 125

Lys Ala Ala Leu Ala Ala Ala Gly Val Gln Pro Ala Asp Lys Tyr
130                 135                 140

Arg Thr Phe Val Ala Thr Phe Ser Gly Arg Gly Cys Gly Ser Cys Phe
145                 150                 155                 160

Glu Ile Lys Cys Thr Lys Pro Glu Ala Cys Ser Gly Glu Pro Val Val
                165                 170                 175

Val His Ile Thr Asp Asp Asn Glu Glu Pro Ile Ala Pro Tyr His Phe
            180                 185                 190

Asp Leu Ser Gly His Ala Phe Gly Ala Met Ala Lys Lys Gly Asp Glu
            195                 200                 205

Gln Lys Leu Arg Thr Gly Pro Phe Thr Val Arg Tyr Thr Thr Glu Gly
            210                 215                 220

Gly Thr Lys Thr Glu Ala Glu Asp Val Ile Pro Glu Gly Trp Lys Ala
225                 230                 235                 240

Asp Thr Ser Tyr Glu Ser Lys His His His His His
                245                 250

<210> SEQ ID NO 41
<211> LENGTH: 288
<212> TYPE: PRT
<213> ORGANISM: Artificial Sequence
<220> FEATURE:
```

<223> OTHER INFORMATION: construct D with N-terminal Met and C-terminal hexahistidine

<400> SEQUENCE: 41

| Met | Ile | Pro | Lys | Val | Pro | Pro | Gly | Pro | Asn | Ile | Thr | Ala | Thr | Tyr | Gly |
|---|---|---|---|---|---|---|---|---|---|---|---|---|---|---|---|
| 1 | | | | 5 | | | | | 10 | | | | | 15 | |

Asp Lys Trp Leu Asp Ala Lys Ser Thr Trp Tyr Gly Lys Pro Thr Gly
            20                  25                  30

Ala Gly Pro Lys Asp Asn Gly Gly Ala Cys Gly Tyr Lys Asp Val Asp
        35                  40                  45

Lys Pro Pro Phe Ser Gly Met Thr Gly Cys Gly Asn Thr Pro Ile Phe
    50                  55                  60

Lys Ser Ala Gly Glu Leu Glu Leu Gln Phe Arg Arg Val Lys Cys Lys
65                  70                  75                  80

Tyr Pro Glu Gly Thr Lys Val Thr Phe His Val Glu Lys Gly Ser Asn
                85                  90                  95

Pro Asn Tyr Leu Ala Leu Leu Val Lys Tyr Val Asn Gly Asp Gly Asp
            100                 105                 110

Val Val Ala Val Asp Ile Lys Glu Lys Gly Lys Asp Lys Trp Ile Glu
        115                 120                 125

Leu Lys Glu Ser Trp Gly Ala Ile Trp Arg Ile Asp Thr Pro Asp Lys
    130                 135                 140

Leu Ala Val Lys Gln Ala Tyr Ala Ala Thr Val Ala Thr Ala Pro Glu
145                 150                 155                 160

Val Lys Tyr Thr Val Phe Glu Thr Ala Leu Lys Lys Ala Ile Thr Ala
                165                 170                 175

Met Ser Glu Ala Gln Lys Ala Ala Lys Pro Ala Ala Ala Ala Thr Ala
            180                 185                 190

Thr Ala Thr Ala Ala Val Gly Ala Ala Thr Gly Ala Ala Thr Ala Ala
        195                 200                 205

Thr Gly Gly Tyr Lys Val Ala Glu Glu Val Lys Val Ile Pro Ala Gly
    210                 215                 220

Glu Leu Gln Val Ile Glu Lys Val Asp Ala Ala Phe Lys Val Ala Ala
225                 230                 235                 240

Thr Ala Ala Asn Ala Ala Pro Ala Asn Asp Lys Phe Thr Val Phe Glu
                245                 250                 255

Ala Ala Phe Asn Asp Ala Ile Lys Ala Ser Thr Gly Ala Tyr Glu
            260                 265                 270

Ser Tyr Lys Phe Ile Pro Ala Leu Glu Ala His His His His His His
        275                 280                 285

<210> SEQ ID NO 42
<211> LENGTH: 301
<212> TYPE: PRT
<213> ORGANISM: Artificial Sequence
<220> FEATURE:
<223> OTHER INFORMATION: construct E with N-terminal Met and C-terminal hexahistidine

<400> SEQUENCE: 42

Met Gly Ala Ala Ser Asn Lys Ala Phe Ala Glu Gly Leu Ser Gly Glu
1               5                   10                  15

Pro Lys Gly Ala Ala Glu Ser Ser Lys Ala Ala Leu Thr Ser Lys
            20                  25                  30

Leu Asp Ala Ala Tyr Lys Leu Ala Tyr Lys Thr Ala Glu Gly Ala Thr
        35                  40                  45

-continued

Pro Glu Ala Lys Tyr Asp Ala Tyr Val Ala Thr Leu Ser Glu Ala Leu
    50                  55                  60

Arg Ile Ile Ala Gly Thr Leu Glu Val His Ala Val Lys Pro Ala Ala
65                  70                  75                  80

Asp Leu Gly Tyr Gly Pro Ala Thr Pro Ala Ala Pro Ala Ala Gly Tyr
                85                  90                  95

Thr Pro Ala Thr Pro Ala Ala Pro Ala Glu Ala Ala Pro Ala Gly Lys
            100                 105                 110

Ala Thr Thr Glu Glu Gln Lys Leu Ile Glu Lys Ile Asn Ala Gly Phe
            115                 120                 125

Lys Ala Ala Leu Ala Ala Ala Gly Val Gln Pro Ala Asp Lys Tyr
130                 135                 140

Arg Thr Phe Val Ala Thr Phe Ile Pro Lys Val Pro Pro Gly Pro Asn
145                 150                 155                 160

Ile Thr Ala Thr Tyr Gly Asp Lys Trp Leu Asp Ala Lys Ser Thr Trp
                165                 170                 175

Tyr Gly Lys Pro Thr Gly Ala Gly Pro Lys Asp Asn Gly Gly Ala Cys
            180                 185                 190

Gly Tyr Lys Asp Val Asp Lys Pro Phe Ser Gly Met Thr Gly Cys
            195                 200                 205

Gly Asn Thr Pro Ile Phe Lys Ser Ala Gly Glu Leu Glu Leu Gln Phe
    210                 215                 220

Arg Arg Val Lys Cys Lys Tyr Pro Glu Gly Thr Lys Val Thr Phe His
225                 230                 235                 240

Val Glu Lys Gly Ser Asn Pro Asn Tyr Leu Ala Leu Leu Val Lys Tyr
                245                 250                 255

Val Asn Gly Asp Gly Asp Val Val Ala Val Asp Ile Lys Glu Lys Gly
            260                 265                 270

Lys Asp Lys Trp Ile Glu Leu Lys Glu Ser Trp Gly Ala Ile Trp Arg
    275                 280                 285

Ile Asp Thr Pro Asp Lys Leu His His His His His
    290                 295                 300

<210> SEQ ID NO 43
<211> LENGTH: 301
<212> TYPE: PRT
<213> ORGANISM: Artificial Sequence
<220> FEATURE:
<223> OTHER INFORMATION: construct F with N-terminal Met and C-terminal
      hexahistidine

<400> SEQUENCE: 43

Met Ile Pro Lys Val Pro Pro Gly Pro Asn Ile Thr Ala Thr Tyr Gly
1               5                   10                  15

Asp Lys Trp Leu Asp Ala Lys Ser Thr Trp Tyr Gly Lys Pro Thr Gly
                20                  25                  30

Ala Gly Pro Lys Asp Asn Gly Gly Ala Cys Gly Tyr Lys Asp Val Asp
            35                  40                  45

Lys Pro Pro Phe Ser Gly Met Thr Gly Cys Gly Asn Thr Pro Ile Phe
    50                  55                  60

Lys Ser Ala Gly Glu Leu Glu Leu Gln Phe Arg Arg Val Lys Cys Lys
65                  70                  75                  80

Tyr Pro Glu Gly Thr Lys Val Thr Phe His Val Glu Lys Gly Ser Asn
                85                  90                  95

Pro Asn Tyr Leu Ala Leu Leu Val Lys Tyr Val Asn Gly Asp Gly Asp
            100                 105                 110

```
Val Val Ala Val Asp Ile Lys Glu Lys Gly Lys Asp Lys Trp Ile Glu
            115                 120                 125

Leu Lys Glu Ser Trp Gly Ala Ile Trp Arg Ile Asp Thr Pro Asp Lys
        130                 135                 140

Leu Gly Ala Ala Ser Asn Lys Ala Phe Ala Glu Gly Leu Ser Gly Glu
145                 150                 155                 160

Pro Lys Gly Ala Ala Glu Ser Ser Lys Ala Ala Leu Thr Ser Lys
                165                 170                 175

Leu Asp Ala Ala Tyr Lys Leu Ala Tyr Lys Thr Ala Glu Gly Ala Thr
                180                 185                 190

Pro Glu Ala Lys Tyr Asp Ala Tyr Val Ala Thr Leu Ser Glu Ala Leu
            195                 200                 205

Arg Ile Ile Ala Gly Thr Leu Glu Val His Ala Val Lys Pro Ala Ala
            210                 215                 220

Asp Leu Gly Tyr Gly Pro Ala Thr Pro Ala Ala Pro Ala Ala Gly Tyr
225                 230                 235                 240

Thr Pro Ala Thr Pro Ala Ala Pro Ala Glu Ala Ala Pro Ala Gly Lys
                245                 250                 255

Ala Thr Thr Glu Glu Gln Lys Leu Ile Glu Lys Ile Asn Ala Gly Phe
                260                 265                 270

Lys Ala Ala Leu Ala Ala Ala Gly Val Gln Pro Ala Asp Lys Tyr
                275                 280                 285

Arg Thr Phe Val Ala Thr Phe His His His His His His
            290                 295                 300

<210> SEQ ID NO 44
<211> LENGTH: 240
<212> TYPE: PRT
<213> ORGANISM: Artificial Sequence
<220> FEATURE:
<223> OTHER INFORMATION: construct G with N-terminal Met and C-terminal
      hexahistidine

<400> SEQUENCE: 44

Met Ser Gly Arg Gly Cys Gly Ser Cys Phe Glu Ile Lys Cys Thr Lys
1               5                   10                  15

Pro Glu Ala Cys Ser Gly Glu Pro Val Val His Ile Thr Asp Asp
            20                  25                  30

Asn Glu Glu Pro Ile Ala Pro Tyr His Phe Asp Leu Ser Gly His Ala
            35                  40                  45

Phe Gly Ala Met Ala Lys Lys Gly Asp Glu Gln Lys Leu Arg Thr Gly
        50                  55                  60

Pro Phe Thr Val Arg Tyr Thr Thr Glu Gly Gly Thr Lys Thr Glu Ala
65                  70                  75                  80

Glu Asp Val Ile Pro Glu Gly Trp Lys Ala Asp Thr Ser Tyr Glu Ser
                85                  90                  95

Lys Ala Val Lys Gln Ala Tyr Ala Ala Thr Val Ala Thr Ala Pro Glu
                100                 105                 110

Val Lys Tyr Thr Val Phe Glu Thr Ala Leu Lys Lys Ala Ile Thr Ala
            115                 120                 125

Met Ser Glu Ala Gln Lys Ala Ala Lys Pro Ala Ala Ala Thr Ala
                130                 135                 140

Thr Ala Thr Ala Ala Val Gly Ala Ala Thr Gly Ala Ala Thr Ala Ala
145                 150                 155                 160

Thr Gly Gly Tyr Lys Val Ala Glu Glu Val Lys Val Ile Pro Ala Gly
```

```
                 165                 170                 175

Glu Leu Gln Val Ile Glu Lys Val Asp Ala Ala Phe Lys Val Ala Ala
            180                 185                 190

Thr Ala Ala Asn Ala Ala Pro Ala Asn Asp Lys Phe Thr Val Phe Glu
        195                 200                 205

Ala Ala Phe Asn Asp Ala Ile Lys Ala Ser Thr Gly Gly Ala Tyr Glu
    210                 215                 220

Ser Tyr Lys Phe Ile Pro Ala Leu Glu Ala His His His His His His
225                 230                 235                 240

<210> SEQ ID NO 45
<211> LENGTH: 240
<212> TYPE: PRT
<213> ORGANISM: Artificial Sequence
<220> FEATURE:
<223> OTHER INFORMATION: construct H with N-terminal Met and C-terminal
      hexahistidine

<400> SEQUENCE: 45

Met Ala Val Lys Gln Ala Tyr Ala Ala Thr Val Ala Thr Ala Pro Glu
1               5                   10                  15

Val Lys Tyr Thr Val Phe Glu Thr Ala Leu Lys Lys Ala Ile Thr Ala
            20                  25                  30

Met Ser Glu Ala Gln Lys Ala Ala Lys Pro Ala Ala Ala Ala Thr Ala
        35                  40                  45

Thr Ala Thr Ala Ala Val Gly Ala Ala Thr Gly Ala Ala Thr Ala Ala
    50                  55                  60

Thr Gly Gly Tyr Lys Val Ala Glu Glu Val Lys Val Ile Pro Ala Gly
65                  70                  75                  80

Glu Leu Gln Val Ile Glu Lys Val Asp Ala Ala Phe Lys Val Ala Ala
                85                  90                  95

Thr Ala Ala Asn Ala Ala Pro Ala Asn Asp Lys Phe Thr Val Phe Glu
            100                 105                 110

Ala Ala Phe Asn Asp Ala Ile Lys Ala Ser Thr Gly Gly Ala Tyr Glu
        115                 120                 125

Ser Tyr Lys Phe Ile Pro Ala Leu Glu Ala Ser Gly Arg Gly Cys Gly
    130                 135                 140

Ser Cys Phe Glu Ile Lys Cys Thr Lys Pro Glu Ala Cys Ser Gly Glu
145                 150                 155                 160

Pro Val Val Val His Ile Thr Asp Asp Asn Glu Glu Pro Ile Ala Pro
                165                 170                 175

Tyr His Phe Asp Leu Ser Gly His Ala Phe Gly Ala Met Ala Lys Lys
            180                 185                 190

Gly Asp Glu Gln Lys Leu Arg Thr Gly Pro Phe Thr Val Arg Tyr Thr
        195                 200                 205

Thr Glu Gly Gly Thr Lys Thr Glu Ala Glu Asp Val Ile Pro Glu Gly
    210                 215                 220

Trp Lys Ala Asp Thr Ser Tyr Glu Ser Lys His His His His His His
225                 230                 235                 240

<210> SEQ ID NO 46
<211> LENGTH: 183
<212> TYPE: PRT
<213> ORGANISM: Artificial Sequence
<220> FEATURE:
<223> OTHER INFORMATION: construct I with N-terminal Met and C-terminal
      hexahistidine
```

```
<400> SEQUENCE: 46

Met Ala Asp Lys Tyr Lys Thr Phe Glu Ala Ala Phe Thr Val Ser Ser
1               5                   10                  15

Lys Arg Asn Leu Ala Asp Ala Val Ser Lys Ala Pro Gln Leu Val Pro
            20                  25                  30

Lys Leu Asp Glu Val Tyr Asn Ala Ala Tyr Asn Ala Ala Asp His Ala
        35                  40                  45

Ala Pro Glu Asp Lys Tyr Glu Ala Phe Val Leu His Phe Ser Glu Ala
    50                  55                  60

Leu Arg Ile Ile Ala Gly Thr Pro Glu Val His Ala Val Lys Pro Gly
65                  70                  75                  80

Ala Gly Val Trp Thr Phe Asp Ser Glu Glu Pro Leu Gln Gly Pro Phe
                85                  90                  95

Asn Phe Arg Phe Leu Thr Glu Lys Gly Met Lys Asn Val Phe Asp Asp
            100                 105                 110

Val Val Pro Glu Lys Tyr Thr Ile Gly Ala Thr Tyr Ala Pro Glu Glu
        115                 120                 125

Val Pro Lys Val Thr Phe Thr Val Glu Lys Gly Ser Asn Glu Lys His
    130                 135                 140

Leu Ala Val Leu Val Lys Tyr Glu Gly Asp Thr Met Ala Glu Val Glu
145                 150                 155                 160

Leu Arg Glu His Gly Ser Asp Glu Trp Val Ala Met Thr Lys Gly Glu
                165                 170                 175

Gly His His His His His His
            180

<210> SEQ ID NO 47
<211> LENGTH: 183
<212> TYPE: PRT
<213> ORGANISM: Artificial Sequence
<220> FEATURE:
<223> OTHER INFORMATION: construct J with N-terminal Met and C-terminal
      hexahistidine

<400> SEQUENCE: 47

Met Gly Val Trp Thr Phe Asp Ser Glu Glu Pro Leu Gln Gly Pro Phe
1               5                   10                  15

Asn Phe Arg Phe Leu Thr Glu Lys Gly Met Lys Asn Val Phe Asp Asp
            20                  25                  30

Val Val Pro Glu Lys Tyr Thr Ile Gly Ala Thr Tyr Ala Pro Glu Glu
        35                  40                  45

Val Pro Lys Val Thr Phe Thr Val Glu Lys Gly Ser Asn Glu Lys His
    50                  55                  60

Leu Ala Val Leu Val Lys Tyr Glu Gly Asp Thr Met Ala Glu Val Glu
65                  70                  75                  80

Leu Arg Glu His Gly Ser Asp Glu Trp Val Ala Met Thr Lys Gly Glu
                85                  90                  95

Gly Ala Asp Lys Tyr Lys Thr Phe Glu Ala Ala Phe Thr Val Ser Ser
            100                 105                 110

Lys Arg Asn Leu Ala Asp Ala Val Ser Lys Ala Pro Gln Leu Val Pro
        115                 120                 125

Lys Leu Asp Glu Val Tyr Asn Ala Ala Tyr Asn Ala Ala Asp His Ala
    130                 135                 140

Ala Pro Glu Asp Lys Tyr Glu Ala Phe Val Leu His Phe Ser Glu Ala
145                 150                 155                 160
```

```
Leu Arg Ile Ile Ala Gly Thr Pro Glu Val His Ala Val Lys Pro Gly
                165                 170                 175

Ala His His His His His His
            180

<210> SEQ ID NO 48
<211> LENGTH: 183
<212> TYPE: PRT
<213> ORGANISM: Artificial Sequence
<220> FEATURE:
<223> OTHER INFORMATION: construct K with N-terminal Met and C-terminal
      hexahistidine

<400> SEQUENCE: 48

Met Gly Val Trp Thr Phe Asp Ser Glu Glu Pro Leu Gln Gly Pro Phe
1               5                   10                  15

Asn Phe Arg Phe Leu Thr Glu Lys Gly Met Lys Asn Val Phe Asp Asp
            20                  25                  30

Val Val Pro Glu Lys Tyr Thr Ile Gly Ala Thr Tyr Ala Pro Glu Glu
        35                  40                  45

Ala Asp Lys Tyr Lys Thr Phe Glu Ala Ala Phe Thr Val Ser Ser Lys
    50                  55                  60

Arg Asn Leu Ala Asp Ala Val Ser Lys Ala Pro Gln Leu Val Pro Lys
65                  70                  75                  80

Leu Asp Glu Val Tyr Asn Ala Ala Tyr Asn Ala Asp His Ala Ala
                85                  90                  95

Pro Glu Asp Lys Tyr Glu Ala Phe Val Leu His Phe Ser Glu Ala Leu
            100                 105                 110

Arg Ile Ile Ala Gly Thr Pro Glu Val His Ala Val Lys Pro Gly Ala
        115                 120                 125

Val Pro Lys Val Thr Phe Thr Val Glu Lys Gly Ser Asn Glu Lys His
    130                 135                 140

Leu Ala Val Leu Val Lys Tyr Glu Gly Asp Thr Met Ala Glu Val Glu
145                 150                 155                 160

Leu Arg Glu His Gly Ser Asp Glu Trp Val Ala Met Thr Lys Gly Glu
                165                 170                 175

Gly His His His His His His
            180

<210> SEQ ID NO 49
<211> LENGTH: 183
<212> TYPE: PRT
<213> ORGANISM: Artificial Sequence
<220> FEATURE:
<223> OTHER INFORMATION: construct L with N-terminal Met and C-terminal
      hexahistidine

<400> SEQUENCE: 49

Met Val Pro Lys Val Thr Phe Thr Val Glu Lys Gly Ser Asn Glu Lys
1               5                   10                  15

His Leu Ala Val Leu Val Lys Tyr Glu Gly Asp Thr Met Ala Glu Val
            20                  25                  30

Glu Leu Arg Glu His Gly Ser Asp Glu Trp Val Ala Met Thr Lys Gly
        35                  40                  45

Glu Gly Ala Asp Lys Tyr Lys Thr Phe Glu Ala Ala Phe Thr Val Ser
    50                  55                  60

Ser Lys Arg Asn Leu Ala Asp Ala Val Ser Lys Ala Pro Gln Leu Val
65                  70                  75                  80
```

```
Pro Lys Leu Asp Glu Val Tyr Asn Ala Ala Tyr Asn Ala Ala Asp His
                85                  90                  95

Ala Ala Pro Glu Asp Lys Tyr Glu Ala Phe Val Leu His Phe Ser Glu
            100                 105                 110

Ala Leu Arg Ile Ile Ala Gly Thr Pro Glu Val His Ala Val Lys Pro
        115                 120                 125

Gly Ala Gly Val Trp Thr Phe Asp Ser Glu Glu Pro Leu Gln Gly Pro
130                 135                 140

Phe Asn Phe Arg Phe Leu Thr Glu Lys Gly Met Lys Asn Val Phe Asp
145                 150                 155                 160

Asp Val Val Pro Glu Lys Tyr Thr Ile Gly Ala Thr Tyr Ala Pro Glu
                165                 170                 175

Glu His His His His His His
            180
```

<210> SEQ ID NO 50
<211> LENGTH: 710
<212> TYPE: PRT
<213> ORGANISM: Artificial Sequence
<220> FEATURE:
<223> OTHER INFORMATION: construct M with N-terminal Met and C-terminal
      hexahistidine

<400> SEQUENCE: 50

```
Met Ala Asp Lys Tyr Lys Thr Phe Glu Ala Phe Thr Val Ser Ser
1               5                   10                  15

Lys Arg Asn Leu Ala Asp Ala Val Ser Lys Ala Pro Gln Leu Val Pro
            20                  25                  30

Lys Leu Asp Glu Val Tyr Asn Ala Ala Tyr Asn Ala Ala Asp His Ala
        35                  40                  45

Ala Pro Glu Asp Lys Tyr Glu Ala Phe Val Leu His Phe Ser Glu Ala
    50                  55                  60

Leu Arg Ile Ile Ala Gly Thr Pro Glu Val His Ala Val Lys Pro Gly
65                  70                  75                  80

Ala Gly Val Trp Thr Phe Asp Ser Glu Glu Pro Leu Gln Gly Pro Phe
                85                  90                  95

Asn Phe Arg Phe Leu Thr Glu Lys Gly Met Lys Asn Val Phe Asp Asp
            100                 105                 110

Val Val Pro Glu Lys Tyr Thr Ile Gly Ala Thr Tyr Ala Pro Glu Glu
        115                 120                 125

Val Pro Lys Val Thr Phe Thr Val Glu Lys Gly Ser Asn Glu Lys His
    130                 135                 140

Leu Ala Val Leu Val Lys Tyr Glu Gly Asp Thr Met Ala Glu Val Glu
145                 150                 155                 160

Leu Arg Glu His Gly Ser Asp Glu Trp Val Ala Met Thr Lys Gly Glu
                165                 170                 175

Gly Ser Gly Arg Gly Cys Gly Ser Cys Phe Glu Ile Lys Cys Thr Lys
            180                 185                 190

Pro Glu Ala Cys Ser Gly Glu Pro Val Val His Ile Thr Asp Asp
        195                 200                 205

Asn Glu Glu Pro Ile Ala Pro Tyr His Phe Asp Leu Ser Gly His Ala
    210                 215                 220

Phe Gly Ala Met Ala Lys Lys Gly Asp Glu Gln Lys Leu Arg Thr Gly
225                 230                 235                 240

Pro Phe Thr Val Arg Tyr Thr Thr Glu Gly Gly Thr Lys Thr Glu Ala
                245                 250                 255
```

```
Glu Asp Val Ile Pro Glu Gly Trp Lys Ala Asp Thr Ser Tyr Glu Ser
            260                 265                 270

Lys Gly Ala Ala Ser Asn Lys Ala Phe Ala Glu Gly Leu Ser Gly Glu
        275                 280                 285

Pro Lys Gly Ala Ala Glu Ser Ser Lys Ala Ala Leu Thr Ser Lys
    290                 295                 300

Leu Asp Ala Ala Tyr Lys Leu Ala Tyr Lys Thr Ala Glu Gly Ala Thr
305                 310                 315                 320

Pro Glu Ala Lys Tyr Asp Ala Tyr Val Ala Thr Leu Ser Glu Ala Leu
                325                 330                 335

Arg Ile Ile Ala Gly Thr Leu Glu Val His Ala Val Lys Pro Ala Ala
            340                 345                 350

Asp Leu Gly Tyr Gly Pro Ala Thr Pro Ala Ala Pro Ala Ala Gly Tyr
        355                 360                 365

Thr Pro Ala Thr Pro Ala Ala Pro Ala Glu Ala Ala Pro Ala Gly Lys
    370                 375                 380

Ala Thr Thr Glu Glu Gln Lys Leu Ile Glu Lys Ile Asn Ala Gly Phe
385                 390                 395                 400

Lys Ala Ala Leu Ala Ala Ala Gly Val Gln Pro Ala Asp Lys Tyr
                405                 410                 415

Arg Thr Phe Val Ala Thr Phe Val Lys Gln Ala Tyr Ala Ala Thr
            420                 425                 430

Val Ala Thr Ala Pro Glu Val Lys Tyr Thr Val Phe Glu Thr Ala Leu
                435                 440                 445

Lys Lys Ala Ile Thr Ala Met Ser Glu Ala Gln Lys Ala Lys Pro
            450                 455                 460

Ala Ala Ala Ala Thr Ala Thr Ala Thr Ala Ala Val Gly Ala Ala Thr
465                 470                 475                 480

Gly Ala Ala Thr Ala Ala Thr Gly Gly Tyr Lys Val Ala Glu Glu Val
                485                 490                 495

Lys Val Ile Pro Ala Gly Glu Leu Gln Val Ile Glu Lys Val Asp Ala
            500                 505                 510

Ala Phe Lys Val Ala Ala Thr Ala Ala Asn Ala Ala Pro Ala Asn Asp
        515                 520                 525

Lys Phe Thr Val Phe Glu Ala Ala Phe Asn Asp Ala Ile Lys Ala Ser
    530                 535                 540

Thr Gly Gly Ala Tyr Glu Ser Tyr Lys Phe Ile Pro Ala Leu Glu Ala
545                 550                 555                 560

Ile Pro Lys Val Pro Pro Gly Pro Asn Ile Thr Ala Thr Tyr Gly Asp
                565                 570                 575

Lys Trp Leu Asp Ala Lys Ser Thr Trp Tyr Gly Lys Pro Thr Gly Ala
            580                 585                 590

Gly Pro Lys Asp Asn Gly Gly Ala Cys Gly Tyr Lys Asp Val Asp Lys
        595                 600                 605

Pro Pro Phe Ser Gly Met Thr Gly Cys Gly Asn Thr Pro Ile Phe Lys
    610                 615                 620

Ser Ala Gly Glu Leu Glu Leu Gln Phe Arg Arg Val Lys Cys Lys Tyr
625                 630                 635                 640

Pro Glu Gly Thr Lys Val Thr Phe His Val Glu Lys Gly Ser Asn Pro
                645                 650                 655

Asn Tyr Leu Ala Leu Leu Val Lys Tyr Val Asn Gly Asp Gly Asp Val
            660                 665                 670
```

Val Ala Val Asp Ile Lys Glu Lys Gly Lys Asp Lys Trp Ile Glu Leu
            675                 680                 685

Lys Glu Ser Trp Gly Ala Ile Trp Arg Ile Asp Thr Pro Asp Lys Leu
        690                 695                 700

His His His His His His
705                 710

<210> SEQ ID NO 51
<211> LENGTH: 710
<212> TYPE: PRT
<213> ORGANISM: Artificial Sequence
<220> FEATURE:
<223> OTHER INFORMATION: construct N with N-terminal Met and C-terminal
      hexahistidine

<400> SEQUENCE: 51

Met Ala Asp Lys Tyr Lys Thr Phe Glu Ala Ala Phe Thr Val Ser Ser
1               5                   10                  15

Lys Arg Asn Leu Ala Asp Ala Val Ser Lys Ala Pro Gln Leu Val Pro
            20                  25                  30

Lys Leu Asp Glu Val Tyr Asn Ala Ala Tyr Asn Ala Ala Asp His Ala
        35                  40                  45

Ala Pro Glu Asp Lys Tyr Glu Ala Phe Val Leu His Phe Ser Glu Ala
    50                  55                  60

Leu Arg Ile Ile Ala Gly Thr Pro Glu Val His Ala Val Lys Pro Gly
65                  70                  75                  80

Ala Val Pro Lys Val Thr Phe Thr Val Glu Lys Gly Ser Asn Glu Lys
                85                  90                  95

His Leu Ala Val Leu Val Lys Tyr Glu Gly Asp Thr Met Ala Glu Val
            100                 105                 110

Glu Leu Phe Arg Phe Leu Thr Glu Lys Gly Met Lys Asn Val Phe Asp
        115                 120                 125

Asp Val Val Pro Glu Lys Tyr Thr Ile Gly Ala Thr Tyr Ala Pro Glu
    130                 135                 140

Glu Arg Glu His Gly Ser Asp Glu Trp Val Ala Met Thr Lys Gly Glu
145                 150                 155                 160

Gly Gly Val Trp Thr Phe Asp Ser Glu Glu Pro Leu Gln Gly Pro Phe
                165                 170                 175

Asn Gly Ala Ala Ser Asn Lys Ala Phe Ala Glu Gly Leu Ser Gly Glu
            180                 185                 190

Pro Lys Gly Ala Ala Glu Ser Ser Lys Ala Ala Leu Thr Ser Lys
        195                 200                 205

Leu Asp Ala Ala Tyr Lys Leu Ala Tyr Lys Thr Ala Glu Gly Ala Thr
    210                 215                 220

Pro Glu Ala Lys Tyr Asp Ala Tyr Val Ala Thr Leu Ser Glu Ala Leu
225                 230                 235                 240

Arg Ile Ile Ala Gly Thr Leu Glu Val His Ala Val Lys Pro Ala Ala
                245                 250                 255

Asp Leu Gly Tyr Gly Pro Ala Thr Pro Ala Ala Pro Ala Ala Gly Tyr
            260                 265                 270

Thr Pro Ala Thr Pro Ala Ala Pro Ala Glu Ala Pro Ala Gly Lys
        275                 280                 285

Ala Thr Thr Glu Glu Gln Lys Leu Ile Glu Lys Ile Asn Ala Gly Phe
    290                 295                 300

Lys Ala Ala Leu Ala Ala Ala Ala Gly Val Gln Pro Ala Asp Lys Tyr
305                 310                 315                 320

```
Arg Thr Phe Val Ala Thr Phe Ala Val Lys Gln Ala Tyr Ala Ala Thr
                325                 330                 335

Val Ala Thr Ala Pro Glu Val Lys Tyr Thr Val Phe Glu Thr Ala Leu
            340                 345                 350

Lys Lys Ala Ile Thr Ala Met Ser Glu Ala Gln Lys Ala Ala Lys Pro
        355                 360                 365

Ala Ala Ala Ala Thr Ala Thr Ala Ala Val Gly Ala Ala Thr
    370                 375                 380

Gly Ala Ala Thr Ala Thr Gly Gly Tyr Lys Val Ala Glu Glu Val
385                 390                 395                 400

Lys Val Ile Pro Ala Gly Glu Leu Gln Val Ile Glu Lys Val Asp Ala
                405                 410                 415

Ala Phe Lys Val Ala Ala Thr Ala Ala Asn Ala Ala Pro Ala Asn Asp
            420                 425                 430

Lys Phe Thr Val Phe Glu Ala Ala Phe Asn Asp Ala Ile Lys Ala Ser
        435                 440                 445

Thr Gly Gly Ala Tyr Glu Ser Tyr Lys Phe Ile Pro Ala Leu Glu Ala
    450                 455                 460

Ser Gly Arg Gly Cys Gly Ser Cys Phe Glu Ile Lys Cys Thr Lys Pro
465                 470                 475                 480

Glu Ala Cys Ser Gly Glu Pro Val Val His Ile Thr Asp Asp Asn
                485                 490                 495

Glu Glu Pro Ile Ala Pro Tyr His Phe Asp Leu Ser Gly His Ala Phe
            500                 505                 510

Gly Ala Met Ala Lys Lys Gly Asp Glu Gln Lys Leu Arg Thr Gly Pro
        515                 520                 525

Phe Thr Val Arg Tyr Thr Thr Glu Gly Gly Thr Lys Thr Glu Ala Glu
    530                 535                 540

Asp Val Ile Pro Glu Gly Trp Lys Ala Asp Thr Ser Tyr Glu Ser Lys
545                 550                 555                 560

Ile Pro Lys Val Pro Pro Gly Pro Asn Ile Thr Ala Thr Tyr Gly Asp
                565                 570                 575

Lys Trp Leu Asp Ala Lys Ser Thr Trp Tyr Gly Lys Pro Thr Gly Ala
            580                 585                 590

Gly Pro Lys Asp Asn Gly Gly Ala Cys Gly Tyr Lys Asp Val Asp Lys
        595                 600                 605

Pro Pro Phe Ser Gly Met Thr Gly Cys Gly Asn Thr Pro Ile Phe Lys
    610                 615                 620

Ser Ala Gly Glu Leu Glu Leu Gln Phe Arg Arg Val Lys Cys Lys Tyr
625                 630                 635                 640

Pro Glu Gly Thr Lys Val Thr Phe His Val Glu Lys Gly Ser Asn Pro
                645                 650                 655

Asn Tyr Leu Ala Leu Leu Val Lys Tyr Val Asn Gly Asp Gly Asp Val
            660                 665                 670

Val Ala Val Asp Ile Lys Glu Lys Gly Lys Asp Lys Trp Ile Glu Leu
        675                 680                 685

Lys Glu Ser Trp Gly Ala Ile Trp Arg Ile Asp Thr Pro Asp Lys Leu
    690                 695                 700

His His His His His His
705                 710

<210> SEQ ID NO 52
<211> LENGTH: 534
```

<212> TYPE: PRT
<213> ORGANISM: Artificial Sequence
<220> FEATURE:
<223> OTHER INFORMATION: construct O with N-terminal Met and C-terminal hexahistidine

<400> SEQUENCE: 52

| | | | | | | | | | | | | | | |
|---|---|---|---|---|---|---|---|---|---|---|---|---|---|---|
| Met | Gly | Ala | Ala | Ser | Asn | Lys | Ala | Phe | Ala | Glu | Gly | Leu | Ser | Gly | Glu |
| 1 | | | | 5 | | | | | 10 | | | | | 15 | |
| Pro | Lys | Gly | Ala | Ala | Glu | Ser | Ser | Lys | Ala | Ala | Leu | Thr | Ser | Lys | |
| | | | 20 | | | | | 25 | | | | | 30 | | |
| Leu | Asp | Ala | Ala | Tyr | Lys | Leu | Ala | Tyr | Lys | Thr | Ala | Glu | Gly | Ala | Thr |
| | | | 35 | | | | | 40 | | | | | 45 | | |
| Pro | Glu | Ala | Lys | Tyr | Asp | Ala | Tyr | Val | Ala | Thr | Leu | Ser | Glu | Ala | Leu |
| | 50 | | | | | 55 | | | | | 60 | | | | |
| Arg | Ile | Ile | Ala | Gly | Thr | Leu | Glu | Val | His | Ala | Val | Lys | Pro | Ala | Ala |
| 65 | | | | | 70 | | | | | 75 | | | | | 80 |
| Asp | Leu | Gly | Tyr | Gly | Pro | Ala | Thr | Pro | Ala | Ala | Pro | Ala | Ala | Gly | Tyr |
| | | | | 85 | | | | | 90 | | | | | 95 | |
| Thr | Pro | Ala | Thr | Pro | Ala | Ala | Pro | Ala | Glu | Ala | Ala | Pro | Ala | Gly | Lys |
| | | | 100 | | | | | 105 | | | | | 110 | | |
| Ala | Thr | Thr | Glu | Glu | Gln | Lys | Leu | Ile | Glu | Lys | Ile | Asn | Ala | Gly | Phe |
| | | | 115 | | | | | 120 | | | | | 125 | | |
| Lys | Ala | Ala | Leu | Ala | Ala | Ala | Gly | Val | Gln | Pro | Ala | Asp | Lys | Tyr | |
| | 130 | | | | | 135 | | | | | 140 | | | | |
| Arg | Thr | Phe | Val | Ala | Thr | Phe | Ser | Gly | Arg | Gly | Cys | Gly | Ser | Cys | Phe |
| 145 | | | | | 150 | | | | | 155 | | | | | 160 |
| Glu | Ile | Lys | Cys | Thr | Lys | Pro | Glu | Ala | Cys | Ser | Gly | Glu | Pro | Val | Val |
| | | | | 165 | | | | | 170 | | | | | 175 | |
| Val | His | Ile | Thr | Asp | Asp | Asn | Glu | Glu | Pro | Ile | Ala | Pro | Tyr | His | Phe |
| | | | | 180 | | | | | 185 | | | | | 190 | |
| Asp | Leu | Ser | Gly | His | Ala | Phe | Gly | Ala | Met | Ala | Lys | Lys | Gly | Asp | Glu |
| | | | 195 | | | | | 200 | | | | | 205 | | |
| Gln | Lys | Leu | Arg | Thr | Gly | Pro | Phe | Thr | Val | Arg | Tyr | Thr | Thr | Glu | Gly |
| | 210 | | | | | 215 | | | | | 220 | | | | |
| Gly | Thr | Lys | Thr | Glu | Ala | Glu | Asp | Val | Ile | Pro | Glu | Gly | Trp | Lys | Ala |
| 225 | | | | | 230 | | | | | 235 | | | | | 240 |
| Asp | Thr | Ser | Tyr | Glu | Ser | Lys | Ala | Glu | Glu | Val | Lys | Val | Ile | Pro | Ala |
| | | | | 245 | | | | | 250 | | | | | 255 | |
| Gly | Glu | Leu | Gln | Val | Ile | Glu | Lys | Val | Asp | Ala | Ala | Phe | Lys | Val | Ala |
| | | | 260 | | | | | 265 | | | | | 270 | | |
| Ala | Thr | Ala | Ala | Asn | Ala | Ala | Pro | Ala | Ala | Val | Lys | Gln | Ala | Tyr | Ala |
| | | 275 | | | | | 280 | | | | | 285 | | | |
| Ala | Thr | Val | Ala | Thr | Ala | Pro | Glu | Val | Lys | Tyr | Thr | Val | Phe | Glu | Thr |
| | 290 | | | | | 295 | | | | | 300 | | | | |
| Ala | Leu | Lys | Lys | Ala | Ile | Thr | Ala | Met | Ser | Glu | Ala | Gln | Lys | Ala | Ala |
| 305 | | | | | 310 | | | | | 315 | | | | | 320 |
| Lys | Pro | Ala | Ala | Ala | Ala | Thr | Ala | Thr | Ala | Thr | Ala | Ala | Val | Gly | Ala |
| | | | | 325 | | | | | 330 | | | | | 335 | |
| Ala | Thr | Gly | Ala | Ala | Thr | Ala | Ala | Thr | Gly | Gly | Tyr | Lys | Val | Asn | Asp |
| | | | 340 | | | | | 345 | | | | | 350 | | |
| Lys | Phe | Thr | Val | Phe | Glu | Ala | Ala | Phe | Asn | Asp | Ala | Ile | Lys | Ala | Ser |
| | | 355 | | | | | 360 | | | | | 365 | | | |
| Thr | Gly | Gly | Ala | Tyr | Glu | Ser | Tyr | Lys | Phe | Ile | Pro | Ala | Leu | Glu | Ala |
| | 370 | | | | | 375 | | | | | 380 | | | | |

```
Ser Ala Gly Glu Leu Glu Leu Gln Phe Arg Arg Val Lys Cys Lys Tyr
385                 390                 395                 400

Pro Glu Gly Thr Lys Val Thr Phe His Val Glu Lys Gly Ser Asn Pro
            405                 410                 415

Asn Tyr Leu Ala Leu Leu Val Ile Pro Lys Val Pro Pro Gly Pro Asn
                420                 425                 430

Ile Thr Ala Thr Tyr Gly Asp Lys Trp Leu Asp Ala Lys Ser Thr Trp
            435                 440                 445

Tyr Gly Lys Pro Thr Gly Ala Gly Pro Lys Asp Asn Gly Gly Ala Cys
    450                 455                 460

Gly Tyr Lys Asp Val Asp Lys Pro Pro Phe Ser Gly Met Thr Gly Cys
465                 470                 475                 480

Gly Asn Thr Pro Ile Phe Lys Lys Tyr Val Asn Gly Asp Gly Asp Val
                485                 490                 495

Val Ala Val Asp Ile Lys Glu Lys Gly Lys Asp Lys Trp Ile Glu Leu
            500                 505                 510

Lys Glu Ser Trp Gly Ala Ile Trp Arg Ile Asp Thr Pro Asp Lys Leu
        515                 520                 525

His His His His His His
        530

<210> SEQ ID NO 53
<211> LENGTH: 534
<212> TYPE: PRT
<213> ORGANISM: Artificial Sequence
<220> FEATURE:
<223> OTHER INFORMATION: construct P with N-terminal Met and C-terminal
      hexahistidine

<400> SEQUENCE: 53

Met Gly Ala Ala Ser Asn Lys Ala Phe Ala Glu Gly Leu Ser Gly Glu
1               5                   10                  15

Pro Lys Gly Ala Ala Glu Ser Ser Ser Lys Ala Ala Leu Thr Ser Lys
            20                  25                  30

Leu Asp Ala Ala Tyr Lys Leu Ala Tyr Lys Thr Ala Glu Gly Ala Thr
        35                  40                  45

Pro Glu Ala Lys Tyr Asp Ala Tyr Val Ala Thr Leu Ser Glu Ala Leu
    50                  55                  60

Arg Ile Ile Ala Gly Thr Leu Glu Val His Ala Val Lys Pro Ala Ala
65                  70                  75                  80

Asp Leu Gly Tyr Gly Pro Ala Thr Pro Ala Ala Pro Ala Ala Gly Tyr
                85                  90                  95

Thr Pro Ala Thr Pro Ala Ala Pro Ala Glu Ala Ala Pro Ala Gly Lys
            100                 105                 110

Ala Thr Thr Glu Glu Gln Lys Leu Ile Glu Lys Ile Asn Ala Gly Phe
        115                 120                 125

Lys Ala Ala Leu Ala Ala Ala Gly Val Gln Pro Ala Asp Lys Tyr
    130                 135                 140

Arg Thr Phe Val Ala Thr Phe Ser Gly Arg Gly Cys Gly Ser Cys Phe
145                 150                 155                 160

Glu Ile Lys Cys Thr Lys Pro Glu Ala Cys Ser Gly Glu Pro Val Val
                165                 170                 175

Val His Ile Thr Asp Asp Asn Glu Glu Pro Ile Ala Pro Tyr His Phe
            180                 185                 190

Asp Leu Ser Gly His Ala Phe Gly Ala Met Ala Lys Lys Gly Asp Glu
```

```
                195                 200                 205
Gln Lys Leu Arg Thr Gly Pro Phe Thr Val Arg Tyr Thr Thr Glu Gly
    210                 215                 220

Gly Thr Lys Thr Glu Ala Glu Asp Val Ile Pro Gly Trp Lys Ala
225                 230                 235                 240

Asp Thr Ser Tyr Glu Ser Lys Ala Glu Val Lys Val Ile Pro Ala
                245                 250                 255

Gly Glu Leu Gln Val Ile Glu Lys Val Asp Ala Ala Phe Lys Val Ala
            260                 265                 270

Ala Thr Ala Ala Asn Ala Ala Pro Ala Ala Val Lys Gln Ala Tyr Ala
        275                 280                 285

Ala Thr Val Ala Thr Ala Pro Glu Val Lys Tyr Thr Val Phe Glu Thr
    290                 295                 300

Ala Leu Lys Lys Ala Ile Thr Ala Met Ser Glu Ala Gln Lys Ala Ala
305                 310                 315                 320

Lys Pro Ala Ala Ala Ala Thr Ala Thr Ala Thr Ala Ala Val Gly Ala
                325                 330                 335

Ala Thr Gly Ala Ala Thr Ala Ala Thr Gly Gly Tyr Lys Val Asn Asp
            340                 345                 350

Lys Phe Thr Val Phe Glu Ala Ala Phe Asn Asp Ala Ile Lys Ala Ser
        355                 360                 365

Thr Gly Gly Ala Tyr Glu Ser Tyr Lys Phe Ile Pro Ala Leu Glu Ala
    370                 375                 380

Ile Pro Lys Val Pro Pro Gly Pro Asn Ile Thr Ala Thr Tyr Gly Asp
385                 390                 395                 400

Lys Trp Leu Asp Ala Lys Ser Thr Trp Tyr Gly Lys Pro Thr Gly Ala
                405                 410                 415

Ser Ala Gly Glu Leu Glu Leu Gln Phe Arg Arg Val Lys Cys Lys Tyr
            420                 425                 430

Pro Glu Gly Thr Lys Val Thr Phe His Val Glu Lys Gly Ser Asn Pro
        435                 440                 445

Asn Tyr Leu Ala Leu Leu Val Lys Tyr Val Asn Gly Asp Gly Asp Val
    450                 455                 460

Val Ala Val Asp Ile Lys Glu Lys Gly Lys Asp Lys Trp Ile Glu Leu
465                 470                 475                 480

Lys Glu Ser Trp Gly Ala Ile Trp Arg Ile Asp Thr Pro Asp Lys Leu
                485                 490                 495

Gly Pro Lys Asp Asn Gly Gly Ala Cys Gly Tyr Lys Asp Val Asp Lys
            500                 505                 510

Pro Pro Phe Ser Gly Met Thr Gly Cys Gly Asn Thr Pro Ile Phe Lys
        515                 520                 525

His His His His His His
        530

<210> SEQ ID NO 54
<211> LENGTH: 183
<212> TYPE: PRT
<213> ORGANISM: Artificial Sequence
<220> FEATURE:
<223> OTHER INFORMATION: construct Q with N-terminal Met and C-terminal
      hexahistidine

<400> SEQUENCE: 54

Met Phe Arg Phe Leu Thr Glu Lys Gly Met Lys Asn Val Phe Asp Asp
1               5                   10                  15
```

```
Val Val Pro Glu Lys Tyr Thr Ile Gly Ala Thr Tyr Ala Pro Glu Glu
            20                  25                  30

Asp Glu Trp Val Ala Met Thr Lys Gly Glu Gly Gly Val Trp Thr Phe
        35                  40                  45

Asp Ser Glu Glu Pro Leu Gln Gly Pro Phe Asn Ala Asp Lys Tyr Lys
    50                  55                  60

Thr Phe Glu Ala Ala Phe Thr Val Ser Ser Lys Arg Asn Leu Ala Asp
65                  70                  75                  80

Ala Val Ser Lys Ala Pro Gln Leu Val Pro Lys Leu Asp Glu Val Tyr
                85                  90                  95

Asn Ala Ala Tyr Asn Ala Ala Asp His Ala Ala Pro Glu Asp Lys Tyr
            100                 105                 110

Glu Ala Phe Val Leu His Phe Ser Glu Ala Leu Arg Ile Ile Ala Gly
        115                 120                 125

Thr Pro Glu Val His Ala Val Lys Pro Gly Ala Val Pro Lys Val Thr
    130                 135                 140

Phe Thr Val Glu Lys Gly Ser Asn Glu Lys His Leu Ala Val Leu Val
145                 150                 155                 160

Lys Tyr Glu Gly Asp Thr Met Ala Glu Val Glu Leu Arg Glu His Gly
                165                 170                 175

Ser His His His His His His
            180

<210> SEQ ID NO 55
<211> LENGTH: 64
<212> TYPE: PRT
<213> ORGANISM: Artificial Sequence
<220> FEATURE:
<223> OTHER INFORMATION: fragment P1a

<400> SEQUENCE: 55

Ile Pro Lys Val Pro Pro Gly Pro Asn Ile Thr Ala Thr Tyr Gly Asp
1               5                   10                  15

Lys Trp Leu Asp Ala Lys Ser Thr Trp Tyr Gly Lys Pro Thr Gly Ala
            20                  25                  30

Gly Pro Lys Asp Asn Gly Gly Ala Cys Gly Tyr Lys Asp Val Asp Lys
        35                  40                  45

Pro Pro Phe Ser Gly Met Thr Gly Cys Gly Asn Thr Pro Ile Phe Lys
    50                  55                  60

<210> SEQ ID NO 56
<211> LENGTH: 61
<212> TYPE: PRT
<213> ORGANISM: Artificial Sequence
<220> FEATURE:
<223> OTHER INFORMATION: fragment P1b

<400> SEQUENCE: 56

Ser Gly Arg Gly Cys Gly Ser Cys Phe Glu Ile Lys Cys Thr Lys Pro
1               5                   10                  15

Glu Ala Cys Ser Gly Glu Pro Val Val Val His Ile Thr Asp Asp Asn
            20                  25                  30

Glu Glu Pro Ile Ala Pro Tyr His Phe Asp Leu Ser Gly His Ala Phe
        35                  40                  45

Gly Ala Met Ala Lys Lys Gly Asp Glu Gln Lys Leu Arg
    50                  55                  60

<210> SEQ ID NO 57
```

```
<211> LENGTH: 80
<212> TYPE: PRT
<213> ORGANISM: Artificial Sequence
<220> FEATURE:
<223> OTHER INFORMATION: fragment P1c

<400> SEQUENCE: 57
```

Ser Ala Gly Glu Leu Glu Leu Gln Phe Arg Arg Val Lys Cys Lys Tyr
1               5                   10                  15

Pro Glu Gly Thr Lys Val Thr Phe His Val Glu Lys Gly Ser Asn Pro
            20                  25                  30

Asn Tyr Leu Ala Leu Leu Val Lys Tyr Val Asn Gly Asp Gly Asp Val
        35                  40                  45

Val Ala Val Asp Ile Lys Glu Lys Gly Lys Asp Lys Trp Ile Glu Leu
    50                  55                  60

Lys Glu Ser Trp Gly Ala Ile Trp Arg Ile Asp Thr Pro Asp Lys Leu
65                  70                  75                  80

```
<210> SEQ ID NO 58
<211> LENGTH: 35
<212> TYPE: PRT
<213> ORGANISM: Artificial Sequence
<220> FEATURE:
<223> OTHER INFORMATION: fragment P1d

<400> SEQUENCE: 58
```

Thr Gly Pro Phe Thr Val Arg Tyr Thr Thr Glu Gly Gly Thr Lys Thr
1               5                   10                  15

Glu Ala Glu Asp Val Ile Pro Glu Gly Trp Lys Ala Asp Thr Ser Tyr
            20                  25                  30

Glu Ser Lys
        35

```
<210> SEQ ID NO 59
<211> LENGTH: 32
<212> TYPE: PRT
<213> ORGANISM: Artificial Sequence
<220> FEATURE:
<223> OTHER INFORMATION: fragment P1a1

<400> SEQUENCE: 59
```

Ile Pro Lys Val Pro Gly Pro Asn Ile Thr Ala Thr Tyr Gly Asp
1               5                   10                  15

Lys Trp Leu Asp Ala Lys Ser Thr Trp Tyr Gly Lys Pro Thr Gly Ala
            20                  25                  30

```
<210> SEQ ID NO 60
<211> LENGTH: 32
<212> TYPE: PRT
<213> ORGANISM: Artificial Sequence
<220> FEATURE:
<223> OTHER INFORMATION: fragment P1a2

<400> SEQUENCE: 60
```

Gly Pro Lys Asp Asn Gly Gly Ala Cys Gly Tyr Lys Asp Val Asp Lys
1               5                   10                  15

Pro Pro Phe Ser Gly Met Thr Gly Cys Gly Asn Thr Pro Ile Phe Lys
            20                  25                  30

```
<210> SEQ ID NO 61
<211> LENGTH: 39
<212> TYPE: PRT
<213> ORGANISM: Artificial Sequence
```

```
<220> FEATURE:
<223> OTHER INFORMATION: fragment P1c1

<400> SEQUENCE: 61

Ser Ala Gly Glu Leu Glu Leu Gln Phe Arg Arg Val Lys Cys Lys Tyr
1               5                   10                  15

Pro Glu Gly Thr Lys Val Thr Phe His Val Glu Lys Gly Ser Asn Pro
            20                  25                  30

Asn Tyr Leu Ala Leu Leu Val
        35

<210> SEQ ID NO 62
<211> LENGTH: 41
<212> TYPE: PRT
<213> ORGANISM: Artificial Sequence
<220> FEATURE:
<223> OTHER INFORMATION: fragment P1c2

<400> SEQUENCE: 62

Lys Tyr Val Asn Gly Asp Gly Asp Val Val Ala Val Asp Ile Lys Glu
1               5                   10                  15

Lys Gly Lys Asp Lys Trp Ile Glu Leu Lys Glu Ser Trp Gly Ala Ile
            20                  25                  30

Trp Arg Ile Asp Thr Pro Asp Lys Leu
        35                  40

<210> SEQ ID NO 63
<211> LENGTH: 49
<212> TYPE: PRT
<213> ORGANISM: Artificial Sequence
<220> FEATURE:
<223> OTHER INFORMATION: fragment P2A

<400> SEQUENCE: 63

Val Pro Lys Val Thr Phe Thr Val Glu Lys Gly Ser Asn Glu Lys His
1               5                   10                  15

Leu Ala Val Leu Val Lys Tyr Glu Gly Asp Thr Met Ala Glu Val Glu
            20                  25                  30

Leu Arg Glu His Gly Ser Asp Glu Trp Val Ala Met Thr Lys Gly Glu
        35                  40                  45

Gly

<210> SEQ ID NO 64
<211> LENGTH: 47
<212> TYPE: PRT
<213> ORGANISM: Artificial Sequence
<220> FEATURE:
<223> OTHER INFORMATION: fragment P2B

<400> SEQUENCE: 64

Gly Val Trp Thr Phe Asp Ser Glu Glu Pro Leu Gln Gly Pro Phe Asn
1               5                   10                  15

Phe Arg Phe Leu Thr Glu Lys Gly Met Lys Asn Val Phe Asp Asp Val
            20                  25                  30

Val Pro Glu Lys Tyr Thr Ile Gly Ala Thr Tyr Ala Pro Glu Glu
        35                  40                  45

<210> SEQ ID NO 65
<211> LENGTH: 33
<212> TYPE: PRT
<213> ORGANISM: Artificial Sequence
<220> FEATURE:
```

<223> OTHER INFORMATION: fragment P2a

<400> SEQUENCE: 65

Val Pro Lys Val Thr Phe Thr Val Glu Lys Gly Ser Asn Glu Lys His
1               5                   10                  15

Leu Ala Val Leu Val Lys Tyr Glu Gly Asp Thr Met Ala Glu Val Glu
            20                  25                  30

Leu

<210> SEQ ID NO 66
<211> LENGTH: 32
<212> TYPE: PRT
<213> ORGANISM: Artificial Sequence
<220> FEATURE:
<223> OTHER INFORMATION: fragment P2b

<400> SEQUENCE: 66

Arg Glu His Gly Ser Asp Glu Trp Val Ala Met Thr Lys Gly Glu Gly
1               5                   10                  15

Gly Val Trp Thr Phe Asp Ser Glu Glu Pro Leu Gln Gly Pro Phe Asn
            20                  25                  30

<210> SEQ ID NO 67
<211> LENGTH: 31
<212> TYPE: PRT
<213> ORGANISM: Artificial Sequence
<220> FEATURE:
<223> OTHER INFORMATION: fragment P2c

<400> SEQUENCE: 67

Phe Arg Phe Leu Thr Glu Lys Gly Met Lys Asn Val Phe Asp Asp Val
1               5                   10                  15

Val Pro Glu Lys Tyr Thr Ile Gly Ala Thr Tyr Ala Pro Glu Glu
            20                  25                  30

<210> SEQ ID NO 68
<211> LENGTH: 38
<212> TYPE: PRT
<213> ORGANISM: Artificial Sequence
<220> FEATURE:
<223> OTHER INFORMATION: fragment P2a1

<400> SEQUENCE: 68

Val Pro Lys Val Thr Phe Thr Val Glu Lys Gly Ser Asn Glu Lys His
1               5                   10                  15

Leu Ala Val Leu Val Lys Tyr Glu Gly Asp Thr Met Ala Glu Val Glu
            20                  25                  30

Leu Arg Glu His Gly Ser
        35

<210> SEQ ID NO 69
<211> LENGTH: 27
<212> TYPE: PRT
<213> ORGANISM: Artificial Sequence
<220> FEATURE:
<223> OTHER INFORMATION: fragment P2b2

<400> SEQUENCE: 69

Asp Glu Trp Val Ala Met Thr Lys Gly Glu Gly Gly Val Trp Thr Phe
1               5                   10                  15

Asp Ser Glu Glu Pro Leu Gln Gly Pro Phe Asn
            20                  25

<210> SEQ ID NO 70
<211> LENGTH: 72
<212> TYPE: PRT
<213> ORGANISM: Artificial Sequence
<220> FEATURE:
<223> OTHER INFORMATION: fragment P5a

<400> SEQUENCE: 70

```
Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Glu Ala Ala Pro Ala Gly
            20                  25                  30

Lys Ala Thr Thr Glu Glu Gln Lys Leu Ile Glu Lys Ile Asn Ala Gly
        35                  40                  45

Phe Lys Ala Ala Leu Ala Ala Ala Ala Gly Val Gln Pro Ala Asp Lys
    50                  55                  60

Tyr Arg Thr Phe Val Ala Thr Phe
65                  70
```

<210> SEQ ID NO 71
<211> LENGTH: 78
<212> TYPE: PRT
<213> ORGANISM: Artificial Sequence
<220> FEATURE:
<223> OTHER INFORMATION: fragment P5b

<400> SEQUENCE: 71

```
Gly Ala Ala Ser Asn Lys Ala Phe Ala Glu Gly Leu Ser Gly Glu Pro
1               5                   10                  15

Lys Gly Ala Ala Glu Ser Ser Ser Lys Ala Ala Leu Thr Ser Lys Leu
            20                  25                  30

Asp Ala Ala Tyr Lys Leu Ala Tyr Lys Thr Ala Glu Gly Ala Thr Pro
        35                  40                  45

Glu Ala Lys Tyr Asp Ala Tyr Val Ala Thr Leu Ser Glu Ala Leu Arg
    50                  55                  60

Ile Ile Ala Gly Thr Leu Glu Val His Ala Val Lys Pro Ala
65                  70                  75
```

<210> SEQ ID NO 72
<211> LENGTH: 68
<212> TYPE: PRT
<213> ORGANISM: Artificial Sequence
<220> FEATURE:
<223> OTHER INFORMATION: fragment P5c

<400> SEQUENCE: 72

```
Ala Glu Glu Val Lys Val Ile Pro Ala Gly Glu Leu Gln Val Ile Glu
1               5                   10                  15

Lys Val Asp Ala Ala Phe Lys Val Ala Ala Thr Ala Ala Asn Ala Ala
            20                  25                  30

Pro Ala Asn Asp Lys Phe Thr Val Phe Glu Ala Ala Phe Asn Asp Ala
        35                  40                  45

Ile Lys Ala Ser Thr Gly Gly Ala Tyr Glu Ser Tyr Lys Phe Ile Pro
    50                  55                  60

Ala Leu Glu Ala
65
```

<210> SEQ ID NO 73
<211> LENGTH: 69
<212> TYPE: PRT

```
<213> ORGANISM: Artificial Sequence
<220> FEATURE:
<223> OTHER INFORMATION: fragment P5d

<400> SEQUENCE: 73

Ala Val Lys Gln Ala Tyr Ala Ala Thr Val Ala Thr Ala Pro Glu Val
1               5                   10                  15

Lys Tyr Thr Val Phe Glu Thr Ala Leu Lys Lys Ala Ile Thr Ala Met
            20                  25                  30

Ser Glu Ala Gln Lys Ala Ala Lys Pro Ala Ala Ala Thr Ala Thr
        35                  40                  45

Ala Thr Ala Ala Val Gly Ala Thr Gly Ala Ala Thr Ala Ala Thr
    50                  55                  60

Gly Gly Tyr Lys Val
65

<210> SEQ ID NO 74
<211> LENGTH: 34
<212> TYPE: PRT
<213> ORGANISM: Artificial Sequence
<220> FEATURE:
<223> OTHER INFORMATION: fragment P5c1

<400> SEQUENCE: 74

Ala Glu Glu Val Lys Val Ile Pro Ala Gly Glu Leu Gln Val Ile Glu
1               5                   10                  15

Lys Val Asp Ala Ala Phe Lys Val Ala Ala Thr Ala Ala Asn Ala Ala
            20                  25                  30

Pro Ala

<210> SEQ ID NO 75
<211> LENGTH: 34
<212> TYPE: PRT
<213> ORGANISM: Artificial Sequence
<220> FEATURE:
<223> OTHER INFORMATION: fragment P5c2

<400> SEQUENCE: 75

Asn Asp Lys Phe Thr Val Phe Glu Ala Ala Phe Asn Asp Ala Ile Lys
1               5                   10                  15

Ala Ser Thr Gly Gly Ala Tyr Glu Ser Tyr Lys Phe Ile Pro Ala Leu
            20                  25                  30

Glu Ala

<210> SEQ ID NO 76
<211> LENGTH: 80
<212> TYPE: PRT
<213> ORGANISM: Artificial Sequence
<220> FEATURE:
<223> OTHER INFORMATION: fragment P6b

<400> SEQUENCE: 76

Ala Asp Lys Tyr Lys Thr Phe Glu Ala Ala Phe Thr Val Ser Ser Lys
1               5                   10                  15

Arg Asn Leu Ala Asp Ala Val Ser Lys Ala Pro Gln Leu Val Pro Lys
            20                  25                  30

Leu Asp Glu Val Tyr Asn Ala Ala Tyr Asn Ala Ala Asp His Ala Ala
        35                  40                  45

Pro Glu Asp Lys Tyr Glu Ala Phe Val Leu His Phe Ser Glu Ala Leu
    50                  55                  60
```

-continued

```
Arg Ile Ile Ala Gly Thr Pro Glu Val His Ala Val Lys Pro Gly Ala
65                  70                  75                  80
```